US011118165B2

(12) United States Patent
Spanholtz et al.

(10) Patent No.: US 11,118,165 B2
(45) Date of Patent: Sep. 14, 2021

(54) GENERATION OF NK CELLS AND NK-CELL PROGENITORS

(75) Inventors: Jan Spanholtz, Kleve (DE); Harmen Dolstra, Nijmegen (NL)

(73) Assignee: GLYCOSTEM THERAPEUTICS B.V., Oss (NL)

(*) Notice: Subject to any disclaimer, the term of this patent is extended or adjusted under 35 U.S.C. 154(b) by 427 days.

(21) Appl. No.: 14/005,168

(22) PCT Filed: Mar. 16, 2012

(86) PCT No.: PCT/NL2012/050165
§ 371 (c)(1),
(2), (4) Date: Dec. 2, 2013

(87) PCT Pub. No.: WO2012/128622
PCT Pub. Date: Sep. 27, 2012

(65) Prior Publication Data
US 2014/0080148 A1  Mar. 20, 2014

(30) Foreign Application Priority Data

Mar. 18, 2011 (WO) ................ PCT/NL2011/050193
Apr. 18, 2011 (EP) .................................... 11162866

(51) Int. Cl.
*C12N 5/0783* (2010.01)
*C12N 5/0789* (2010.01)

(52) U.S. Cl.
CPC ...... *C12N 5/0646* (2013.01); *C12N 2501/125* (2013.01); *C12N 2501/145* (2013.01); *C12N 2501/21* (2013.01); *C12N 2501/22* (2013.01); *C12N 2501/2302* (2013.01); *C12N 2501/235* (2013.01); *C12N 2501/2306* (2013.01); *C12N 2501/2307* (2013.01); *C12N 2501/2315* (2013.01); *C12N 2501/26* (2013.01); *C12N 2501/91* (2013.01)

(58) Field of Classification Search
None
See application file for complete search history.

(56) References Cited

U.S. PATENT DOCUMENTS

| 9,109,202 | B2 * | 8/2015 | Spanholtz | ............ | C12N 5/0607 |
| 9,193,953 | B2 * | 11/2015 | Spanholtz | ............ | C12N 5/0607 |
| 2010/0233192 | A1 * | 9/2010 | Park | ............ | C12N 5/0646 |
| | | | | | 424/184.1 |

FOREIGN PATENT DOCUMENTS

| WO | WO 07/037682 A1 * | 5/2007 |
| WO | 2008/118020 | 10/2008 |
| WO | 2011/080740 | 7/2011 |
| WO | 2011/103882 | 9/2011 |
| WO | 2017077096 A1 | 5/2017 |

OTHER PUBLICATIONS

Sutlu et al (Cytotherapy, 12/10, 12: 1044-1055).*
Fujisaki et al (Canc. Res., 69(9): 4010-4017, published online Apr. 21, 2009).*
Drugs.com (3/15).*
Spanholtz et al (Blood, Nov. 16, 2008, 112(11): 1003).*
Lapierre et al (Glycobiol. 1996, 6(3): 355-366).*
Sumide et al (Nature Comm. 2018, pp. 1-17, DOI: 10.1038/s41467-018-04441-z) (Year: 2018).*
Carlens, et al., A New Method for in Vitro Expansion of Cytotoxic Human CD3-CD56+ Natural Killer Cells, Human Immunology 62, 1092-1098 (2001).
J. Spanholtz et al., High Log-Scale Expansion of Functional Human Natural Killer Cells from Umbilical Cord Blood CD34-Positive Cells for Adoptive Cancer Immunotherapy, PLOS One, vol. 5, Issue 2 (2010).
A. Freud, et al., Evidence for discrete stages of human natural killer cell differentiation in vivo, JEM vol. 203, No. 4, pp. 1033-1043 (2006).
T. Sutlu et al., Clinical-grade, large-scale, feeder-free expansion of highly active human natural killer cells for adoptive immunotherapy using an automated bioreactor, Cyotherapy, pp. 1044-1055 (2010).
J. Spanholtz, et al., Clinical-Grade Generation of Active NK Cells from Cord Blood Hematopoietic Progenitor Cells for Immunotherapy Using a Closed-System Culture Process, PLOS One, vol. 6, Issue 6 (2011).
Miller, et al., "Successfuly adoptive transfer and in vivo expansion of human haploidentical NK cells in patents with cancer", Clinical Observations, Interventions, and Therapeutic Trails, pp. 3051-3057Blood, Apr. 15, 2005, vol. 105, No. 8.
Klingemann, et al., "Ex vivo expansion of natural killer cells for clinical applications", Cytotherapy (2004), vol. 6, No. 1, 15-22, Taylor & Francis healthsciences.
Nguyen, et al., "Clinical impact of NK-cell reconstitution after reduced intensity conditioned unrelated cord blood tranplantation in patients with acute myeloid leukemia: analysis of a prospective phase II multicenter trial on behalf of the Société Française de Greffe de Moelle Osseuse et Thérapie Cellulaire and Eurocord," Bone Marrow Transplantation, pp. 1428-1435, 52 (2017).
Fehniger, et al., "A Phase 1 Trial of CNDO-109-Activated Natural Killer Cells in Patients with High-Risk Acute Myeloid Leukemia," Biol. Blood Marrow Transplant, pp. 1581-1589, 24 (2018).

* cited by examiner

*Primary Examiner* — G. R. Ewoldt
*Assistant Examiner* — Marianne DiBrino
(74) *Attorney, Agent, or Firm* — Hoffmann & Baron, LLP

(57) ABSTRACT

The present invention provides a cytokine-based culture method for ex vivo expansion of NK cells from postembryonic hematopoietic stem cells into a fully closed, large-scale, cell culture bioprocess. We optimized enrichment of CD34$^+$ cells followed by efficient expansion in gas-permeable cell culture bags. Thereafter, expanded CD34$^+$ cells could be reproducibly amplified and differentiated into CD56$^+$CD3$^-$ NK cell products with a mean expansion of more than 2,000 fold and a purity of >90%. Also provided are collections of cultured cells having specific properties.

8 Claims, 36 Drawing Sheets

GENERATION OF NK CELLS AND NK-CELL PROGENITORS

This application is the U.S. National Phase of, and Applicants claim priority from, International Application No. PCT/NL2012/050165 filed Mar. 16, 2012, which claims priority from PCT/NL2011/050193 filed Mar. 18, 2011 and European Application No. EP 11162866.5 filed Apr. 18, 2011, each of which are incorporated herein by reference.

BACKGROUND OF THE INVENTION

The invention relates to the field of modern medical biology. In particular the invention relates to stem cell technology. More in particular the invention relates to stem cell technology, in particular postembryonic stem cell technology and the generation of NK cells for cultures of such cells.

Natural Killer (NK) cells are $CD3^-CD56^+$ lymphocytes that exert innate immunity against cancer and viral infections [1]. Recognition and subsequent killing of virus-infected and transformed cells by NK cells is regulated through the balance of signals from inhibitory and activating receptors [1]. Due to their strong ability to target tumor cells, NK cells have been described as promising effectors for adoptive immunotherapy against cancer [2]. It has been demonstrated that NK cell alloreactivity can control relapse of acute myeloid leukemia (AML) without causing graft-versus-host disease (GVHD) in the setting of haploidentical stem cell transplantation (SCT) [3]. Moreover, haploidentical NK cell infusions in adult and childhood AML following lymphocyte depleting chemotherapy have provided encouraging results [4,5]. However, only a few trials investigating adoptive NK cell infusions in patients with cancer have been conducted to date. A major obstacle is that only relative small numbers of NK cells can be isolated from regular leukapheresis products. This hampers clinical trials for NK-cell dose dependent anti-tumor responses in humans with cancer [6-11]. Therefore, ex vivo protocols for expansion and activation of NK cells are under investigation enabling clinical trials at higher NK cell dosages and to permit multiple NK cell infusions[12-16]. However, most protocols still deal with technical disadvantages by using supportive feeder cell lines that could lead to regulatory problems producing NK cell products for large-scale and multi-center trials.

Recently, we have described an alternative cytokine-based culture method with the capability of generating clinically relevant NK cell products with high cell numbers, high purity and functionality from umbilical cord blood derived hematopoietic stem cells (UCB-HSC) [17]. UCB is a very attractive source of HSC not only for allogeneic SCT, but also for producing a multitude of therapeutic cell products including NK cells [17-19].

DESCRIPTION OF THE INVENTION

In the present invention we describe the feasibility of large scale NK cell generation using cryopreserved UCB units as progenitor cell source. We have optimized the enrichment of CD34+ cells from thawed UCB units using the CLINIMACS® system. Furthermore, we have developed a scalable procedure that results in high yields of CD34+ cells-derived NK cells. The resultant NK-cells are highly active and functional and are earmarked to be used in a phase I dose-finding trial in elderly AML patients that are not eligible for allogeneic SCT.

To this end the invention provides a method for producing a collection of natural killer (NK) cells said method comprising i—providing a sample comprising stem cells, progenitor cells or both, from human postembryonic tissue, ii—culturing said cells of step (i) at a cell density of at least $0.5 \times 10E^6$/ml for at least 7 days in a culture medium comprising human serum, a collection of cytokines and low molecular weight heparin (LMWH), wherein said collection of cytokines comprises three or more of stem cell factor (SCF), flt-3Ligand (FLT-3L), thrombopoietin (TPO) and interleukin-7 (IL-7) and three or more of granulocyte-macrophage-colony-stimulating factor (GM-CSF), granulocyte-colony-stimulating factor (G-CSF), interleukin-6 (IL-6), leukaemia-inhibitory factor (LIF) and Macrophage-inflammatory protein-1alpha (MIP-I alpha) thereby obtaining a collection of cultured stem cells, progenitor cells or both, from human postembryonic tissue containing a plurality of progenitor cells committed to the NK cell lineage, and preferably iii—culturing cells obtained in step (ii) for at least 7 days at a cell density of at least $1 \times 10E^6$/ml in a culture medium comprising human serum and a collection of cytokines, wherein said collection of cytokines comprises three or more of stem cell factor (SCF), interleukin-7 (IL-7), interleukin-15 and interleukin-2 and three or more of granulocyte-macrophage-colony-stimulating factor (GM-CSF), granulocyte-colony-stimulating factor (G-CSF), interleukin-6 (IL-6), leukaemia-inhibitory factor (LIF) and Macrophage-inflammatory protein-1alpha (MIP-I alpha), thereby obtaining a collection of cultured cells containing a plurality of NK cells or NK progenitor cells or both.

The stem cell for use in a method of the invention can be any stem cell derived from human postembryonic tissue as long as the stem cell has the capability or has acquired the capability to produce progenitor cells that are committed to the hemopoietic lineage. Examples of such stem cells are stem cells from: the bone marrow of adults, mobilized peripheral blood, from fat tissue (mesenchymal stem cells), from the blood of a new born infant, preferably from blood collected from the umbilical cord, after disconnecting it from the newborn. Presently stem cells can be obtained from stem cell lines that have been generated previously. Presently it is also possible to reprogram tissue specific stem cells such as skin stem cells to produce committed progenitors cells in the hemopoietic lineage. It has even been shown to be possible to reprogram differentiated cells, such as skin cells, into fully functional stem cells that can produce progeny of progenitor cells that are committed to producing differentiated progeny of the hemopoietic lineage. All of such stem cells are suitable stem cells for the present invention. A preferred source of stem cells is stem cells from hemopoietic and/or mesenchymal human post-embryonic tissue. Preferably from human tissue obtained from postpartum humans. A particularly preferred source is human cord blood. In a particularly preferred embodiment said source is a source of frozen human cord blood.

Many basic media are known. A selection is given below, but many more may be suitable. Basic media include but are not limited to BEM (Basic Eagle Medium), DMEM (Dulbecco's modified Eagle Medium), Glasgow minimal essential medium, M199 basal medium, HAMs F-10, HAMs F-12, Iscove's DMEM, RPMI, Leibovitz L15, MCDB, McCoy 5A, StemSpan H3000® and StemSpanSFEM®, Stemline I™ and Stemline II™, Glycostem Basal growth medium (GBGM™); X-Vivo10™, X-Vivo15™ and X-Vivo20™ etc.

Combinations of these basic media can also be used. Preferably serum-free formulations, such as Stemline I™ and Stemline II™, StemSpan H3000®, StemSpan SFEM® or X-Vivo10™, GBGM, X-Vivo15™ and X-Vivo20™ will be used at the time point of initiation of culture with and/or without the addition of human serum. Combinations of DMEM and HAMs F-12 are preferred at specific time points according to the invention. The amounts given herein are typically suitable for cultures. The amounts may be adapted for different amounts of cells with which cultures are started.

The media according to the invention can be varied in their serum content, preferably together with a different combination of cytokines to provide either an expansion medium or a differentiation medium and or alternatively an expansion+differentiation medium at defined time points according to the invention.

A progenitor cell is a biological cell that, like a stem cell, has a tendency to differentiate into a specific type of cell, but is already more specific than a stem cell and is pushed to differentiate into its "target" cell. A difference between stem cells and progenitor cells is that stem cells can replicate indefinitely, whereas progenitor cells can only divide a limited number of times. Another difference is the expression of surface markers. Stem cells typically lack surface markers that are prominent on the progenitor cells or differentiated cells derived from them.

Natural killer cells of (NK cells) are a type of cytotoxic lymphocyte that constitute a major component of the innate immune system. NK cells play a major role in the rejection of tumors and cells infected by viruses. They kill cells by releasing small cytoplasmic granules of proteins called perforin and granzyme that cause the target cell to die by apoptosis (programmed cell death). NK cells are defined as large granular lymphocytes (LGL) and constitute the third kind of cells differentiated from the common lymphoid progenitor generating B and T lymphocytes. They do not express T-cell antigen receptors (TCR) or Pan T marker CD3 or surface immunoglobulins (Ig) B cell receptors but they usually express the surface markers CD16 (FcγRIII) and CD56 in humans, NK1.1 or NK1.2 in C57BL/6 mice. Up to 80% of human NK cells also express CD8. They were named "natural killers" because of the initial notion that they do not require activation in order to kill cells that are missing "self" markers of major histocompatibility complex (MHC) class I. They are distinct from Natural Killer T cells. (for review see, Di Santo: 2006, Annu. Rev. Immunol. Vol 24:257-286; Colucci et al.: 2003, Nature reviews Immunology Vol 3:413-428 and Lanier: 2005, Annu. Rev. Immunol. Vol 23:225-274.)

We have observed that for yield it is important to perform essentially two different culturing steps. In the first culture step, (step ii) in a method of the invention, the progenitor population is expanded using a specific culture medium (this step is also referred to as an expansion step). Cells collected from step ii, are in a further culture step (step iii in a method of the invention, differentiated into more committed NK progenitor cells and NK cells (this step is also referred to as a differentiation step). A surprising finding was that the cell density that allowed good yields in the present scalable system differed from the cell densities that were optimal when compared to similar cultures using small scale culture plates. It was found that in step ii of a method of the invention a cell density of at least $0.5 \times 10E^6$ per ml was needed for optimal yields at the end this culture step. Even better yields were obtained for a density of at least $1 \times 10E^6$ cells per ml. Best performance of the cultures was obtained when the cell densities in step ii, were adjusted to at least $0.5 \times 10E^6$ per ml, and preferably at least $1 \times 10E^6$ per ml every two or three days, to accommodate the increase in the number of cells during culture. This is preferably done when changing or adding fresh culture medium to the culture.

For the cultures of step iii, it was found that the optimal cell density was at least $1 \times 10E^6$ cells/ml, preferably at least $2 \times 10E^6$ cells/ml. Best performance of the cultures was obtained when the cell densities in step iii, were adjusted to at least $1 \times 10E^6$ per ml, and preferably at least $2 \times 10E^6$ per ml every two or three days, to accommodate the increase in the number of cells during culture. This is preferably done when changing or adding fresh culture medium to the culture. From a medical point of view cell therapies offer a promising perspective. Since the 1970's the health benefit of stem cell transplantation in case of leukemia is above reasonable doubt. The other side of the coin for cell therapies are the inherent costs, for example some € 200.000 for a standard bone marrow transplantation. Newer cell therapies, like Dendreon's PROVENGE® for treating prostate cancer, a patient personalized autologous DC-vaccine, have similar cost structure. However PROVENGE® only offers a 2-3 month's life extension to the patient at $93.000 re-imbursement costs. Therefore It is an object of the present invention that a significant cost reduction is achieved in cell therapies. An important part of the means and methods of the present invention is directed towards achieving costs savings in cell therapy. One aspect of the invention in which this is apparent is the unprecedented cell yields and purity as compared to state of the art. Another advantage of the present invention is that the source material for cell production is cord blood as opposed to cells obtained from adult blood. Another advantage is that the cell yield from a single cord blood using a method of the present invention is high enough for several batches of generated NK-cells. This allows multiple treatments of the recipient with the NK-cells having the same genetic background. This was previously not possible and when multiple treatments were needed this needed to be achieved using cells from a different individual leading to increased variability and reduced predictability of effects. Often it was indeed necessary to use cells from multiple donors in a single transplant.

A previous disadvantage of cord blood was that often suboptimal numbers of cells could be collected from the cord. A further advantage of the means and methods of the invention is that the log-scale expansion allows the use of such cord bloods with previously suboptimal numbers of cells. The expansions achieved in the present invention more than compensate for the initial lower cells numbers. This further reduces the costs of the procedure as cord bloods with higher cell numbers are "much" more expensive.

The high yield also allows a further adaptation of the procedure in that it is no longer necessary to change medium as the rate of increase in cell numbers allows the culture steps (ii), (iia) and (iii) to be performed as fed-batch cultures wherein medium is added to the cultures instead of culture methods wherein the medium needs to be replaced to accommodate use of the medium in the absence of 'sufficient' cell expansion. Thus in a preferred embodiment a method for producing a collection of NK cells of the invention comprises culturing the cells in culture step ii, iia and/or iii as a fed-batch culture. Thus in a preferred embodiment a method for producing a collection of NK cells of the invention comprises culturing the cells in culture step ii, iia and/or iii by adding fresh medium to the cultures. Thus in a preferred embodiment a method for producing a collection of NK cells of the invention comprises culturing the cells in culture step ii, iia and/or iii by adding culture medium and not replacing culture medium.

The culture time is at least 7 days for both culture steps. Shorter time period are possible but generally result in significantly lower yields. Culture step ii of a method of the invention is preferably performed for at least 10 days, preferably at least 14 days. Culture times of more than 14 days are possible but tend to result in the same up to 18 days or eventually lower yields of cells (more than 18 days of culture) that are active in culture step iii of a method of the invention. Step iii of a method of the invention is preferably performed for at least 10 days, more preferably at least 14 days. This time period can be increased to 21 days and even 28 days. Culturing periods that extend beyond day 18 typically yield the same number of cells but the population of cells in general is shifted to more differentiated NK cells, i.e. containing a higher percentage of cells with markers that are typical for more differentiated NK-cells.

Low molecular weight heparins (LMHWs) are used in the clinic, for instance as an anti-coagulant in diseases that feature thrombosis or prophylaxis of thrombosis. The LMWH of the present invention is preferably derived from standard heparin by UFH-depolymerization. The LMWHs, are short chains of polysaccharide. LMWHs are defined as heparin or heparin salts having an average molecular weight of between about 2000-10000 Dalton, preferably between 5000 and 8000 Dalton and more preferably about 8000 Dalton, with preferably at least 60% of the chains being less then the average chain length. When the low molecular weight heparin average about 8000 Dalton it is preferred that at least 60% of all chains have a molecular weight less than 8000 Dalton. LMWHs can be obtained by various methods of fractionation or depolymerisation of polymeric heparin. Various methods of heparin depolymerisation are used in the manufacture of low molecular weight heparin. A non-limiting list is given herein below. A heparin of the invention can obtained from a mammal or other organism such as snails, alternatively heparins are synthesized synthetically or semi-synthetically. An example of the latter is production of heparin in bacteria such as but not limited to the heparin K5 by *E. coli*. Modifications of heparin such but not limited to acetylation, desulphatation and phosphorylation are also considered to be a heparin as defined in this invention. Non-limiting but preferred examples of such modifications are completely or partially desulphated LMWH, completely or partially desulphated and completely or partially Re-N-acetylated LMWH, completely or partially desulphated and completely or partially Re-N-sulphated LMWH, Substance L4 or completely or partially desulphated and completely or partially Re-N-phosphorylated LMWH. Preferred are LMWH preparations wherein at least 60% of all chains have a molecular weight less than 8000 Da. These can be obtained by various methods of fractionation or depolymerisation of polymeric heparin. Various methods of heparin depolymerisation are used in the manufacture of low molecular weight heparin. A non-limiting list is given herein below. Oxidative depolymerisation with hydrogen peroxide. Used in the manufacture of ardeparin (Normiflo®). Deaminative cleavage with isoamyl nitrite. Used in the manufacture of certoparin (Sandoparin®). Alkaline beta-eliminative cleavage of the benzyl ester of heparin. Used in the manufacture of enoxaparin (Lovenox® and Clexane®). Oxidative depolymerisation with Cu2+ and hydrogen peroxide. Used in the manufacture of parnaparin (Fluxum®)

Beta-eliminative cleavage by the heparinase enzyme. Used in the manufacture of tinzaparin (Innohep® and Logiparin®). Deaminative cleavage with nitrous acid. Used in the manufacture of dalteparin (Fragmin®), reviparin (Clivarin®) and nadroparin (Fraxiparin®). Step iii of a method of the invention is preferably performed in the absence of LMWH. Preferably a culture medium according to the invention comprises about 1-100, more preferably about 15-50 mg/l of LMWH. The amounts of cytokine added are conventional in the art, preferred amounts are given in the examples, but 10% deviations in amount are very well acceptable and within the scope of the present invention.

Steps ii and iii are performed in the presence of a selected group of cytokines.

For step ii, the collection of cytokines comprises three or more of stem cell factor (SCF), flt-3Ligand (FLT-3L), thrombopoietin (TPO) and interleukin-7 (IL-7) and three or more of granulocyte-macrophage-colony-stimulating factor (GM-CSF), granulocyte-colony-stimulating factor (G-CSF), interleukin-6 (IL-6), leukaemia-inhibitory factor (LIF) and Macrophage-inflammatory protein-1alpha (MIP-I alpha). The amounts of the growth factors used are conventional for SCF, FLT-3L, TPO and IL-7. Typical amounts for cytokines are TPO; 35 ng/ml; FLT-3L; 35 ng/ml, SCF; 35 ng/ml and IL-7; 35 ng/ml. However, lower amounts may be used. For instance, a preferred dosage of the cytokines is TPO; 25 ng/ml; FLT-3L; 25 ng/ml, SCF; 25 ng/ml and IL-7; 25 ng/ml For the GM-CSF, G-CSF, IL-6, LIF and MIP-I alpha a low amount is give, typical amounts are GM-CSF; 10 pg/ml, G-CSF; 250 pg/ml, LIF; 50 pg/ml, MIP-I alpha; 200 pg/ml and IL-6; 50 pg/ml. The cytokines LIF and MIP-I alpha are preferably not present in the cocktail comprising three or more of GM-CSF, G-CSF, IL-6, LIF and MIP-I alpha. In a preferred embodiment, the collection of cytokines in step ii contains SCF, FLT-3L, TPO and IL-7. Preferably the cytokine collection in step ii contains GM-CSF, G-CSF and IL-6.

For step iii the collection of cytokines comprises three or more of SCF, IL-7, interleukin-15 (IL-15) and interleukin-2 (IL-2) and three or more of GM-CSF, G-CSF, IL-6, LIF and MIP-I alpha. The amounts of cytokine added are the same as mentioned for these cytokines in step ii. For IL-15 and IL-2 that are not mentioned in step ii, the amounts are typically as follows: IL-15; 25 ng/ml, IL-2 (Proleukin© [Chiron]; 1000 U/ml). Another preferred amount of IL-15 is 20 ng/ml. Again the cytokines LIF and MIP-I alpha are preferably not present in the cocktail comprising three or more of GM-CSF, G-CSF, IL-6, LIF and MIP-I alpha.

The culture of step (ii) of a method of the invention is preferably performed in a disposable bag for culturing mammalian cells, preferably under static conditions. The disposable bag allows for the culture to be performed in a closed system that is necessary for clinical applications. Step ii is preferably performed under static conditions. It has been found that static conditions are preferred in this stage as this allows good yields of cultured stem cells and progenitor cells or both at the end of step ii. Without being bound by theory it is thought that the static conditions allow the cells to settle and associated with the wall of the disposable bag and to associate with neighbouring cells and that this association favourably affects the yield of the desired cells. Using these conditions for step ii, yielded cell expansions of about 40 (after 7 days) and of about 160 (after 14 days of culture).

The culture of step iii of a method of the invention is preferably performed while the culture medium is mixed during culture, to enhance gas-exchange and to reduce the adherence of cells to a solid surface. It has been observed that static culture of step iii yielded a good number of cells but the cells obtained were relatively impure (i.e. around 70% pure CD56$^+$CD3$^-$ NK cells with a total cell yield at 6 weeks of culture, including step ii, of about 1-2×10E$^9$ cells). This amount and purity is suitable for clinical use but it was surprisingly found that the same total number of cells but a much higher level of purity of CD56$^+$CD3$^-$ NK cells (higher than 90%) could be reached when the same culture was performed as above, but wherein step iii was performed while the culture medium is mixed during culture. It was found that under these conditions the number of mature monocytic cells (i.e. CD14$^+$ and/or CD15$^+$ cells) was greatly reduced. Without being bound by theory it is thought that the presence of these cells and/or the cytokines produced by these cells negatively affects the yield of CD56$^+$CD3$^-$ NK cells. In a preferred embodiment the said culturing of step (iii) is performed under continuous mixing, preferably in a bioreactor for culturing mammalian cells. Various methods for continuous mixing are available in the art. The mixing can for instance be performed with a rotor or with a rocker. The rocker typically rocks the culture periodically. For the present invention such periodic rocking is preferred and is referred to a continuous mixing as the culture is not left static for a time sufficient to allow settling of the cultured cells on the bottom of the culture system.

In one embodiment a method of the invention further comprises as step (iia) culturing cells collected from step (ii) (while the culture medium is mixed during culture, to enhance gas-exchange and to reduce the adherence of cells to a solid surface) at a cell density of at least 0.5×10E$^6$/ml for at least 4 days in a culture medium comprising human serum, a collection of cytokines and low molecular weight heparin, wherein said collection of cytokines comprises three or more of SCF, FLT-3L, Il-15 and IL-7 and three or more of GM-CSF, G-CSF, IL-6, LIF and MIP-I alpha thereby obtaining a collection of cultured stem cells, progenitor cells or both, containing a plurality of progenitor cells committed to the NK cell lineage, said embodiment preferably further comprises culturing said cells in step (iii).

In a preferred embodiment of a method of the invention the cells obtained in step (ii), (iia) or step (iii), are harvested. Preferably the cells obtained in step (iii) are harvested. When cells are harvested from step (ii) or step (iia) any not harvested cells can be cultured further according to the method. If all cells are harvested the method the preferred aspect of further culture is not performed. The harvested cells can be used directly for transplantation purposes. Such transplantation is preferably performed for the treatment of any kind of human disease preferably all malignant diseases such as tumors, cancer, leukemias as well as all viral diseases, also in solid transplant rejection situations and autoimmune diseases and loss of pregnancy.

In a preferred embodiment the harvested cells are washed in a closed system such that culture medium components are diluted at least 500 fold and are replaced by a solution that is compatible with human administration comprising human serum albumin. It is preferred that said solution with which the cells are washed does not contain human serum. It is preferred that the human serum albumin present in the solution is derived from a batch comprising essentially pure human serum albumin. In a preferred embodiment said human serum albumin is recombinantly produced human serum albumin. In a preferred embodiment said solution comprises between 0.3% and 10% human serum albumin. Preferably said solution comprises between 0.5 and 5% humans serum albumin. It has been observed that cells treated in the above way and are collected in the solution that is compatible with human administration and that comprises human serum albumin can be stored for a prolonged period of time under these conditions without detrimental loss of viability and/or activity. The solution wherein the cells are stored is further also referred to as "storage solution". The storage solution preferably comprises less than 0.1% human serum, preferably said storage solution does not comprise human serum. In a preferred embodiment said storage solution comprises human serum derived from a batch comprising essentially pure human serum albumin. In a preferred embodiment said human serum albumin is recombinantly produced human serum albumin. In a preferred embodiment said storage solution comprises between 0.3% and 10% human serum albumin. Preferably said storage solution comprises between 0.5 and 5% humans serum albumin. Preferred solutions compatible with human administration are preferably PBS or physiological salt solutions. The PBS or physiological salt solution may contain one or more additives. In one embodiment the additive is human serum albumin. In a preferred embodiment the compatible solution is physiological salt solution. Harvested cells are preferably stored for at least one day at a temperature of between room temperature and 0° C., preferably said harvested cells are stored for 1, 2 or 3 days at said temperature. Preferably said solution that is compatible with human administration is a physiological salt solution. The physiological salt solution is typically though not necessarily 0.9% NaCl.

In a preferred embodiment harvested and/or stored cells are divided into at least 5 portions and stored at a temperature below −70° C.

The invention further provides a disposable bag for culturing mammalian cells comprising a culture medium comprising a collection of cultured stem cells, progenitor cells or both, from human postembryonic tissue containing a plurality of progenitor cells committed to the NK cell lineage. Preferably said culture medium comprises human serum, a collection of cytokines and low molecular weight heparin, wherein said collection of cytokines comprises three or more of SCF, FLT-3L, TPO and IL-7 and three or more of GM-CSF, G-CSF, IL-6, LIF and MIP-I alpha. Such bags are used in a method of the invention.

In a further aspect the invention provides a bioreactor for culturing mammalian cells comprising a culture medium and a collection of cultured cells derived from stem cells, progenitor cells or both from human postembryonic tissue, containing a plurality of NK cells or NK progenitor cells or both. Preferably said culture medium further comprises human serum and a collection of cytokines, wherein said collection of cytokines comprises three or more of SCF, IL-7, IL-15 and IL-2 and three or more of GM-CSF, G-CSF, IL-6, LIF and MIP-I alpha. Such a bioreactor is used in a method of the invention.

Nk-progenitor cells are often referred to as NKP and immature NK cells and typically comprise the cellular markers IL-2Rbeta and/or NKR-P1 and CD2.

The invention further provides an in vitro collection of harvested cultured cells derived from a culture of stem cells, progenitor cells or both from human postembryonic tissue, containing a plurality of NK cells or NK progenitor cells or both. The collection preferably comprises more than 50% CD56 positive, CD94 positive cells and/or CD56 positive, CD94 negative cells, preferably said cells are negative for CD117 and CD34. In a preferred embodiment said cells have been stored for at least 1 day at a temperature of between room temperature and 0° C., preferably said collection has been stored for 1, 2 or 3 days at said temperature. In a preferred embodiment said plurality of NK-cells or NK progenitor cells or both comprise at least 70% viable NK-cells or NK progenitor cells or both, preferably as determined by 7AAD exclusion. Preferably said collection is essentially free of CD3+ T cells. In a preferred embodiment said collection of harvested cultured cells are stored in a solution that is compatible with human administration comprising human serum albumin.

Cultured cells can be harvested at any time after one week of culture. The harvested cultures are unique in that they contain NK cells or progenitors thereof that are not detected in vivo or in purified stem and progenitor cells. They are further unique in that they contain mixtures of cell populations that are not detected in vivo or in purified cultures in the specific ratio's detected. Table 9 depicts the cellular marker profile of various cell populations detected in the in vitro culture. The cell populations are characterized by the presence of marker proteins on the surface of the cells. The cells are defined as CD45+/CD3− lymphocytes and further characterized for the markers CD133, CD34, CD117, CD244, CD33, CD56, CD94 and CD159a. The cell types are ordered into 7 different developmental stages (1, 2, 3a, 3b, 4, 5a and 5b). Within each stage different subsets are identified (indicated with a capital letter). Table 10 shows the relative contribution of the subsets of each stage to the total cell population in said stage. Table 11 shows the relative contribution of each subset to the total number of cells detected in the sample of CD45+/CD3− lymphocytes. From each tissue 5 different donors were tested and if cell populations contained more than 0.01% of total cells and more than 50 cells total and appeared in at least 3 of 5 donors their were seen as a faithful stage or subset. For the cell cultures 4 different donors were analysed and if 2 from 4 donors show a cell population of more than 0.01% of total cells and more than 50 cells total the stage or subset was seen as faithful.

The harvested cells or cells fractions purified from the harvested cells can be used for immunotherapy or transplantation purposes. For instance cells harvested after step (ii) or (iia) are versatile cells that can produce a variety of NK cells in vivo. They can be differentiated either in cytotoxic NK cells or immunoregulatory cells, that can be either used for anti tumor therapy or against infectious diseases or used for the treatment of autoimmune diseases. The transplanted cells can also be induced or stimulated in a certain direction by providing the recipient with appropriate growth factors such as IL-15, IL-2, IL-7, IL-12, IL-18, IL-21, IL-23, IL-17, IL1-β or IL-10. Collected after step (iii) are typically more differentiated when compared to step (ii) or step (iia) cells. The harvested cells containing the unique cell types can be used directly or the desired subset(s) can be purified from the harvested cells. Thus the invention further provides a collection of harvested cultured cells comprising at least a cell population having the cell marker profile of subset E from stage 3a, subset M or subset B from stage 3b, subset K or subset M from stage 4, or subset B from stage 5b. Cells with these cellular marker profiles are not present in detectable numbers in the respective isolated tissues and/or purified tissues, but are formed in the ex-vivo culture of a method of the invention.

Preferably said collection of harvested cultured cells obtainable by a method of the invention contains at least 0.5% cells with the cell marker profile of subset E from stage 3a. Preferably between 0.5 to 10%, more preferably between 2 to 8% and in a particularly preferred embodiment between 3 to 6% cells with the marker profile of subset E from stage 3b.

Preferably said collection of harvested cultured cells obtainable by a method of the invention contains at least 0.5% cells with the cell marker profile of subset M from stage 3b. Preferably between 0.5 to 10%, more preferably between 0.5 to 6% and in a particularly preferred embodiment between 1.5 to 6% cells with the marker profile of subset M from stage 3b.

Preferably said collection of harvested cultured cells obtainable by a method of the invention contains at least 0.1% cells with the cell marker profile of subset B from stage 3b. Preferably between 0.1 to 10%, more preferably between 0.1 to 4% and in a particularly preferred embodiment between 0.5 to 2.5% cells with the marker profile of subset B from stage 3b.

Preferably said collection of harvested cultured cells obtainable by a method of the invention contains at least 0.5% cells with the cell marker profile of subset K from stage 4. Preferably between 0.5 to 10%, more preferably between 0.5 to 6% and in a particularly preferred embodiment between 2 to 6% cells with the marker profile of subset K from stage 4.

Preferably said collection of harvested cultured cells obtainable by a method of the invention contains at least 0.5% cells with the cell marker profile of subset M from stage 4. Preferably between 0.5 to 8%, more preferably between 0.5 to 6% and in a particularly preferred embodiment between 1.0 to 4% cells with the marker profile of subset M from stage 4.

Preferably said collection of harvested cultured cells obtainable by a method of the invention contains at least 0.1% cells with the cell marker profile of subset B from stage 5b. Preferably between 0.5 to 10%, more preferably between 0.5 to 6% and in a particularly preferred embodiment between 1.0 to 6% cells with the marker profile of subset B from stage 5b.

The cellular marker profiles of the respective populations is given in Table 9 and indicated herein below.

Stage 3a E: CD133+ CD34− CD117+ CD244+ CD33+ CD56− CD94− CD159a− CD45+ CD3−
Stage 3b B: CD133− CD34− CD117+ CD244+ CD33+ CD56+ CD94− CD159a+ CD45+ CD3−
Stage 3b M: CD133− CD34− CD117+ CD244+ CD33− CD56+ CD94− CD159a− CD45+ CD3−
Stage 4 K: CD133− CD34− CD117+ CD244+ CD33+ CD56+ CD94+ CD159a− CD45+ CD3−
Stage 4 M: CD133− CD34− CD117+ CD244+ CD33− CD56+ CD94+ CD159a− CD45+ CD3−
Stage 5b B: CD133− CD34− CD117− CD244+ CD33+ CD56+ CD94− CD159a+ CD45+ CD3−

The invention further provides a collection of cultured cells obtainable by a method of the invention comprising between
  1-10% cells with a cellular marker profile of stage 1 of table 9,
  2-15% cells with a cellular marker profile of stage 2 of table 9, and
  50-97% cells with a cellular marker profile of stage 3a of table 9.

Preferably said collection comprises between
  2-8% cells with a cellular marker profile of stage 1 of table 9,
  3-15% cells with a cellular marker profile of stage 2 of table 9, and
  65-95% cells with a cellular marker profile of stage 3a of table 9.

The invention further provides a collection of cultured cells obtainable by a method of the invention comprising between
  1-10% cells with a cellular marker profile of stage 1 of table 9, 2-15% cells with a cellular marker profile of stage 2 of table 9, or
50-97% cells with a cellular marker profile of stage 3a of table 9.

Preferably said collection comprises between
2-8% cells with a cellular marker profile of stage 1 of table 9,
3-15% cells with a cellular marker profile of stage 2 of table 9, or
65-95% cells with a cellular marker profile of stage 3a of table 9.

The above mentioned collection may among others be transplanted in a recipient in need thereof, stored according to a method of the invention, or cultured in step (iia) and/or step (iii) of a method of the invention. The invention thereto further provides a disposable bag for culturing mammalian cells comprising a collection of cells as defined herein. The invention further provides a bioreactor for culturing mammalian cells comprising a collection of cells as defined herein.

The invention further provides a collection of cultured cells obtainable from step (ii) and/or step (iia) of a method of the invention comprising between
1-10% cells with a cellular marker profile of stage 1 of table 9,
2-15% cells with a cellular marker profile of stage 2 of table 9, and
50-97% cells with a cellular marker profile of stage 3a of table 9.

Preferably said collection comprises between
2-8% cells with a cellular marker profile of stage 1 of table 9,
3-15% cells with a cellular marker profile of stage 2 of table 9, and
65-95% cells with a cellular marker profile of stage 3a of table 9.

The invention further provides a collection of cultured cells obtainable from step (ii) and/or step (iia) of a method of the invention comprising between
1-10% cells with a cellular marker profile of stage 1 of table 9,
2-15% cells with a cellular marker profile of stage 2 of table 9, or
50-97% cells with a cellular marker profile of stage 3a of table 9.

Preferably said collection comprises between
2-8% cells with a cellular marker profile of stage 1 of table 9,
3-15% cells with a cellular marker profile of stage 2 of table 9, or
65-95% cells with a cellular marker profile of stage 3a of table 9.

The invention further provides a collection of cultured cells obtainable from step (iii) of a method of the invention comprising between
15-30% cells with a cellular marker profile of stage 3a of table 9,
2-8% cells with a cellular marker profile of stage 3b of table 9,
5-20% cells with a cellular marker profile of stage 4 of table 9,
1-5% cells with a cellular marker profile of stage 5a of table 9, and
0.1-1.5% cells with a cellular marker profile of stage 5b of table 9.

Preferably said collection comprises between
18-26% cells with a cellular marker profile of stage 3a of table 9,
3-7% cells with a cellular marker profile of stage 3b of table 9,
8-17% cells with a cellular marker profile of stage 4 of table 9,
1.5-3.5% cells with a cellular marker profile of stage 5a of table 9, and
0.2-1.0% cells with a cellular marker profile of stage 5b of table 9.

The invention further provides a collection of cultured cells obtainable from step (iii) of a method of the invention comprising between
0.2-4% cells with a cellular marker profile of stage 3a of table 9,
6-16% cells with a cellular marker profile of stage 3b of table 9,
35-75% cells with a cellular marker profile of stage 4 of table 9,
12-24% cells with a cellular marker profile of stage 5a of table 9, and
0.2-3% cells with a cellular marker profile of stage 5b of table 9.

Preferably said collection comprises between
0.4-2.5% cells with a cellular marker profile of stage 3a of table 9,
8-13% cells with a cellular marker profile of stage 3b of table 9,
45-65% cells with a cellular marker profile of stage 4 of table 9,
14-22% cells with a cellular marker profile of stage 5a of table 9, and
0.5-2.5% cells with a cellular marker profile of stage 5b of table 9.

The invention further provides a collection of cultured cells obtainable from step (iii) of a method of the invention comprising between
0.2-4% cells with a cellular marker profile of stage 3a of table 9,
7-21% cells with a cellular marker profile of stage 3b of table 9,
35-78% cells with a cellular marker profile of stage 4 of table 9,
9-21% cells with a cellular marker profile of stage 5a of table 9, and
1-9% cells with a cellular marker profile of stage 5b of table 9.

Preferably said collection comprises between
0.3-1.0% cells with a cellular marker profile of stage 3a of table 9,
11-18% cells with a cellular marker profile of stage 3b of table 9,
45-68% cells with a cellular marker profile of stage 4 of table 9,
11-18% cells with a cellular marker profile of stage 5a of table 9, and
2.5-8.5% cells with a cellular marker profile of stage 5b of table 9.

The percentage of cells with a cellular marker profile of a certain stage preferably at least contains the cells with most abundant cellular marker profile of the indicated stage for the in vitro cultured cells of table 11. Preferably said percentage, comprises all of the cell populations with a listed cellular marker profile for said stage in the in vitro culture as depicted in table 11.

The above mentioned collection may among others be transplanted in a recipient in need thereof, stored according to a method of the invention, or cultured in step (iii) of a method of the invention.

The collections of cells as mentioned herein may contain cells with a cellular marker profile different for the one(s) specified. For instance, the collection harvested at w3 time point contains, in addition, to the mentioned cell populations also cells that have different cellular markers.

The cells can be obtained by harvesting the cultured cells at the indicated time point or at a different time point within the period specified. The cells can be used directly or the desired cell population can be purified from said harvested cells. One of the uses is the transplantation of the collected cells. The cells may be transplanted systemically, for instance, through intravenous injection, or transplanted locally, for instance, via injection in a certain body compartment such as the peritoneum, or locally into for instance a tumor.

Stage 1 is commonly present in bone marrow (BM) and during the early phases of ex-vivo NK cell generation from CD34 positive cells. Stage 1 compromises subsets of G, N, L, P, F from which G, N are specific for BM tissue and L, P, F could be found in enriched CD34+ cells from umbilical cord blood (CB). Furthermore CB has exclusively E, K, M subsets in stage 1 and E, K subsets are present at week 1 and 2 of NK cell generation. Cells harvested at the w1 or w2 time point are suitable for continued culture in step (ii) or step (iia) or step (iii) of a method of the invention. The cells can also be transplanted into an individual in need thereof. For instance, cells harvested at the w2 time point can be transplanted, and differentiated in vivo be enhanced by the infusion of IL-2 or Il-15 or both and/or in combination with IL-12, IL-18 or IL21 or a combination thereof. Furthermore the differentiation into other lineage such as dentritic cells, DCs, T-cells, B cells or cells of the myeloid lineage could be achieved with modified culture protocols.

Stage 2 is commonly present in bone marrow (BM) and during the early phases of ex-vivo NK cell generation. Stage 2 compromises subsets of G, E, L, P and F from which P is specific for BM tissue and E, L, F, G could be found in enriched CD34+ cells from umbilical cord blood (CB). Furthermore CB has exclusively K, N subsets in stage 2. BM and CB share a central subset E in stage 2 and this remains for at least 3 weeks of culture. CB at day 0 has more exclusive K, N subsets from which K is present at week 1 and 2 during NK cell generation. Stage 2 cells are found also in CB tissue and share a central subset E with ex-vivo expanded CB cells during 3 weeks of culture. The cells from ex-vivo culture show an exclusive subset K also after week 1 and 2 of culture.

Cells harvested at the w1 or w2 time point are suitable for continued culture in step (ii) or step (iia) or step (iii) of a method of the invention. The cells can also be transplanted into an individual in need thereof. For instance, cells harvested at the w2 time point can be transplanted, and differentiated in vivo be enhanced by the infusion of IL-2 or Il-15 or both and/or in combination with IL-12, IL-18 or IL21 or a combination thereof. Immunoregulatory NK cells NK-22 (NK cells producing IL-22) could be cultured with the addition of IL-1β and IL-23. Furthermore the differentiation into other lineage such as dentritic cells (DCs), T-cells, B cells or cells of the myeloid lineage could be achieved with modified culture protocols.

Stage 3a cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, N, J, O and P could be identified. O is found only in SPL and BM whereas J is additionally also found in inLN and LiLN. BM, CB and PB share a central subset K, which is also present during 5 weeks of NK cell development. SPL, inLN and LiLN share the central P subset and in LiLN also the N subset is central. Where the K subset is central in BM, CB and PB, it is exclusive for ex-vivo cultures compared to SPL, inLN and LiLN.

Ex-vivo cultures have exclusive subsets E, M compared with BM for week 1-3 and share P in the 1st week of culture and N subset for week 1-3.

Ex-vivo cultures have an exclusive subset E compared with CB in week 1-3 and share subsets M, N, P in week 1-3.

Ex-vivo cultures have exclusive subsets E, M, N compared with PB in week 1-3 and share subset P in week 1-3.

Ex-vivo cultures have exclusive subsets E, M, N, K compared with SPL in week 1-3 and subset K in week 4+5.

Ex-vivo cultures have exclusive subsets E, M, N, K compared with inLN in week 1-3 and subset K in week 4+5.

Ex-vivo cultures have exclusive subsets E, M, K compared with LiLN in week 1-3 and subset K in week 4+5.

Thus there are NK cell restricted progenitors present during the whole culture process week 1-5. The cells of stage 3a are more tissue specific than progenitors from earlier stages of culture. The correlation of the marker profile of the cells in the ex vivo culture with the marker profile of subsets of NK-cells or progenitors thereof in tissues, indicates that the cells will preferably home to the tissues that they share a marker profile with. Together with in-vivo NK cell maturation by infusion of IL-2 or Il-15 or both and/or in combination with IL-12, IL-18 or IL21 or a combination thereof. Immunoregulatory NK cells NK-22 (NK cells producing IL-22) could be cultured with the addition of IL-1β and IL-23. These NK cells can be educated locally to kill the cancer cells. Stage 3a cells and subset are ideal for NK cell lineage specific manipulation by GAGs, heparins cytokines, or other proteins.

Stage 3b cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, N, J, B and P could be identified. No tissue specific subset was found. BM and CB share a central subset K, which is also present during 3 weeks of NK cell differentiation (week 3-5). PB, SPL, inLN and LiLN share the central J subset.

Ex-vivo cultures have exclusive subsets B, M, N, P compared with BM for week 3, B, M, N for week 4 and share J in the 3rd and 4th week of culture. B, M subsets are exclusively seen in week 5 of ex-vivo cultures.

Ex-vivo cultures have exclusive subsets B, M, N, J, P compared with CB for week 3, B, M, N and J for week 4 of culture. B, M subsets are exclusively seen in week 5 of ex-vivo cultures.

Ex-vivo cultures have exclusive subsets B, M, N, K, P compared with PB for week 3, B, M, N and K for week 4 of culture. B, M, K subsets are exclusively seen in week 5 of ex-vivo cultures.

Ex-vivo cultures have exclusive subsets B, M, N, K, P compared with SPL for week 3, B, M, N and K for week 4 of culture. B, M, K subsets are exclusively seen in week 5 of ex-vivo cultures.

Ex-vivo cultures have exclusive subsets B, M, N, K compared with inLN for week 3, and 4 and P subset is shared in the 4th week of culture. B, M, K subsets are exclusively seen in week 5 of ex-vivo cultures.

Ex-vivo cultures have exclusive subsets B, M, K, P compared with LiLN for week 3, B, M, K for week 4 and share N in the 3rd and 4th week of culture. B, M, K subsets are exclusively seen in week 5 of ex-vivo cultures.

The main subsets of stage 3b are the central subsets specific for a tissue and additionally there are some tissue specific subsets J for BM and p for inLN and N for LiLN. These subsets can be used for the treatment of lymphomas, liver cancer or infections like hepatitis or multiple myeloma or other hematological cancers. In a preferred embodiment the treatment further comprises in-vivo NK cell maturation by infusion of IL-2 or Il-15 or both and/or in combination with IL-12, IL-18 or IL21 or a combination thereof. Immunoregulatory NK cells NK-22 (NK cells producing IL-22) could be cultured with the addition of IL-1β and IL-23. These NK cells can be educated locally to kill the cancer cells. Stage 3b cells and subsets thereof are very well suited for NK cell lineage specific manipulation by GAGs, heparins cytokines, or other proteins.

Stage 4 cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, J and B could be identified. No tissue specific subset was found. BM, PB and LiLN share central subsets J, B which are present during 3 weeks of NK cell differentiation (week 3-5). CB, SPL and inLN share the central J subset. Ex-vivo cultures have exclusive subsets K, M, compared with BM, PB and LiLN for week 4+5. B, K, M subsets are exclusively seen in week 4+5 of ex-vivo cultures compared to CB, SPL and inLN. In stage 4 cell populations and subsets are detected that also occur in tissues and the ex-vivo cultures. The main subsets are the central subsets J or B that occur in-vivo and ex-vivo. Stage 4 and subsets are more universal NK cells products to treat various cancers or infections. The treatment preferably further comprises in-vivo NK cell maturation by infusion of IL-2 or Il-15 or both and/or in combination with IL-12, IL-18 or IL21 or a combination thereof. These NK cells can be educated locally to kill the cancer cells. Stage 4 cells and subsets are a target for NK cell lineage specific manipulation by GAGs, heparins cytokines, or other proteins.

Stage 5a cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, J, B could be identified. No tissue specific subset was found. BM, PB, inLN and LiLN share central subsets J, B which are present during 3 weeks of NK cell differentiation (week 3-5). In CB and SPL share the central J subset compared to week 3-5 of culture. Ex-vivo cultures have exclusive subset K compared with BM, inLN and LiLN during 4th and 5th week of culture. M subset is shared in week 5 of ex-vivo cultures.

Ex-vivo cultures have an exclusive subset B in the 3rd week of culture compared with CB and SPL and further exclusive subsets K, B during 4th and 5th week of culture. M subset is shared in week 5 of ex-vivo cultures.

Ex-vivo cultures subset subsets K compared with PB in the 4th week and share subsets K, M during the 5th week of culture.

Stage 5a in the in vitro culture exhibits similar subsets as those detected in the peripheral blood (PB). The main subsets are the central subsets J or B that occur as well in in-vivo as in ex-vivo. Stage 5a and subsets are more mature and cytotoxic NK cells but also cytokine producers. The cells may be transplanted directed into the recipient in need thereof to kill virus infected cells or cancer cells. The recipient may further be treated in-vivo with specific NK cell activation infusion of IL-2 or Il-15 or both and/or in combination with IL-12, IL-18 or IL21 or a combination thereof. These NK cells can be educated locally to kill the cancer or the pathogen infected cells. Stage 5a cells and subset are a target for NK cell lineage specific manipulation by GAGs, heparins cytokines, or other proteins. The treatment may further comprise combinational therapy with antibodies to target NK cells or block activating or inhibitory receptors. Additionally modifications of NK cell therapy by using immunomodulatory drugs or other chemotherapeutic agents to increase the NK cell function can also be used in conjunction with transplantation of stage 5a cells. Administration routes encompass the intravenous route or injections at a local site.

Stage 5b cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, J, B, P, N could be identified. Tissue specific subsets as P, N in PB and P in inLN were found. BM, CB, PB, SPL, inLN and LiLN share a central main subset M, which is present during 3 weeks of NK cell differentiation (week 3-5). In BM, CB and PB they share additionally the central small subset K compared to week 3-5 of culture. Ex-vivo cultures have exclusive subset B compared with BM, CB and PB during 3rd and 5th week of culture. J subset is shared in week 4+5 of ex-vivo cultures. Ex-vivo cultures have exclusive subsets B, K compared with SPL, inLN and LiLN 3rd and 5th week of culture. J subset is shared in week 4+5 of ex-vivo cultures. Stage 5b is characterised by a prevalence of mature NK cells, although in vitro cultured cells are also cytolytic at earlier culture stages. In week 3+4 the same main subsets in the ex-vivo cultures are shared or central as in all tissues. The main subsets are the central subsets J or M that occur as well in in-vivo as in ex-vivo, whereas ex-vivo has also major B, K subsets in a more or less exclusive way. Stage 5b cells and subsets are more mature and cytotoxic NK cells but also contain cytokine producers. The cells are suitable for transplantation into the individual in need thereof. Preferably the treatment further comprises in-vivo specific NK cell activation infusion of IL-2 or Il-15 or both and/or in combination with IL-12, IL-18 or IL21 or a combination thereof. These NK cells can be educated locally to kill the cancer cells or the pathogen infected cells. Stage 5b cells and subset can be a target for NK cell lineage specific manipulation by GAGs, heparins cytokines, or other proteins. Furthermore, the treatment may further comprise the combinational therapy with antibodies to target NK cells or block activating or inhibitory receptors. Additionally modifications of NK cell therapy by using immunomodulatory drugs or other chemotherapeutic agents to increase the NK cell function can also be used together with transplantation of stage 5b cells. The administration routes encompass among others the intravenous route but also injections at a local site as route for NK cell administration.

The invention further provides a collection of storage containers for mammalian cells, wherein each of said storage containers contains cells derived from a culture of stem cells, progenitor cells or both, from human postembryonic tissue containing a plurality of NK cells or NK progenitor cells or both, obtainable by a method of the invention. In a preferred embodiment said collection of storage containers comprises at least 5 containers that each contains at least $4 \times 10E^8$ NK cells or NK progenitor cells or both. In a preferred embodiment said NK cells and/or NK progenitor cells comprise cell surface markers as indicated herein. In a preferred embodiment said containers comprise harvested cells from a culture that was initiated by cells from a single source, i.e. a single human individual. Typically such cells are genetically identical. This has the advantage that quality control can be performed on a separate sample. Furthermore, storage in separate containers allows for sequential administration of the graft to a human in need thereof. If the individual responds well the administration of a graft, a subsequent graft can be selected having the same properties as the graft that the individual had already been treated with. To this end the invention further provides a cell bank comprising a collection of cultured cells derived from a culture of stem cells, progenitor cells or both from human postembryonic tissue, containing a plurality of NK cells or NK progenitor cells or both, obtainable by a method of the invention or comprising a collection of storage containers according to the invention.

The invention further provides a method of the invention further comprising obtaining a cell sample of said culture of step (ii), step (iia) and/or step (iii) and determining stages of NK development in cells of said culture. Preferably the culture of step (ii), step (iia) or step (iii) is terminated on the basis of a detected developmental stage in said sample.

The invention further provides a collection of harvested cultured cells derived from a culture of stem cells, progenitor cells or both from human postembryonic tissue obtained from one human individual, containing a plurality of NK cells or NK progenitor cells or both, that has been stored for at least 1 day at a temperature of between room temperature and 0° C., wherein said plurality of NK cells or NK progenitor cells or both comprises at least 70% viable NK cells or NK progenitor cells or both, as determined by 7AAD exclusion. During clinical application of the collection of harvested cultured cells, as a quality measurement, the viability of the cells is measured. It is preferred to have a high percentage of viable NK cells or NK progenitor cells or both in the collection of harvested cultured cells which are transfused to a patient.

In one embodiment, therefore, a collection of harvested cultured cells derived from a culture of stem cells, progenitor cells or both from human postembryonic tissue obtained from one human individual, containing a plurality of NK cells or NK progenitor cells or both, that has been stored for at least 1 day at a temperature of between room temperature and 0° C., wherein said plurality of NK cells or NK progenitor cells or both comprises at least 70% viable NK cells or NK progenitor cells or both, as determined by 7AAD exclusion.

It is preferred, especially when NK cells are transfused to another individual as the individual from which the stem or progenitor cells were harvested, that the collection is essentially free of CD3+ T cells. CD3+ T cells can induce life threatening conditions, such as Graft versus Host disease. In a preferred embodiment, therefore, a collection of harvested cultured cells according to the invention is provided, wherein the collection is essentially free of CD3+ T cells.

NK cells or progenitor cells thereof have different properties depending on the developmental stage of the NK-cells or the progenitor. The fact that a culture system as provided by the invention provides NK cells and progenitors thereof at various developmental stages can be used to tailor a graft to the specific need of the individual to be treated with the graft. For instance it has been found in the present invention that certain stages have a different homing preference in vivo. This preference of different developmental stages is used in the present invention to provide grafts that are tailored to the specific disease to be treated. A developmental stage of NK cells or progenitor cells, as each developmental stage can be applied in a different clinical setting. Such developmental stage can be determined by several surface markers of NK cell or NK progenitor cells. The present invention has established that at least 7 different developmental stages can be distinguished in NK-cells and progenitors thereof. To this end the invention provides a method for determining a developmental stage of NK development, said method comprising obtaining a cell sample of said culture of step (ii), step (iia) and/or step (iii), determining four or more of the cell surface markers CD133, CD34, CD117, CD244, CD45, CD33, CD3, CD56, CD94, CD159a, CD2, CD7, CD10, CD18, CD11a, LFA-1, CD122 and CD45RA, wherein the expression of a combination of said cell surface markers is indicative for said developmental stage, and determine a developmental stage of NK cells present in said sample.

Preferred markers for said stages are CD34, CD117, CD56 and CD94. The combination of CD34, CD117, CD56 and CD94 is very useful in determining the developmental stage of NK cells or NK progenitor cells. Now that the invention has shown that these 7 developmental stage exist also other markers can be used to identify the detected developmental stages. In a preferred embodiment, the invention provides a method according to the invention, wherein said developmental stage of NK development is classified as stage 1, 2, 3a, 3b, 4, 5a, and 5b by measuring the expression of surface markers CD34, CD117, CD56, and CD94, wherein stage 1 is characterized by cells having the expression profile CD34 positive, CD117 negative, CD56 negative, CD94 negative, stage 2 is characterized by cells having the expression profile CD34 positive, CD117 positive, CD56 negative, CD94 negative, stage 3a is characterized by cells having the expression profile CD34 negative, CD117 positive, CD56 negative, CD94 negative, stage 3b is characterized by cells having the expression profile CD34 negative, CD117 positive, CD56 positive, CD94 negative, stage 4 is characterized by cells having the expression profile CD34 negative, CD117 positive, CD56 positive, CD94 positive, stage 5a is characterized by cells having the expression profile CD34 negative, CD117 negative, CD56 positive, CD94 positive, stage 5b is characterized by cells having the expression profile CD34 negative, CD117 negative, CD56 positive, CD94 negative.

Additional markers can be used, such as CD133, CD33, CD244 or NKG2A, to confirm the determined development stage by a method according to the invention. In a preferred embodiment, therefore, a method according to the invention is provided, further comprising measuring expression of CD133, CD33, CD244, and NKG2A, wherein stage 1 is further characterized by cells negative for CD33, CD244, and NKG2A expression, stage 2 is further characterized by cells negative for NKG2A expression, stage 3a is further characterized by cells negative for CD133 and NKG2A expression, stage 3b is further characterized by cells negative for CD133, CD33, and NKG2A expression, stages 4, 5a and 5b are further characterized by cells negative for CD133 and CD33 expression.

The present invention describes the successful translational process to implement a highly efficient cell culture protocol for the generation of functional and pure NK cell products from UCB-derived hematopoietic stem and precursor cells into a clinical applicable GMP procedure. We have reported about a culture method for the ex vivo generation of functional NK cells for clinical application in the treatment of patients with AML and other malignancies [17]. This cytokine based, stroma-free culture process uses only human recombinant proteins. The process has been translated into a GMP compliant version starting with an efficient clinical grade enrichment of CD34+ cells from cryopreserved UCB. Furthermore we generated a UCB-NK cell therapy product using a closed production process optimized for NK cell differentiation using bioreactors. We additionally demonstrate, that the cell culture process is safe and that the product could be further processed, stored and safely released for patients.

A clinical grade selection process for CD34+ cell from UCB is typically required to translate the process into a GMP setting. Several studies so far reported about the closed system immunomagnetic selection of CD34+ cells from cryopreserved UCB [20-23]. Most of the studies used the ISOLEX300I™ or the CLINIMACS® system, but up to date only the CLINIMACS® system is still available for clinical application. Due to technical modifications such as different tubing sets for the CLINIMACS® (tubing 150 in older studies and tubing 161-01 in this study) and differences in the cord blood processing prior cryopreservation (use of different anticoagulants or methods for volume reduction and removal for red blood cells) one may expect variations for the efficiency of the selection procedure. The influence of different methods of volume reduction and removal of red blood cells on the recovery of CD34+ has widely been studied [24-27] and we used a well-established method in our study [28]. Studies about different selection methods for CD34+ cells showed a median recovery of 31% (n=10)[23] and 31% (n=11)[20] using the CLINIMACS® device. In contrast we found a higher overall median CD34+ recovery of 50% (n=16) compared to the volume reduced cord blood and 73% (n=16) regarding the thawed UCB. This shows that we used a powerful thawing procedure which provided good basis for a superior CD34+ selection compared to previous studies. Querol et al.[21] used a similar thawing procedure with Pulmozyme on HES treated cord blood units, however they used the Isolex-300-SA for CD34 selection. They used a similar cord blood cohort with $1.11\pm0.5\times10^9$ nucleated cells (NCs) and $3.64\pm2.54\times10^6$ CD34+ cells compared to ours with $1.08\pm0.4\times10^9$ NCs and $3.78\pm1.95\times10^6$ CD34+ cells. They isolated $1.94\pm1.55\times10^6$ CD34+ cells with a purity of 69%±16% and a recovery of 52%±12% compared to the population before cryopreservation. Using an up-to-date CLINIMACS® system, we isolated CD34+ cell numbers of $1.96\pm1.27\times10^6$ cells with a purity of 67%±14% and a recovery of 53%±15%, similar to the described study. We demonstrated with current thawing and CD34+ selection procedures that a sufficient preparation of a CD34+ cell product for direct use or graft manipulation is feasible.

We further investigated, if these clinical selected stem and progenitor cell product could be efficiently expanded and further differentiated in a closed cell culture system. The combination of static bags during the expansion phase and the use of bioreactors for the differentiation process allowed the generation of a viable, pure and functional UCB-NK cell product for cellular therapy. The Wave™ or Biostat™ bioreactor systems have the advantage, that the CO2 mixture is provided as headspace in the bag and the rocking of the bag should mediate a better gas exchange compared to static bag culture systems. Therefore, the NK cell differentiation process seemed to be more optimal under these conditions.

Additionally, we performed several tests on the end product to describe the product release criteria for the UCB-NK cell therapy product (summarized in Table 4). The genetic stability was controlled by karyotype analysis and showed no abnormalities after 6 weeks of cultures. The products were always negative for bacterial, fungal or mycoplasm contamination. After washing of the product, the volume was reduced from 1 liter to 150 ml prior infusion. Cytokine levels were <25 pg/ml and immunophenotyping described the purity, viability and phenotype of the product and show the absence of T-cells.

Summing up, we adapted our method into a closed-system bioprocess for production of allogeneic NK cell batches under GMP conditions, in order to utilize ex vivo-expanded NK cells for adoptive immunotherapy in poor-prognosis AML patients. Large-scale experiments using gas-permeable culture bags and up-scaling of the NK cell expansion step into the bioreactor systems resulted in the generation of more than $3.5\times10^9$ NK cell products with a purity of up to 95%. Furthermore, the UCB-NK-cell products could be finally processed for infusion using a closed system and be stored until all product control tests will be available in order to release the UCB-NK-cell therapy product.

Importantly, most recently we got approval from the Dutch authorities ("Centrale Commissie Mensgebonden Onderzoek" (CCMO)) to run a phase I/II trial using these allogeneic UCB-NK cell therapy products. The NK cell products will be administered to the patients intravenously using dose escalation of $3\times10^6$, $10\times10^6$, $3\times10^7$ and $10\times10^7$ NK cells per kg body weight in cohorts of three patients. The primary aim of this phase I dose escalation study is to evaluate safety and toxicity of ex vivo-expanded NK cell infusions following a lymphocytes depleting chemotherapy regimen. Secondary objectives are to evaluate the in vivo lifespan of infused NK cell products and effects on residual disease.

Degranulation of ex vivo-generated NK cells against K562 was analyzed by CD107a expression after 18 hours of co-culture after of unwashed (black bars) and washed (white bars) NK cells from three different donors at an E:T ratio of 1:1.

Figure 3A:
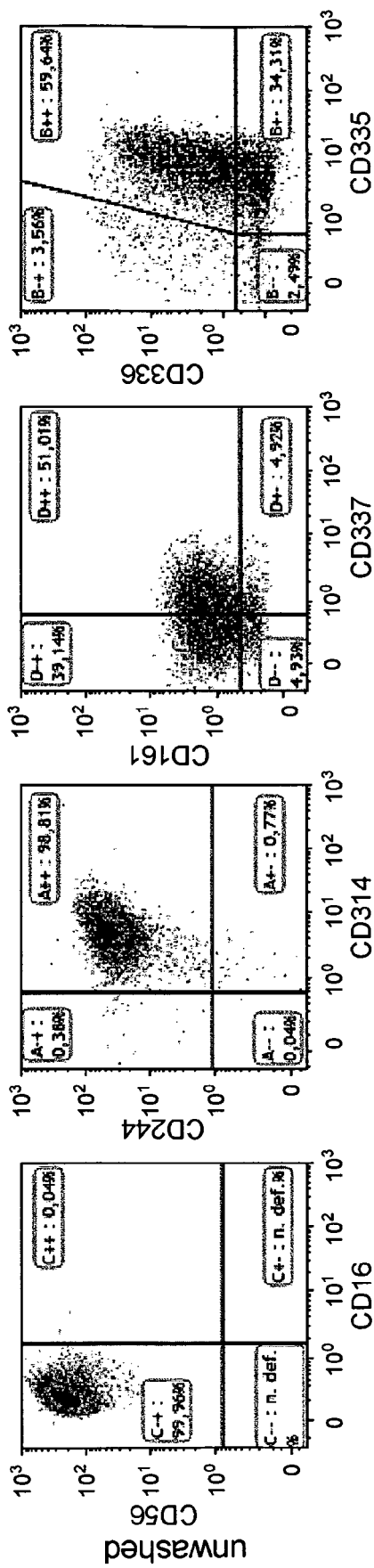
Figure 3B:
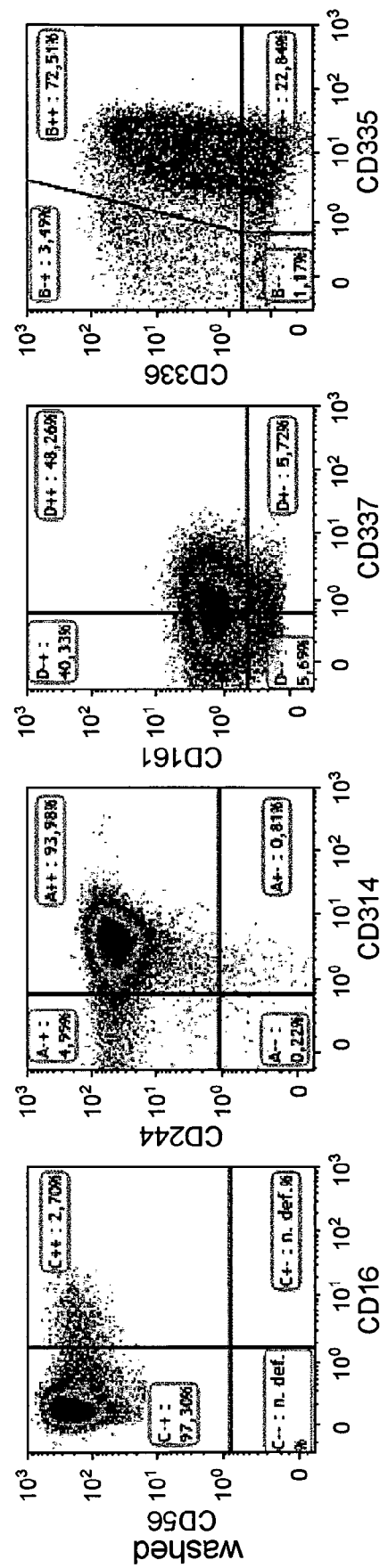

FIG. 3. Flow cytometry analysis of ex vivo bioreactor-expanded NK cells before and after washing. The CD56$^+$CD3$^-$ lymphocytes were analyzed of unwashed (A) and washed (B) NK cell products were analyzed. A representative example out of three different NK cell products is shown.

FIG. 4. Stability tests of ex-vivo generated and processed NK cell products. (A) The NK cell content of the processed final product was followed over time, while the products were either stored at 4° C. or room temperature (RT) for a maximum of 3 days. The percentage of the CD45$^+$/CD56$^+$ cells is displayed from 3 different stability tests. (B) Viability of the final NK cell product was followed over time, while the products were either stored at 4° C. or room temperature (RT). The percentage of the CD45$^+$/CD56$^+$/7-AAD$^-$ cells is displayed from 3 different stability tests.

Figure 5A:
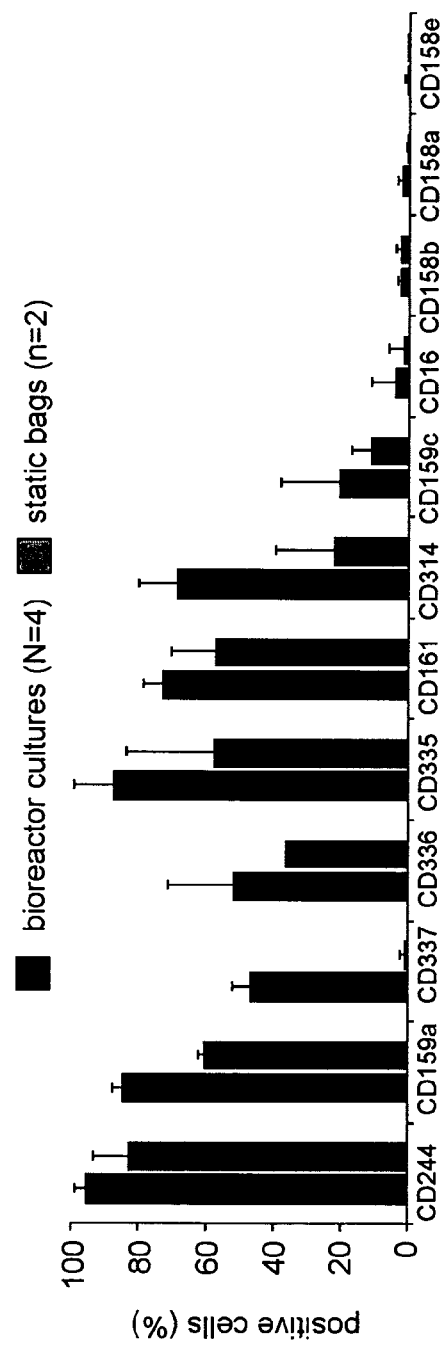
Figure 5B:
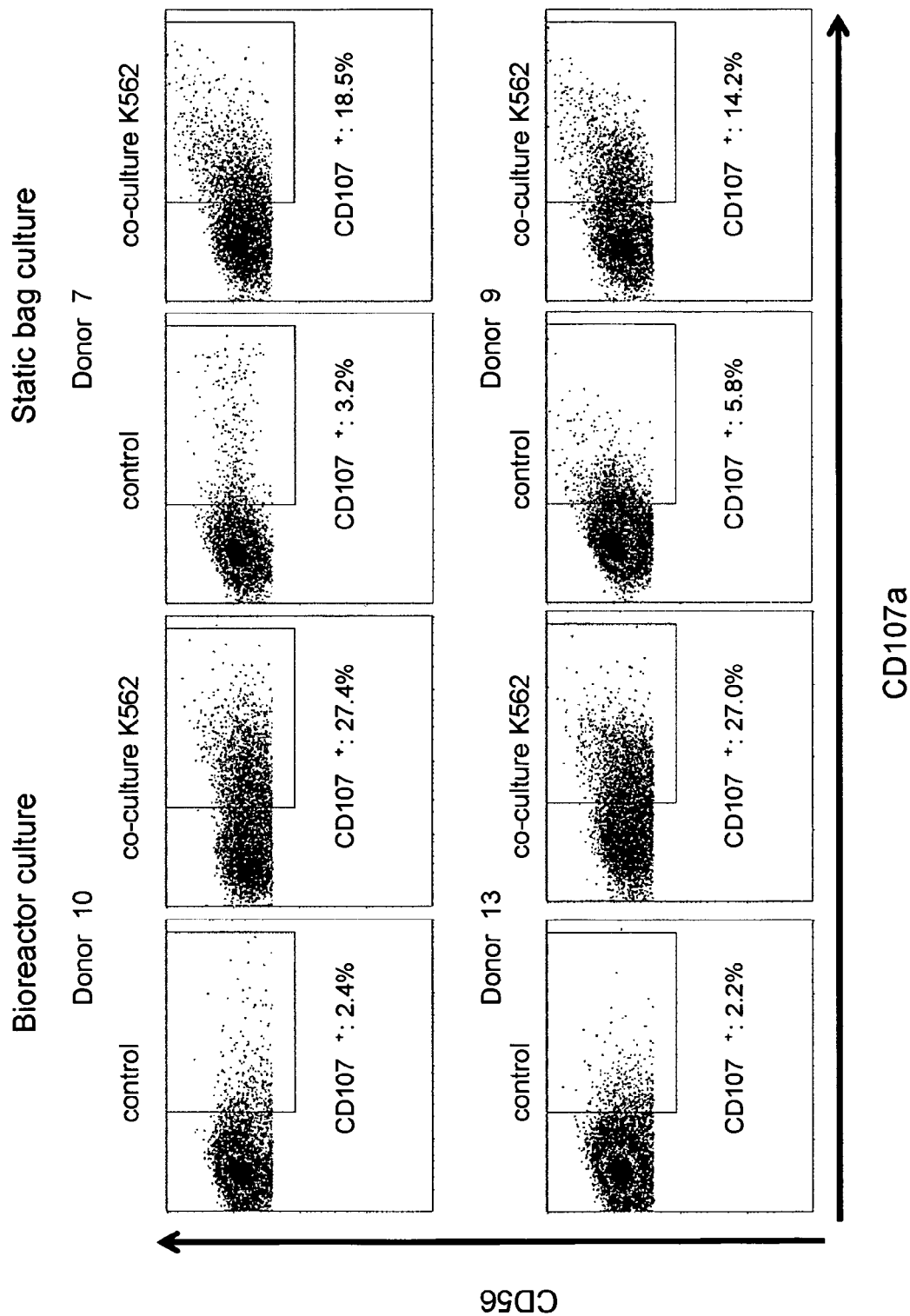
Figure 6A:
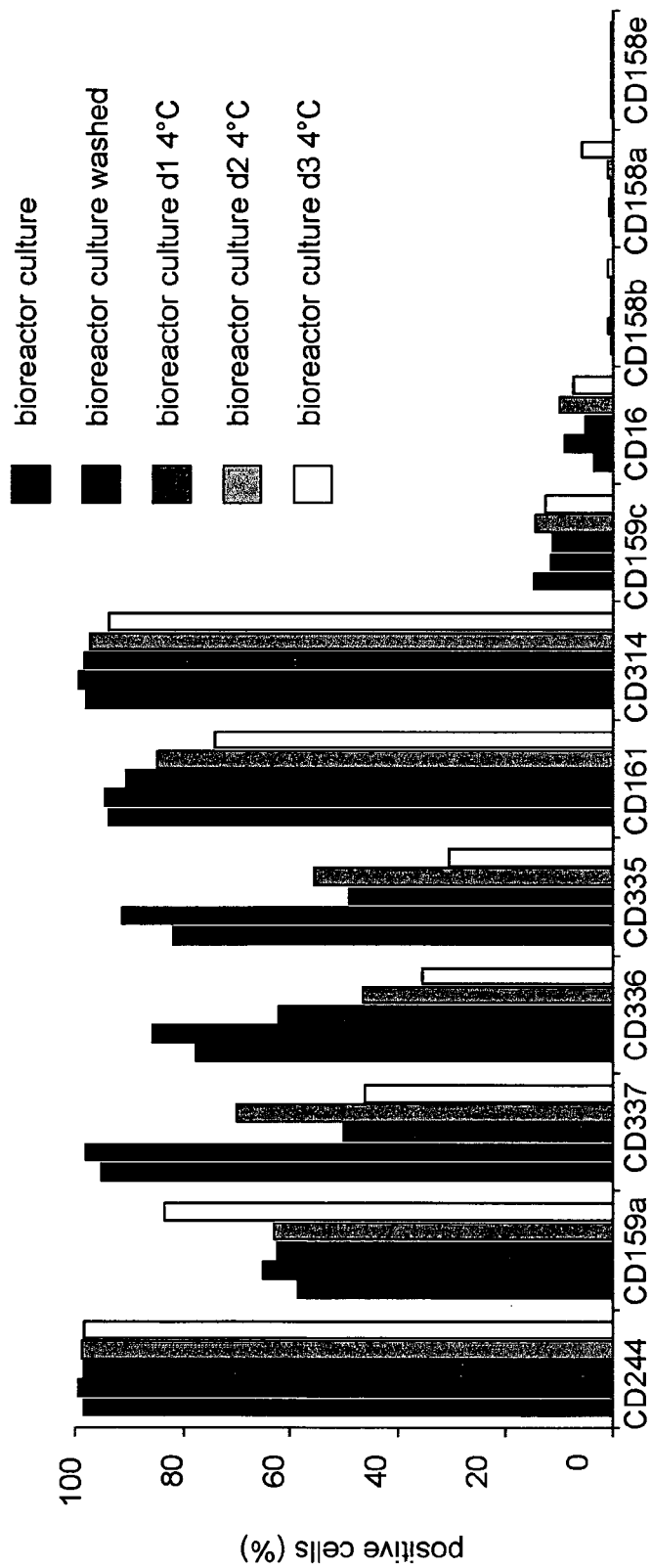
Figure 6B:
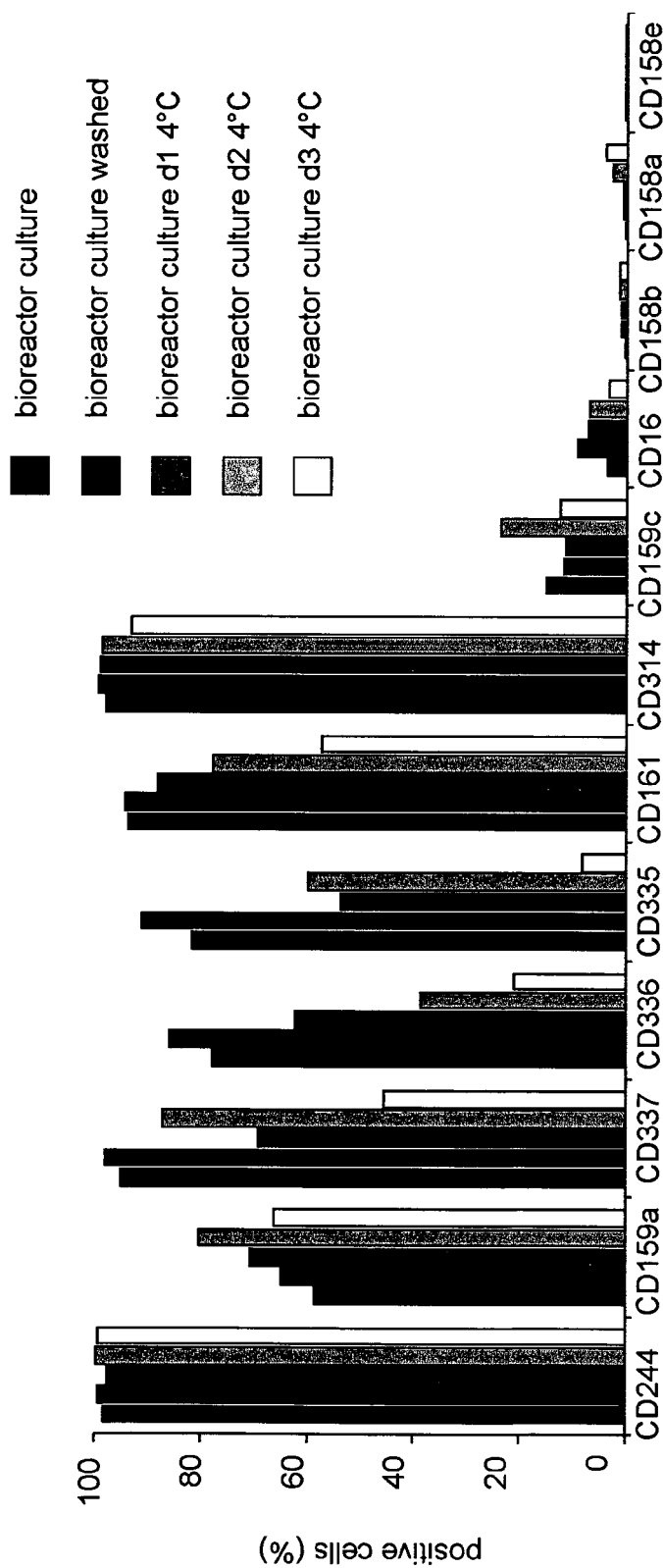
Figure 6C:
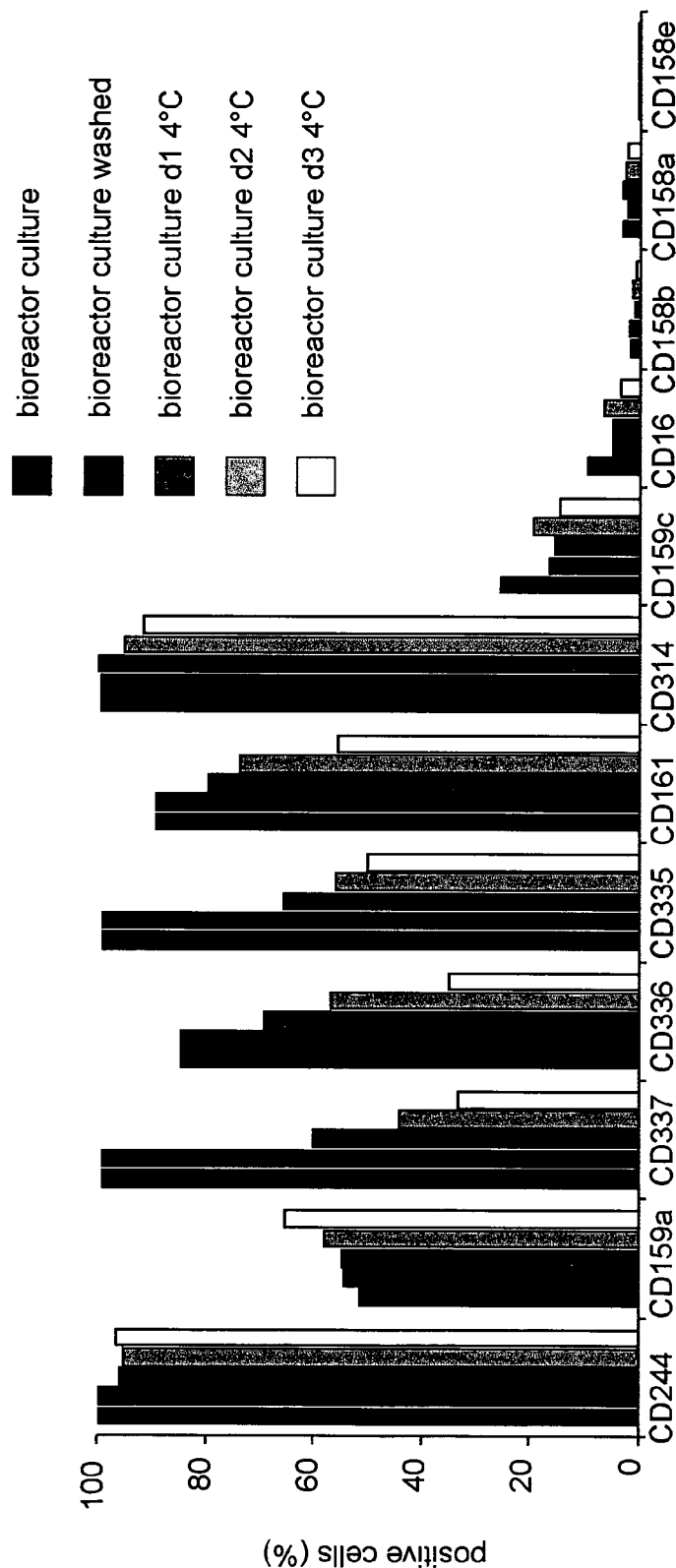
Figure 6D:
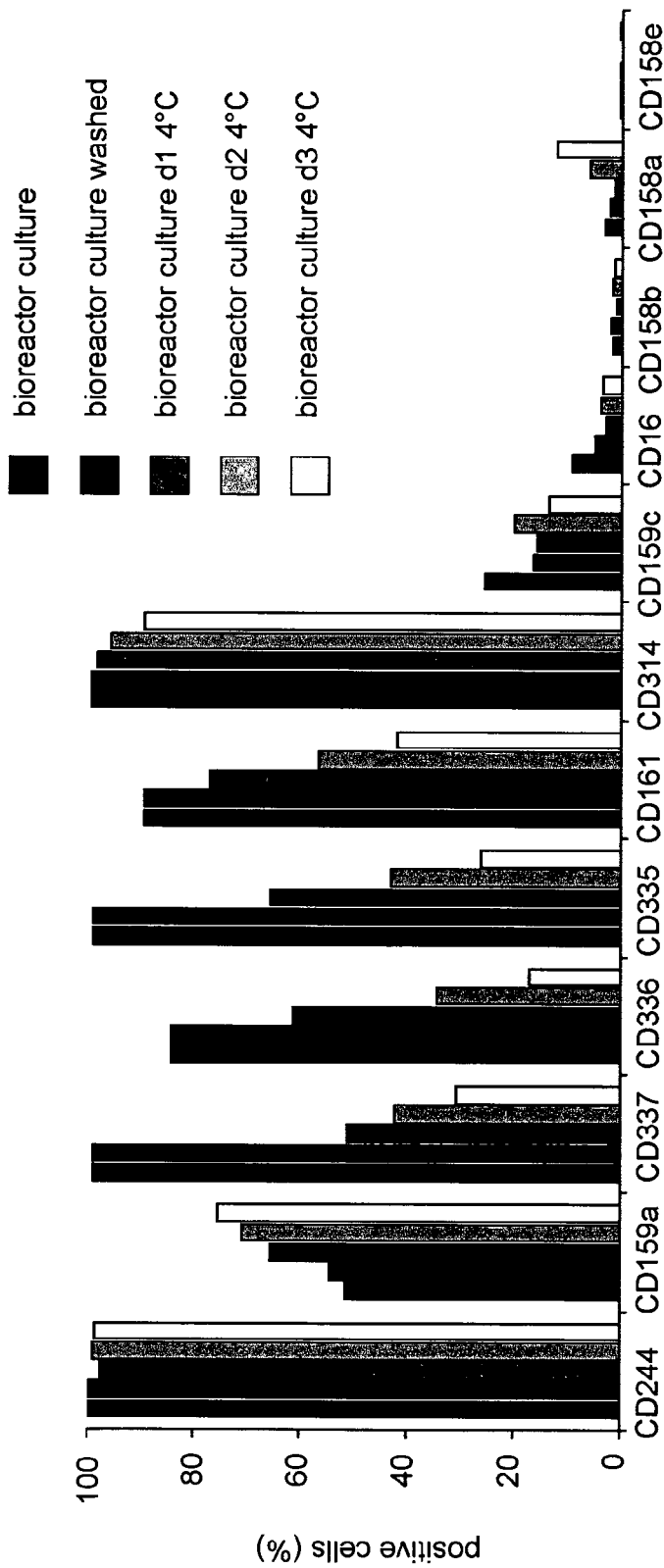

FIG. 5. Percentage cells positive for expression of the indicated marker after culturing in a bioreactor or a static bag (A). Flow cytometry analysis of bioreactor cultured and static bag cultured cells (B).

FIG. 6. Cells from four different donors (A, B, C, and D) were ex-vivo cultured in a bioreactor. Depicted are the percentage cells positive for expression of the indicated marker after culture, washing and after storage at 4° C. for 1, 2 or 3 days as indicated.

Figure 7:
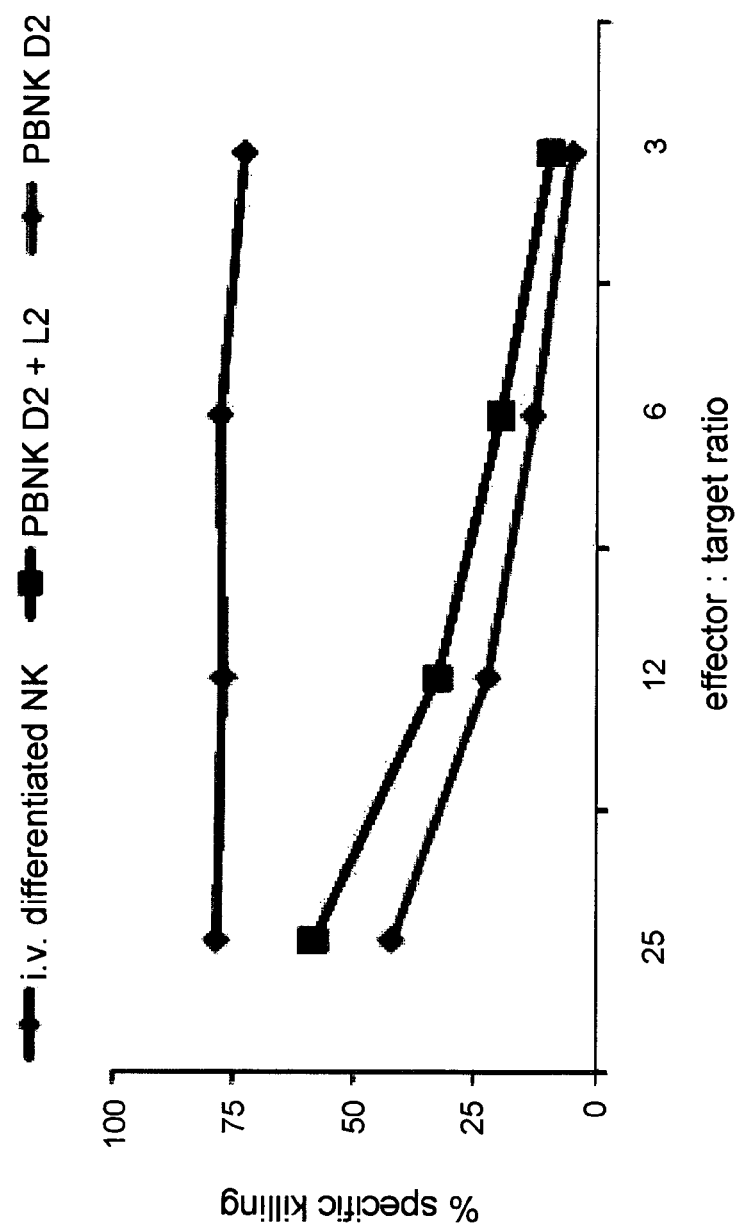

FIG. 7. Ex-vivo (e.v.) generated NK cells efficiently lyse K562 target cells compared to NK cells from peripheral blood (PB).

Figure 8:
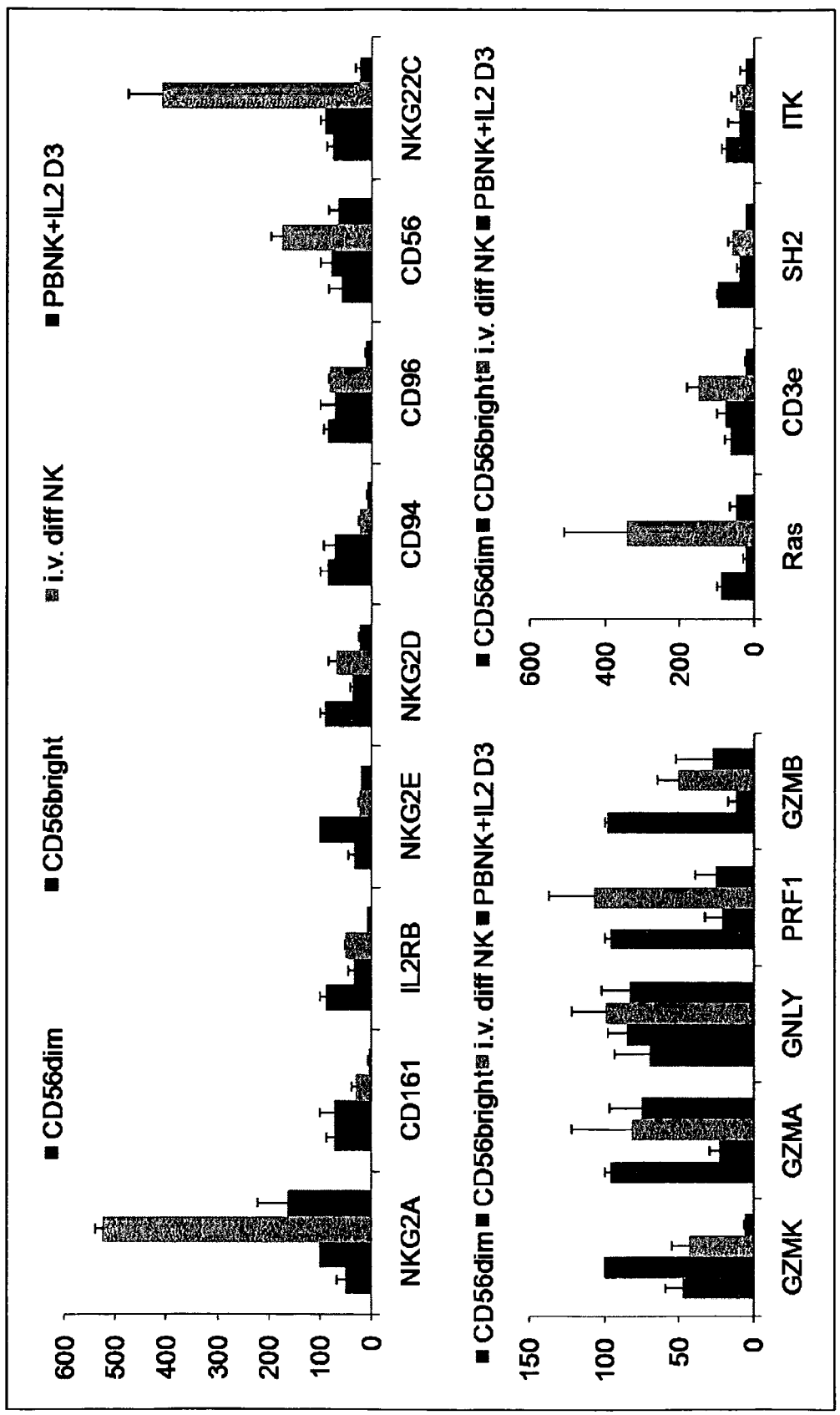

FIG. 8. Expression of several genes from PB dim and bright NK cells, activated PB NK cells to the expression of ex vivo generated NK cells.

Figure 9:
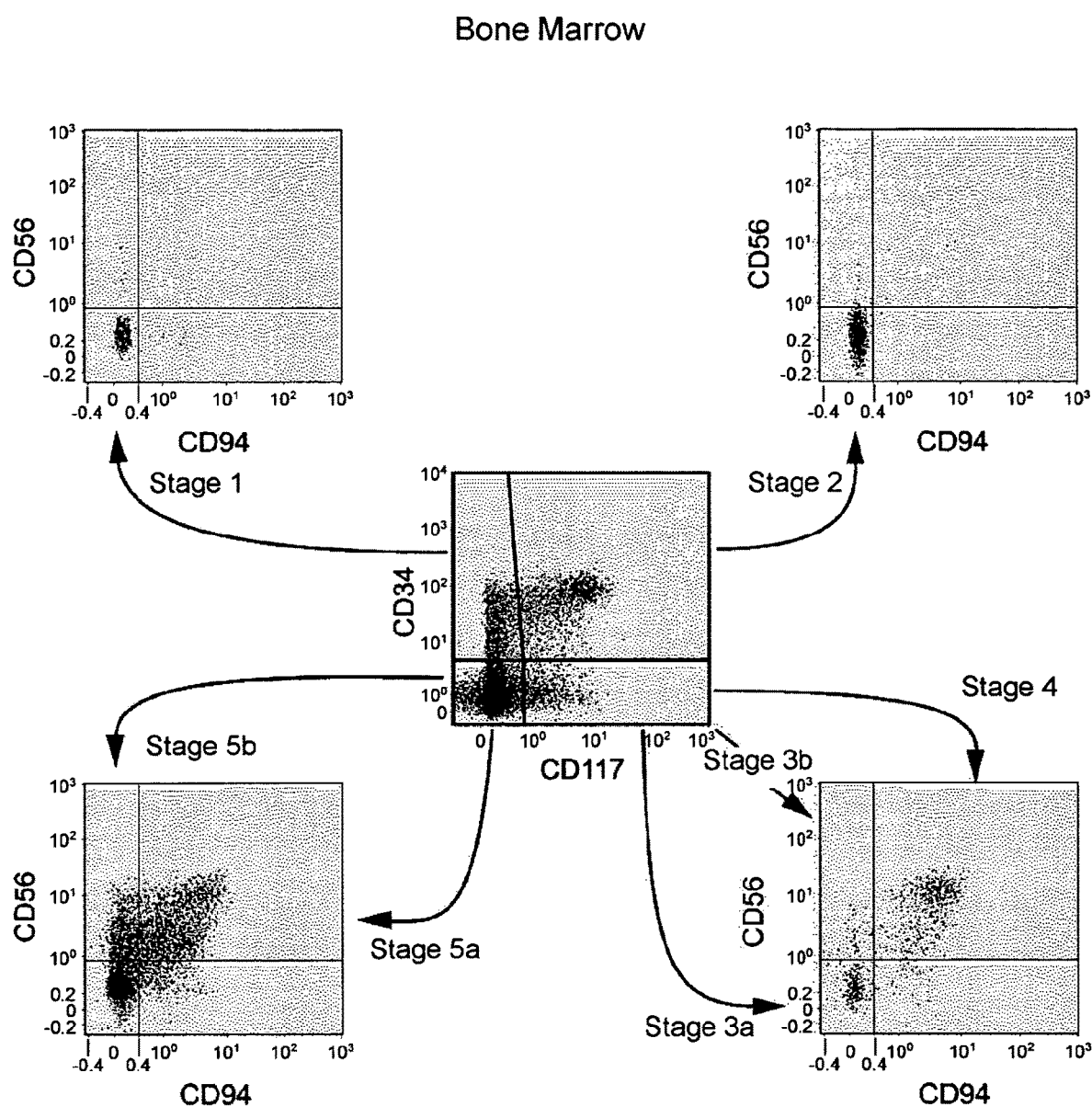

FIG. 9. Identification of seven NK cell developmental stages in bone marrow (BM). Based on the stages defined in Table 5, we analyzed the presence of the different NK cell developmental stages in BM. Shown is one representative example (n=5). Cells were gated on the CD45$^+$CD3$^-$ population within CD45$^+$/SS gated cells to exclude T cells and endothelial cells from analysis. Subsequently, cell subsets were divided based on the expression of CD34 and CD117. From there, each subset was analyzed for CD56 and CD94 expression, leading to the identification of seven NK cell developmental stages: 1, 2, 3a, 3b, 4, 5a, 5b.

Figure 10:
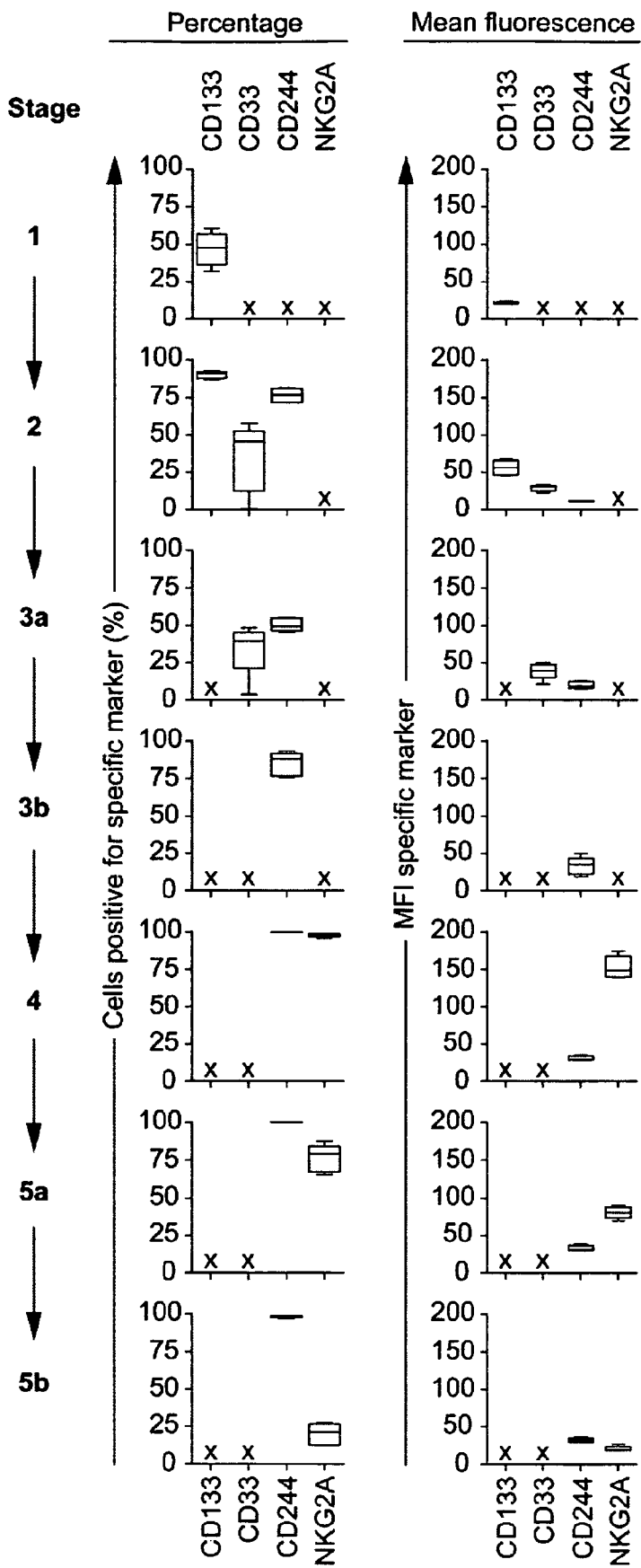

FIG. 10. Expression of CD133, CD33, CD244 and NKG2A within the NK cell developmental stages in bone marrow (BM). Cells were gated on the CD45$^+$CD3$^-$ population within CD45$^+$/SS gated cells to exclude T cells and endothelial cells from analysis. Next, cell subsets were divided based on the expression of CD34 and CD117. From there, each subset was analyzed for CD56 and CD94 expression. Subsequently, the expression of CD133, CD33, CD244 and NKG2A was analyzed within the different NK cell developmental stages in BM (n=5). Left panels show the percentages of cells positive for the specific markers. Right panels show the mean fluorescence (MFI) of each specific marker. Cell populations >0.1% of the CD45$^+$CD3$^-$ population with a threshold of more than 50 cells were considered reliable. Cell populations were considered tissue specific when at least 3 out of 5 samples showed reliable results. Cell populations that did not suffice to these criteria were excluded from further (statistical) analysis. Shown in this figure are all NK cell developmental stages within each tissue.

Figure 11:
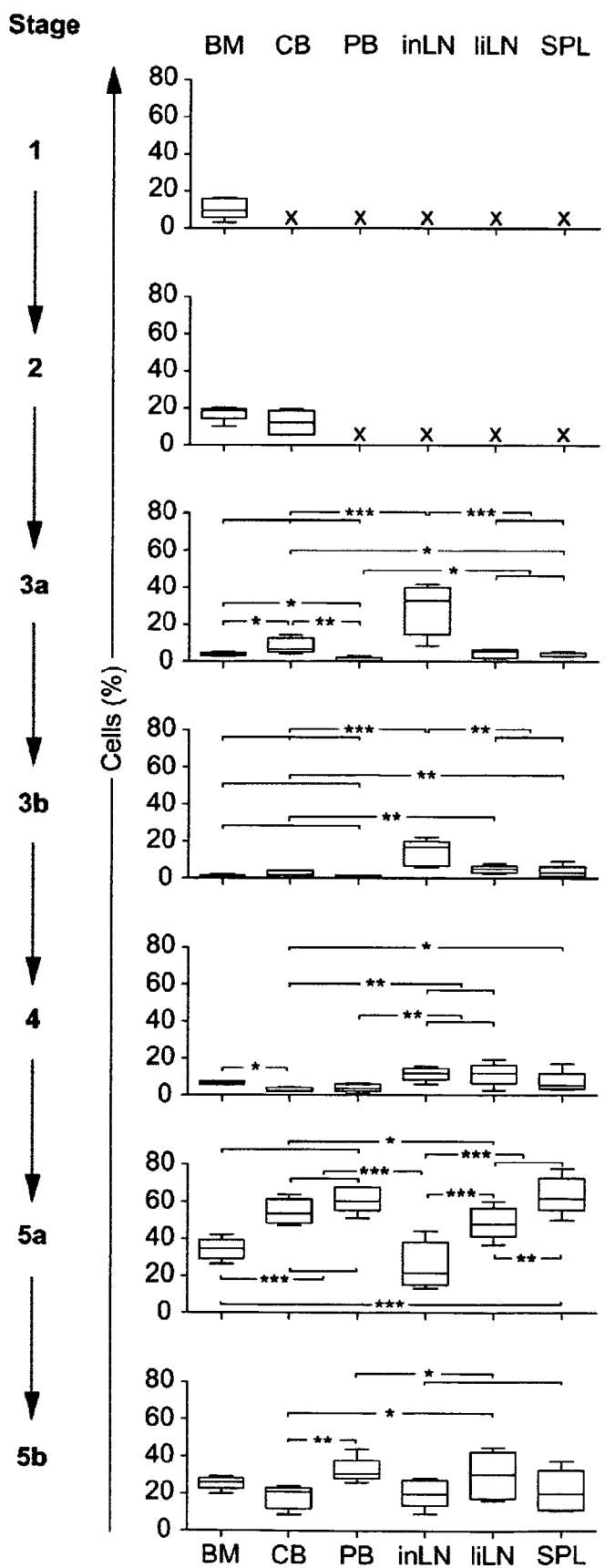

FIG. 11. Distribution of the NK cell developmental stages within different human tissues. The distribution of the seven NK cell developmental stages was analyzed within samples of bone marrow (BM), cord blood (CB), peripheral blood (PB), inguinal LN (inLN), liver LN (liLN) and spleen (SPL) (all n=5). For identification of the NK cell developmental stages, cells were gated on the CD45$^+$CD3$^-$ population within CD45$^+$/SS gated cells to exclude T cells and endothelial cells from analysis. Subsequently, cell subsets were divided based on the expression of CD34 and CD117. From there, each subset was analyzed for CD56 and CD94 expression. Cell populations >0.1% of the CD45$^+$CD3$^-$ population with a threshold of more than 50 cells were considered reliable. Cell populations were considered tissue specific when at least 3 out of 5 samples showed reliable results. Cell populations that did not suffice to these criteria were excluded from further (statistical) analysis. Shown in this figure are all NK cell developmental stages within each tissue. Comparison between the different tissues was analyzed using a random effect logistic regression model; *P<0.05, P<0.01, *P<0.0001.

Figure 12:
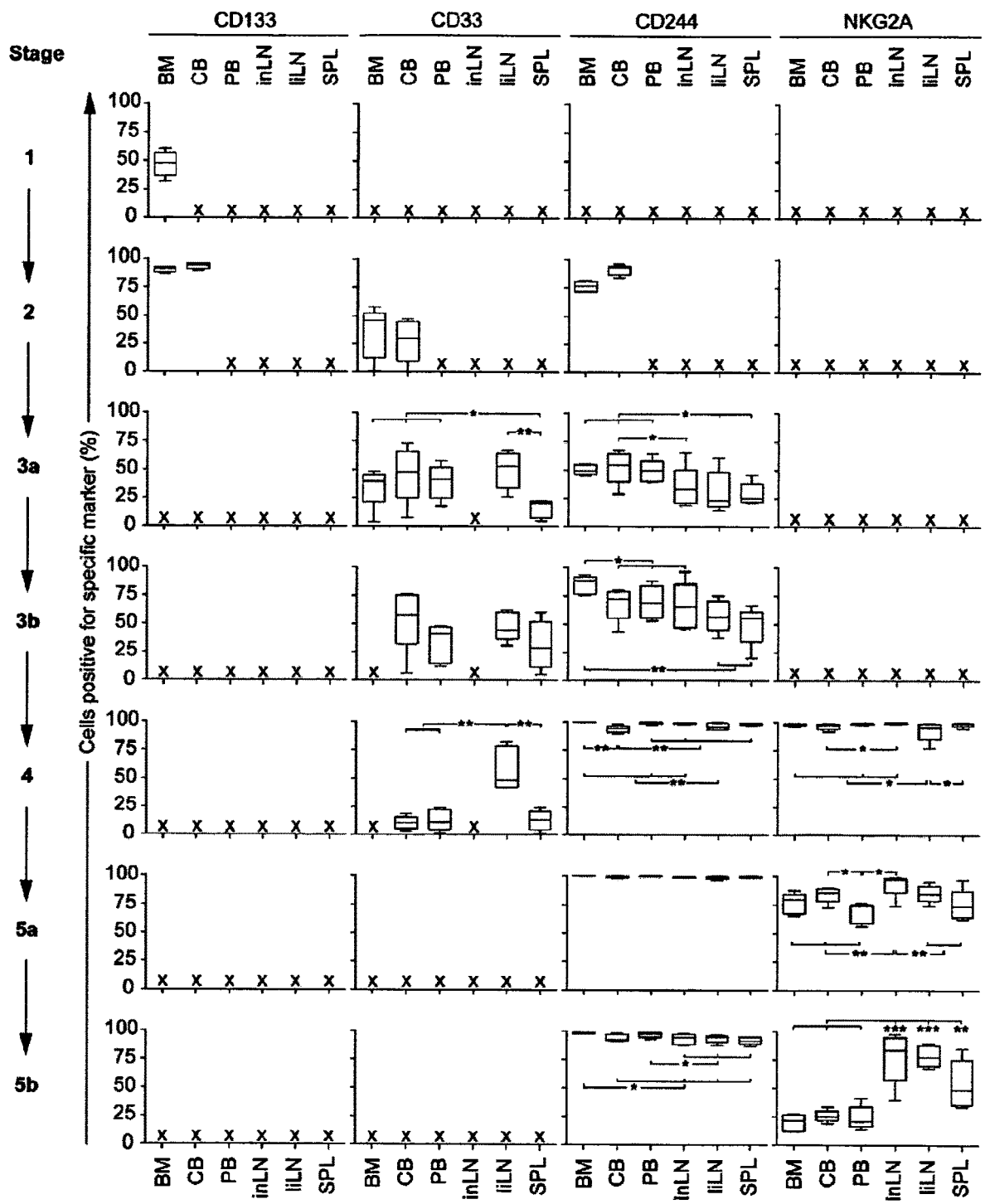

FIG. 12. Expression of CD133, CD33, CD244 and NKG2A within the NK cell developmental stages present in different human tissues. Cells were gated on the CD45$^+$CD3$^-$ population within CD45$^+$/SS gated cells to exclude T cells and endothelial cells from analysis. Next, cell subsets were divided based on the expression of CD34 and CD117. From there, each subset was analyzed for CD56 and CD94 expression. Subsequently, the expression (%) of CD133, CD33, CD244 and NKG2A was analyzed within the different NK cell developmental stages in bone marrow (BM), cord blood (CB), peripheral blood (PB), inguinal LN (inLN), liver LN (liLN) and spleen (SPL) (all n=5). Cell populations >0.1% of the CD45$^+$CD3$^-$ population with a threshold of more than 50 cells were considered reliable. Cell populations were considered tissue specific when at least 3 out of 5 samples showed reliable results. Cell populations that did not suffice to these criteria were excluded from further (statistical) analysis. Comparison between the different tissues was analyzed using a random effect logistic regression model; *P<0.05, P<0.01, *P<0.0001.

Figure 13A:
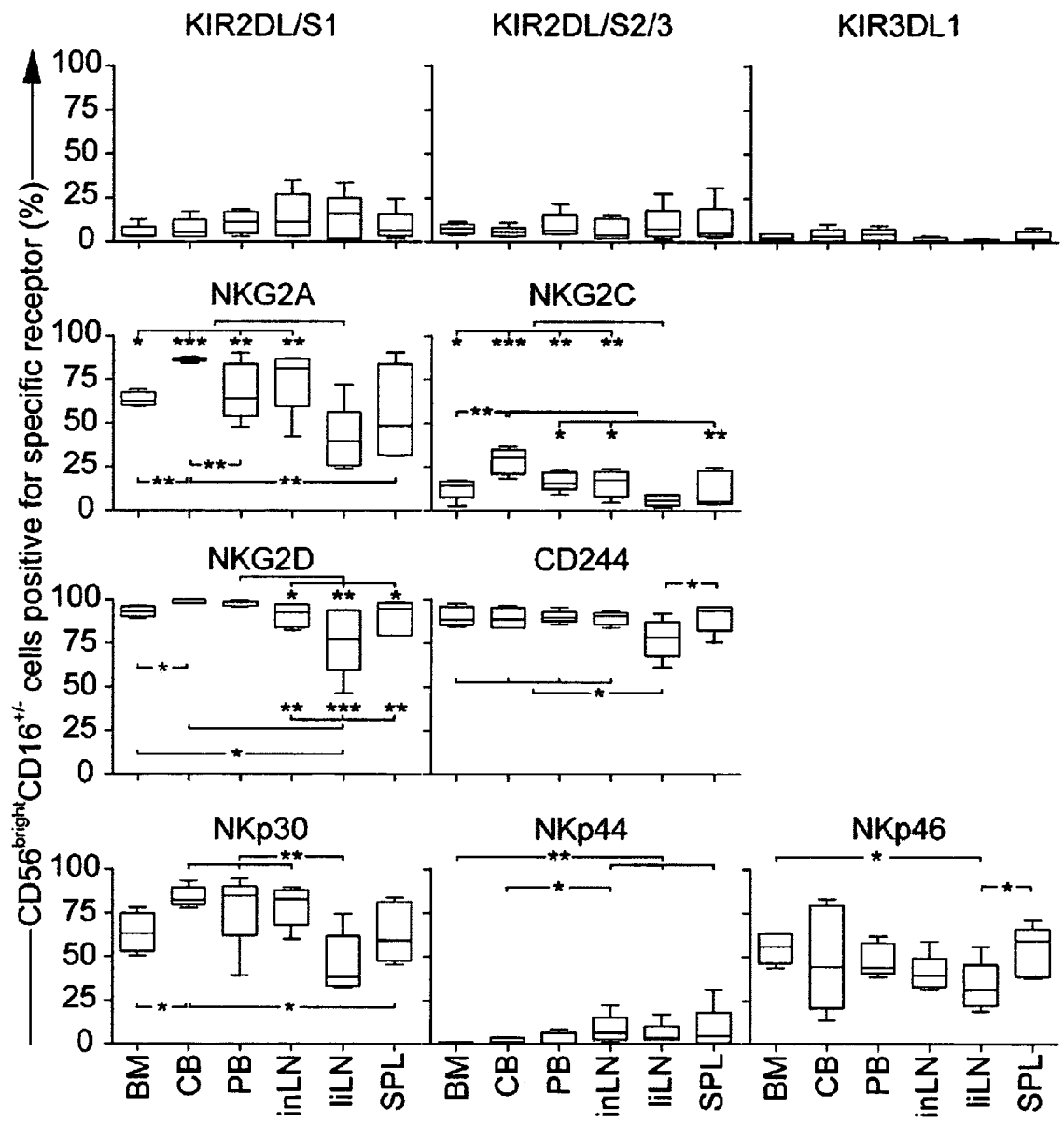
Figure 13B:
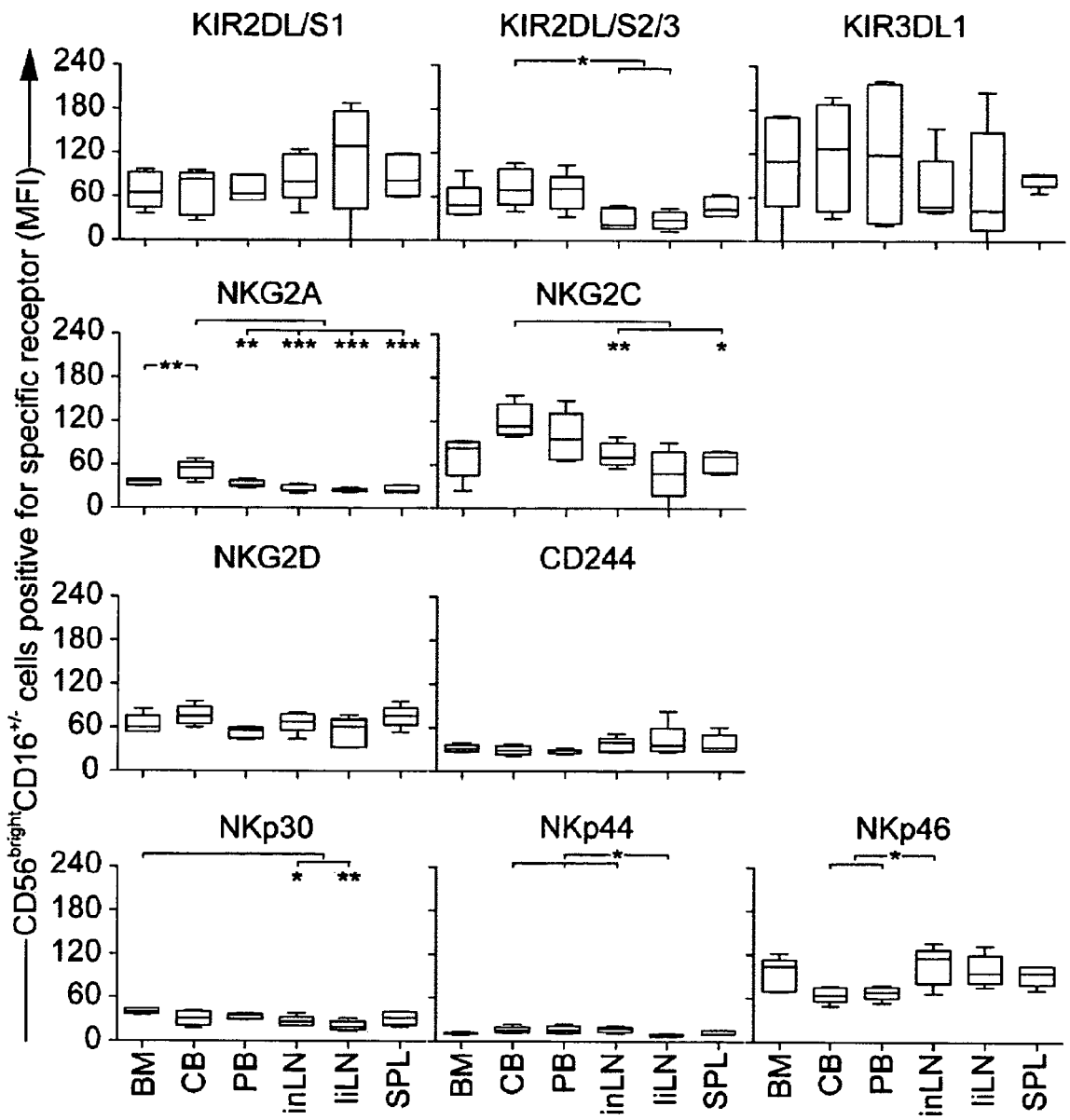

FIG. 13. Expression of KIR, NKG2A/C, NCR, NKG2D and CD244 within the CD56$^{bright}$CD16$^{+/-}$ NK cell subset of different human tissues. Cells were gated on the CD45$^+$CD56$^+$CD3$^-$ population within CD45$^+$/SS gated cells to exclude T cells and endothelial cells from analysis. Subsequently, the expression of KIR, NKG2A/C, NCR (NKp30, 44, 46), NKG2D and CD244 was analyzed within the CD56$^{bright}$CD16$^{+/-}$ NK cell subset present in the committed NK cell population of bone marrow (BM), cord blood (CB), peripheral blood (PB), inguinal LN (inLN), liver LN (liLN) and spleen (SPL) (all n=5). (A) Shown are the percentages of CD56$^{bright}$CD16$^{+/-}$ cells positive for each specific receptor within each tissue. (B) Shown is the mean fluorescence intensity (MFI) for each specific receptor expressed by CD56$^{bright}$CD16$^{+/-}$ cells. Cell populations >0.1% of the CD45$^+$CD3$^-$ population with a threshold of more than 50 cells were considered reliable. Cell populations were considered tissue specific when at least 3 out of 5 samples showed reliable results. Comparison of percentages of positive cells between the different tissues was analyzed using a random effect logistic regression model. Comparison of MFI of positive cells between the different tissues was analyzed using ANOVA; *P<0.05, P<0.01, *P<0.0001.

Figure 14A:
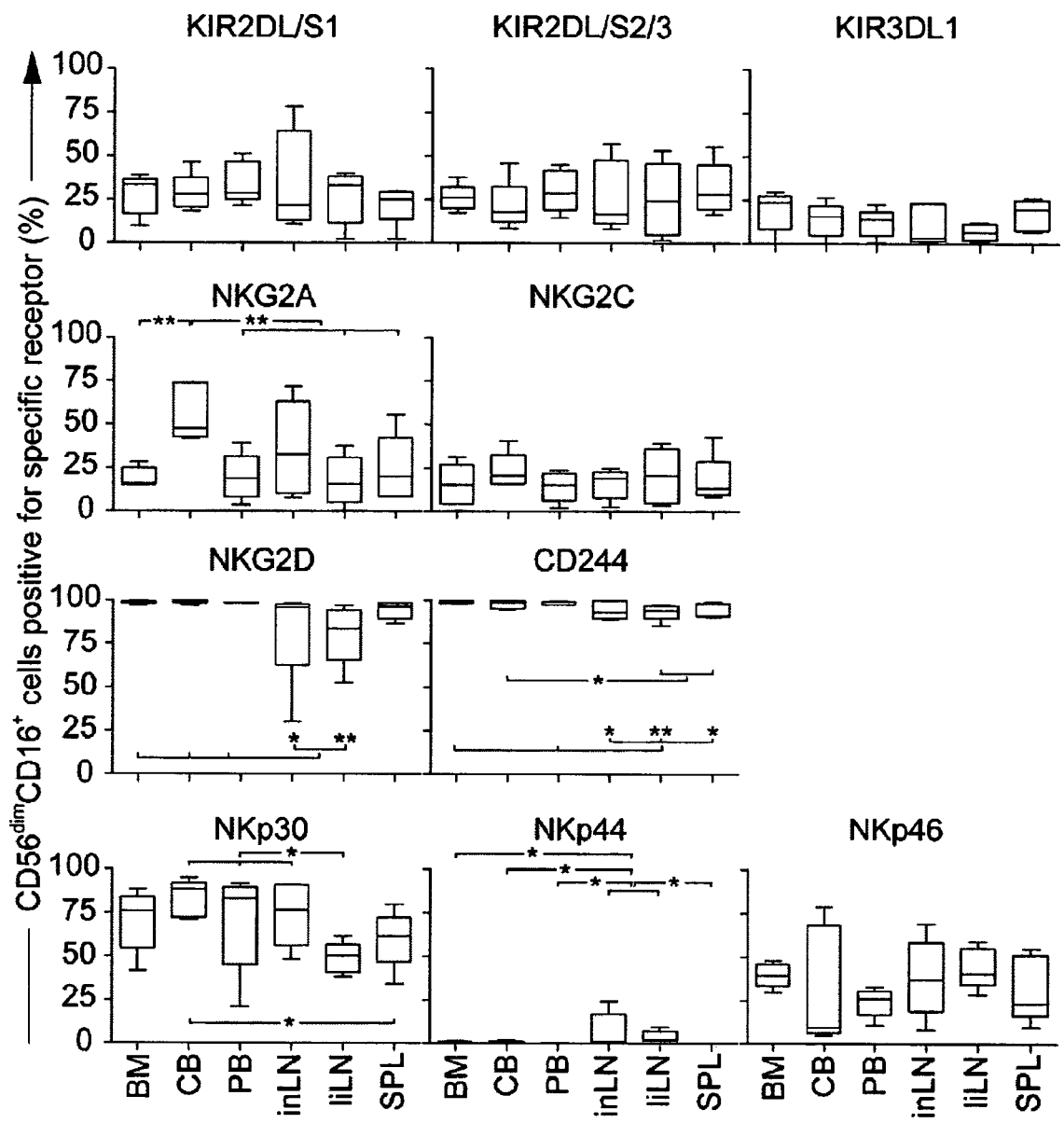
Figure 14B:
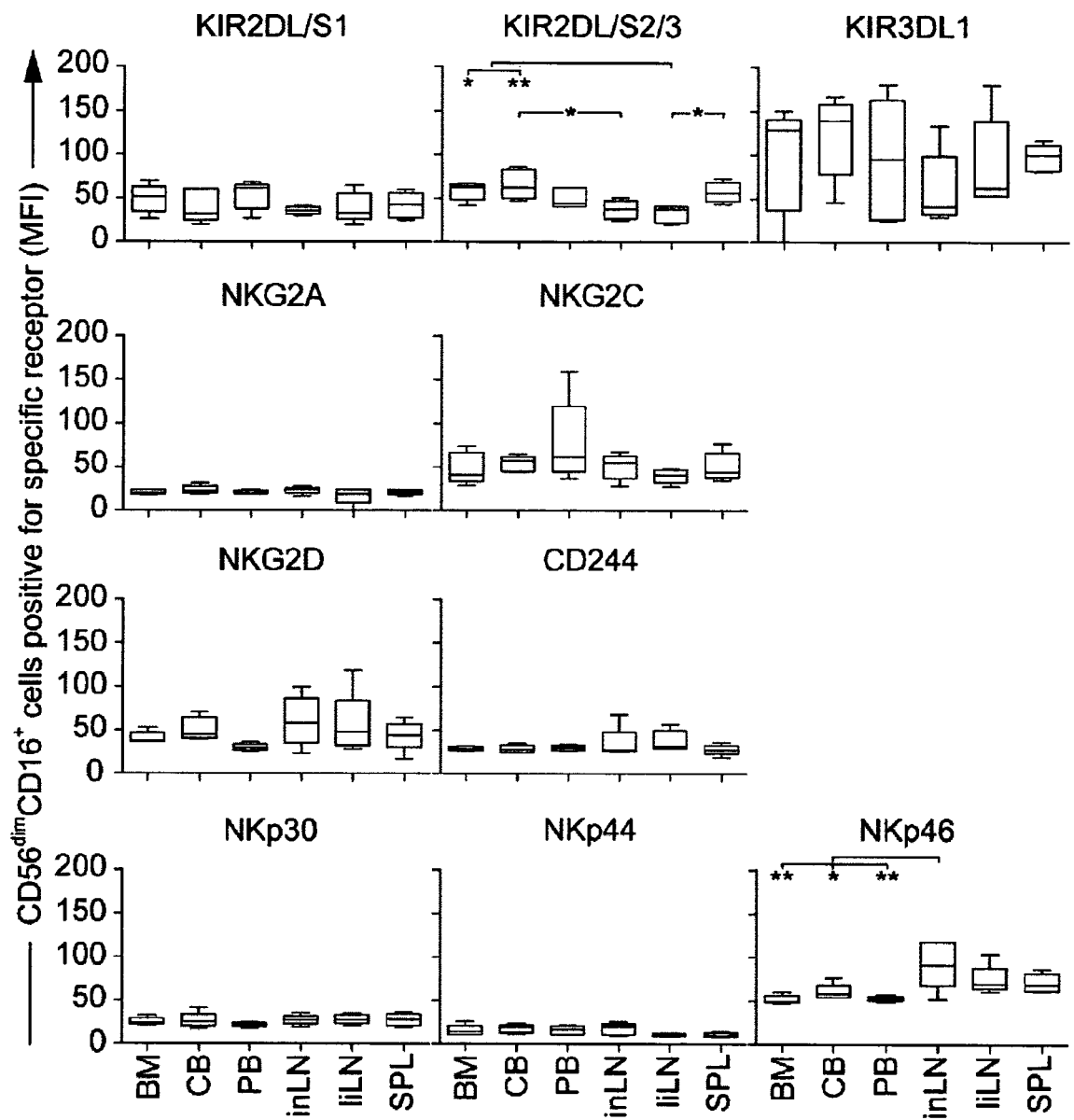

FIG. 14. Expression of KIR, NKG2A/C, NCR, NKG2D and CD244 within the CD56$^{dim}$CD16$^+$ NK cell subset of different human tissues. Cells were gated on the CD45$^+$ CD56$^+$CD3$^-$ population within CD45$^+$/SS gated cells to exclude T cells and endothelial cells from analysis. Subsequently, the expression of KIR, NKG2A/C, NCR (NKp30, 44, 46), NKG2D and CD244 was analyzed within the CD56$^{dim}$CD16$^+$ NK cell subset present in the committed NK cell population of bone marrow (BM), cord blood (CB), peripheral blood (PB), inguinal LN (inLN), liver LN (liLN) and spleen (SPL) (all n=5). (A) Shown are the percentages of CD56$^{dim}$CD16$^+$ cells positive for each specific receptor within each tissue. (B) Shown is the mean fluorescence intensity (MFI) for each specific receptor expressed by CD56$^{dim}$CD16$^+$ cells. Cell populations >0.1% of the CD45$^+$ CD3$^-$ population with a threshold of more than 50 cells were considered reliable. Cell populations were considered tissue specific when at least 3 out of 5 samples showed reliable results. Comparison of percentages of positive cells between the different tissues was analyzed using a random effect logistic regression model. Comparison of MFI of positive cells between the different tissues was analyzed using ANOVA; *P<0.05, **P<0.01.

Figure 15:
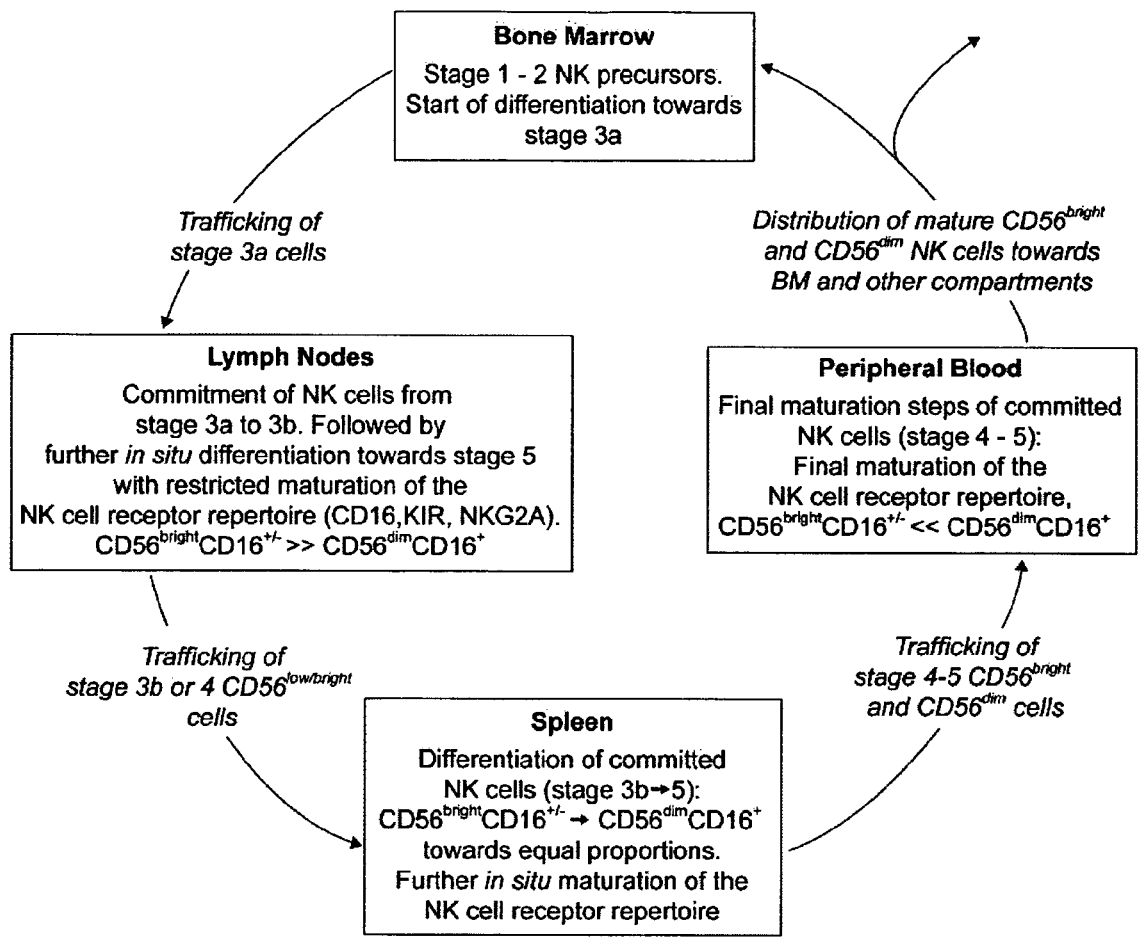

FIG. 15. Proposed model for human NK cell development in vivo. Based on our data, we propose that precursor NK cells (stage 2) traffic from BM to LN, where commitment to the NK cell lineage takes place (stage 3a→3b) followed by in situ differentiation of NK cells with restricted maturation of the NK cell receptor repertoire. For further differentiation of committed NK cells, CD56$^{bright}$ cells (stage 4) may traffic towards splenic tissue in which CD56$^{dim}$ cells may develop and further maturation of the NK cell receptor repertoire takes place. Final maturation of NK cells occurs through trafficking of cells towards the periphery from which NK cells may be further distributed to different compartments in the human body.

Figure 16:
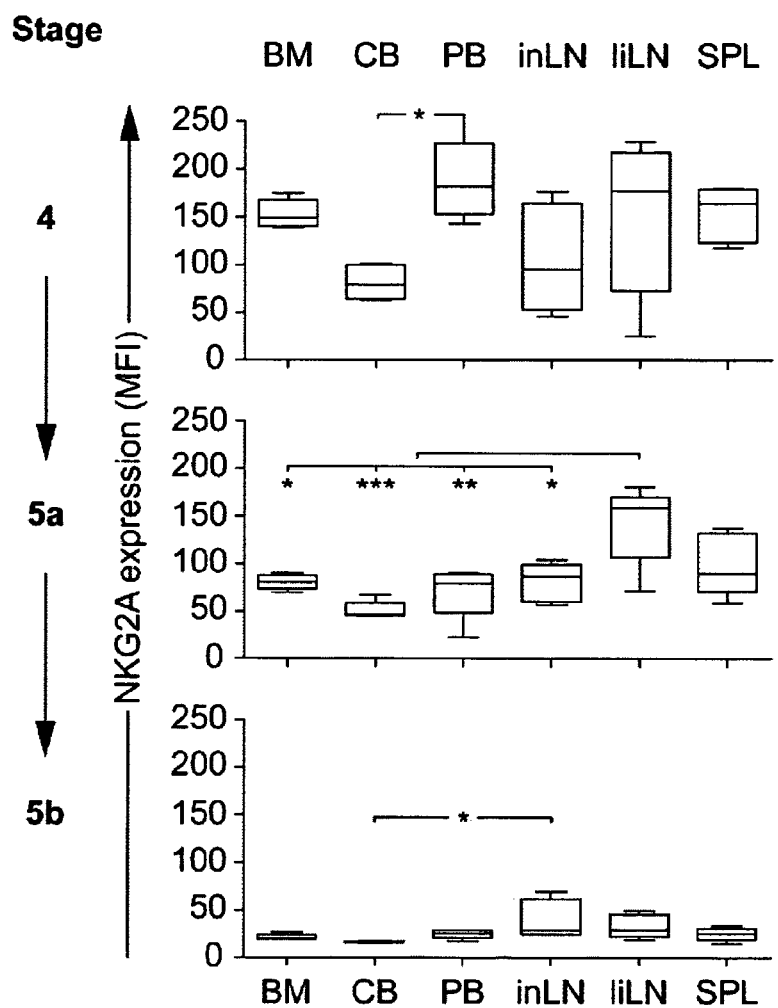

FIG. 16. Mean fluorescence intensity of NKG2A expression following stage 4 to 5b.

Figure 17A:
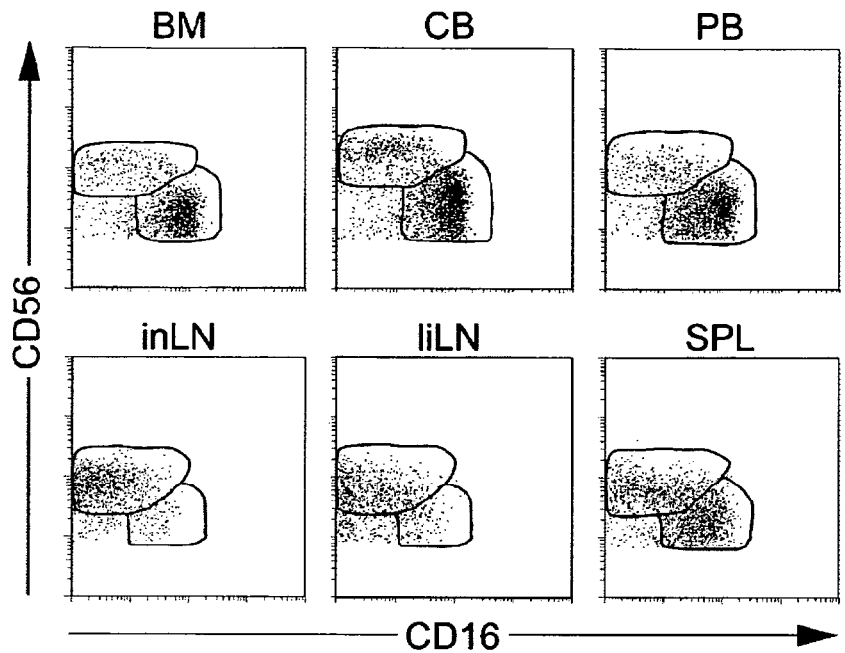
Figure 17B:
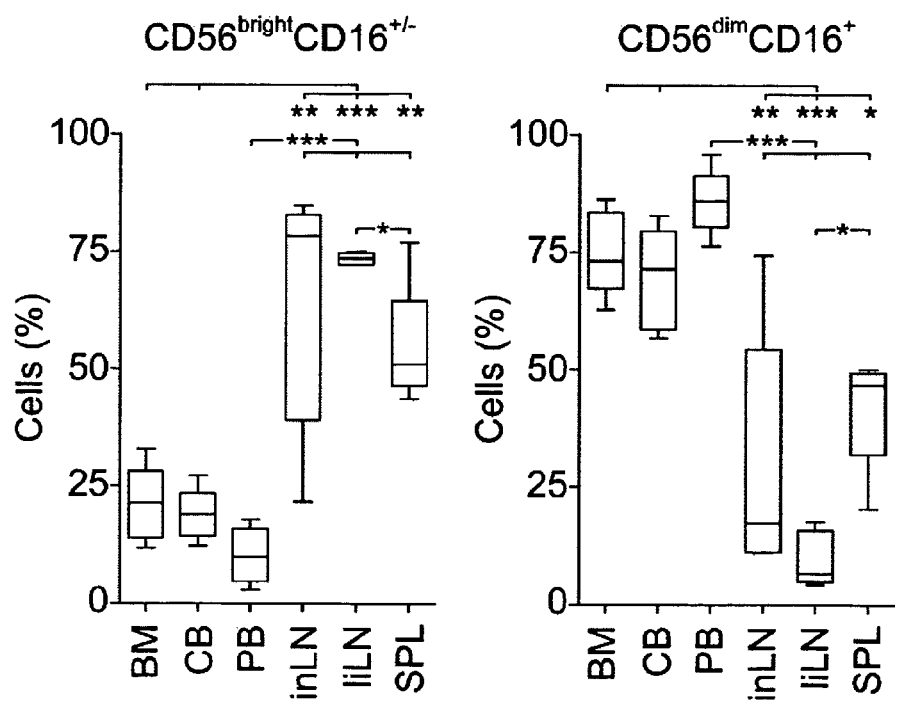

FIG. 17. CD16 and CD56 expression in BM, CB, PB, LN and SPL subsets.

Figure 18A:
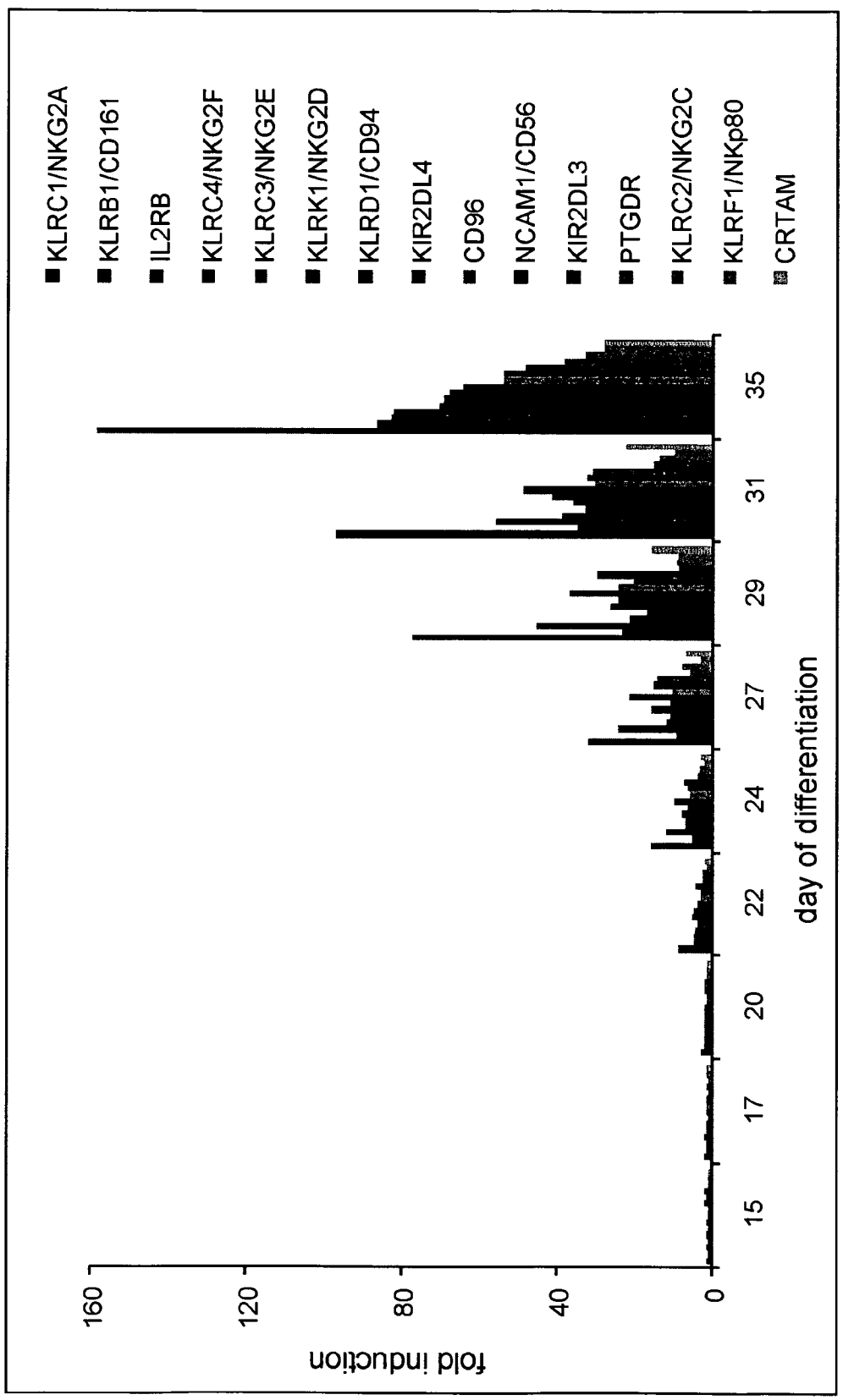
Figure 18B:
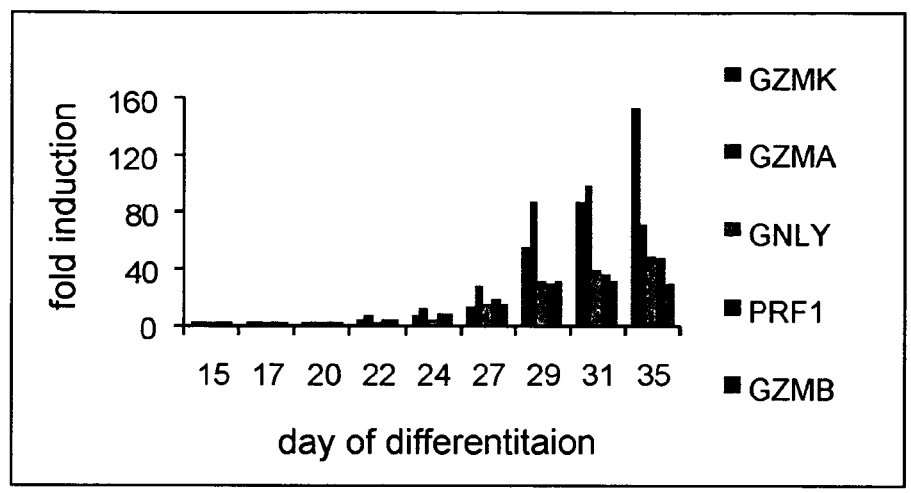
Figure 18C:
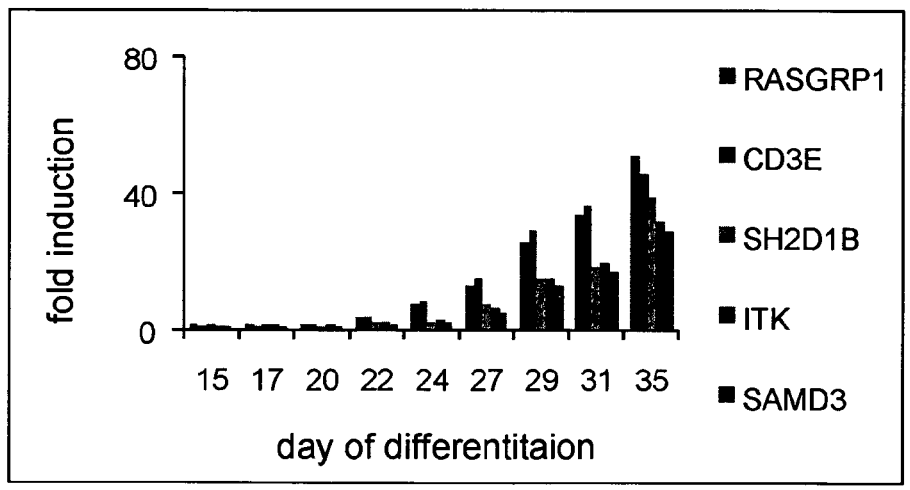

FIG. 18. Gene expression analysis of selected genes during NK cell development on sorted cell populations at day 27 of NK cell development. NK cell cultures after 4 weeks of cultures were sorted into NKp46+NK cell populations further discriminated by NKG2A positive or negative cells. Non NK cells in the culture were characterized by CD14+ and CD14−/NKp46−. Here the most relevant NK cell specific genes were tested for the sorted cell populations such as common NK cell specific receptors that were highly expressed (A) as well as genes for cytolytic molecules (B) and genes known from NK cell signalling (C). NKG2A, CD94 and CD16 were expressed at low levels in the NKG2A− fraction. The NKG2A+ fraction showed a high expression of NKG2A and CD94 and a more intermediate expression of CD16. Furthermore NKG2A+ cells have high expression of various cytolytic molecules (B).

Figure 19:
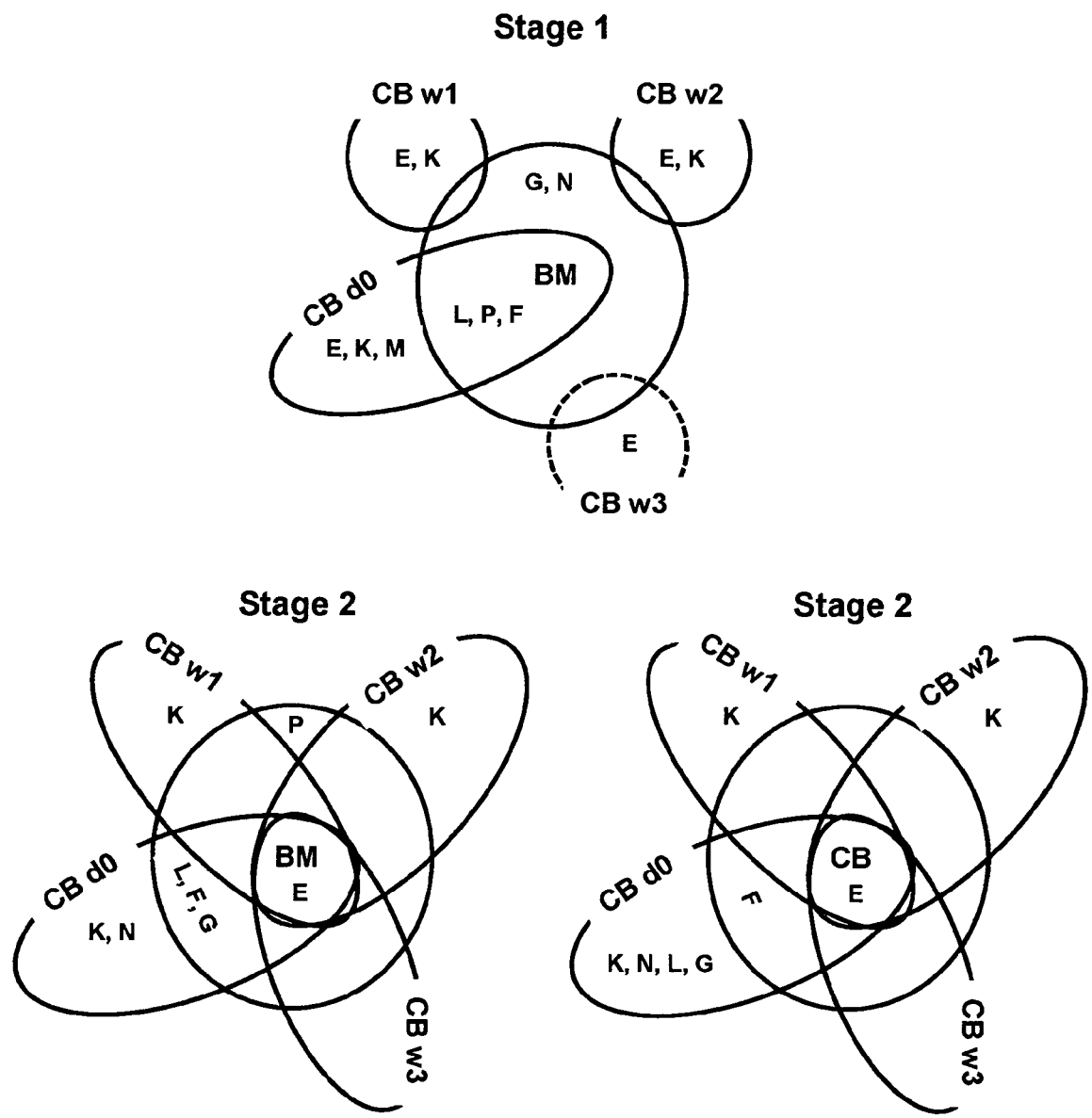

FIG. 19. Stages 1 and 2 are not committed to the NK cell lineage.

Stage 1 is commonly present in bone marrow (BM) and during ex-vivo NK cell generation and compromises subsets of G, N, L, P, F from which G, N are specific for BM tissue and L, P, F could be found in enriched CD34+ cells from umbilical cord blood (CB). Furthermore CB has exclusively E, K, M subsets in stage 1 and E, K subsets are present at week 1 and 2 of NK cell generation.

Stage 2 is commonly present in bone marrow (BM) and during ex-vivo NK cell generation and compromises subsets of G, E, L, P, F from which P is specific for BM tissue and E, L, F, G could be found in enriched CD34+ cells from umbilical cord blood (CB). Furthermore CB has exclusively K, N subsets in stage 2. BM and CB share a central subset E in stage 2 and this remains for at least 3 weeks of culture. CB at day 0 has more exclusive K, N subsets from which K is present at week 1 and 2 during NK cell generation.

Stage 2 cells are found also in CB tissue and share a central subset E with ex-vivo expanded CB cells during 3 weeks of culture. The Cells from ex-vivo culture show an exclusive subset K also after week 1 and 2 of culture.

Figure 20:
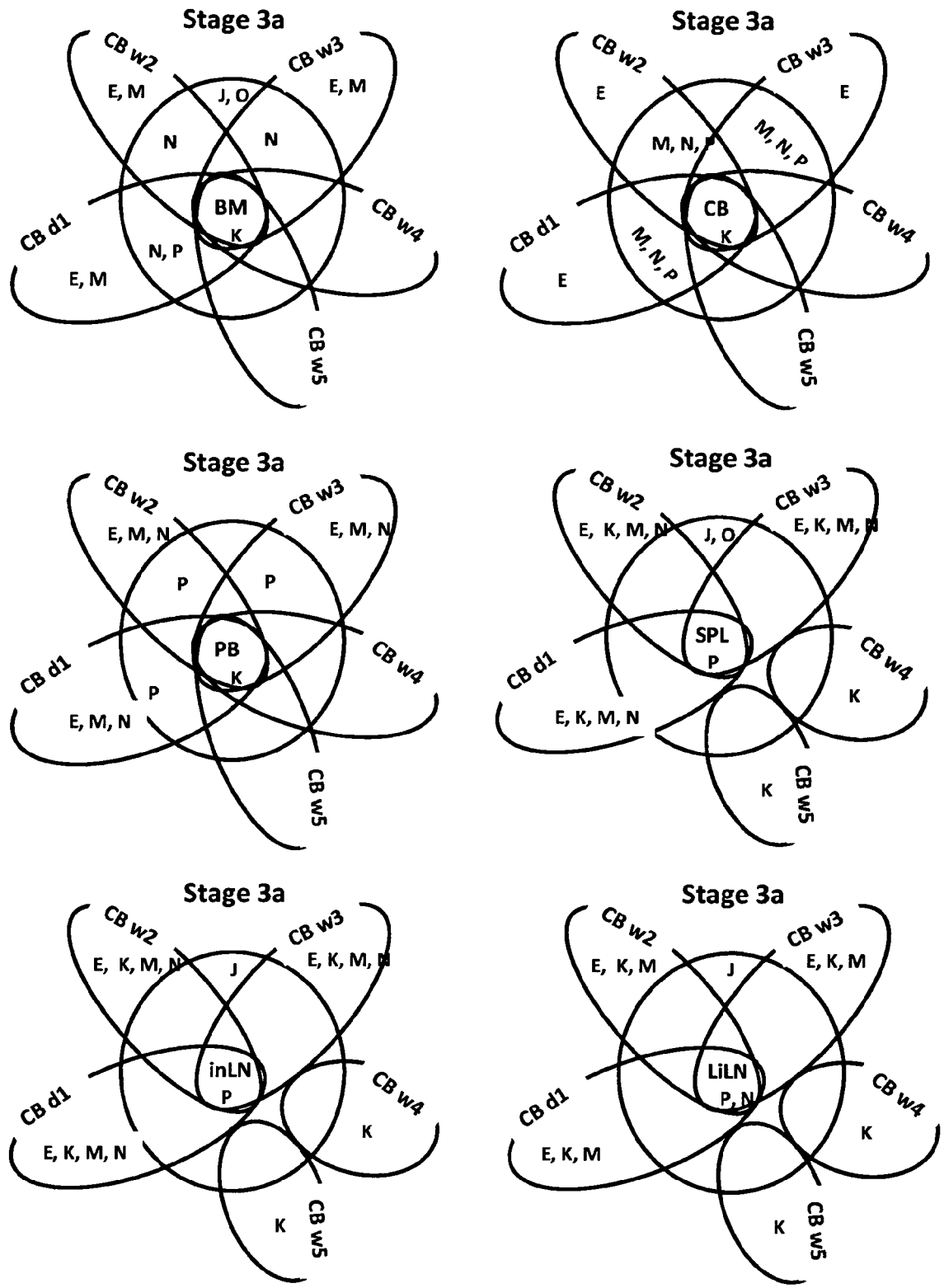

FIG. 20. Stage 3a cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, N, J, O, P could be identified. O is found only in SPL and BM whereas J is additionally also found in inLN and LiLN. BM, CB and PB share a central subset K, which is also present during 5 weeks of NK cell development. SPL, inLN and LiLN share the central P subset and in LiLN also the N subset is central. Where the K subset is central in BM, CB and PB, it is exclusive for ex-vivo cultures compared to SPL, inLN and LiLN.

Ex-vivo cultures have exclusive subsets E, M compared with BM for week 1-3 and share P in the 1st week of culture and N subset for week 1-3.

Ex-vivo cultures have an exclusive subset E compared with CB in week 1-3 and share subsets M, N, P in week 1-3.

Ex-vivo cultures have exclusive subsets E, M, N compared with PB in week 1-3 and share subset P in week 1-3.

Ex-vivo cultures have exclusive subsets E, M, N, K compared with SPL in week 1-3 and subset K in week 4+5.

Ex-vivo cultures have exclusive subsets E, M, N, K compared with inLN in week 1-3 and subset K in week 4+5.

Ex-vivo cultures have exclusive subsets E, M, K compared with LiLN in week 1-3 and subset K in week 4+5.

Figure 21:
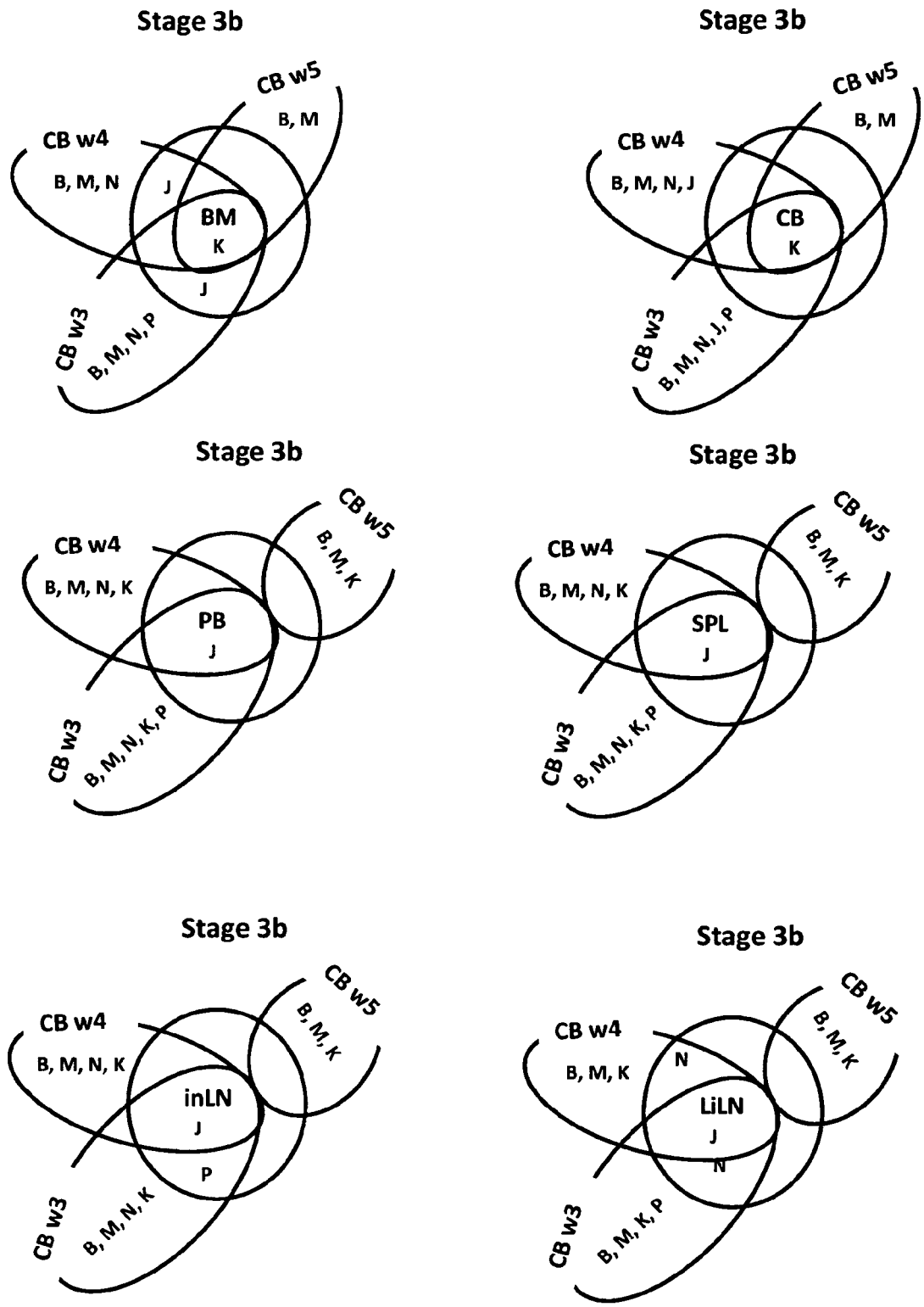

FIG. 21 Stage 3b cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, N, J, B, P could be identified. No tissue specific subset was found. BM and CB share a central subset K, which is also present during 3 weeks of NK cell differentiation (week 3-5). PB, SPL, inLN and LiLN share the central J subset.

Ex-vivo cultures have exclusive subsets B, M, N, P compared with BM for week 3, B, M, N for week 4 and share J in the 3rd and 4th week of culture. B, M subsets are exclusively seen in week 5 of ex-vivo cultures.

Ex-vivo cultures have exclusive subsets B, M, N, J, P compared with CB for week 3, B, M, N, J for week 4 of culture. B, M subsets are exclusively seen in week 5 of ex-vivo cultures.

Ex-vivo cultures have exclusive subsets B, M, N, K, P compared with PB for week 3, B, M, N, K for week 4 of culture. B, M, K subsets are exclusively seen in week 5 of ex-vivo cultures.

Ex-vivo cultures have exclusive subsets B, M, N, K, P compared with SPL for week 3, B, M, N, K for week 4 of culture. B, M, K subsets are exclusively seen in week 5 of ex-vivo cultures.

Ex-vivo cultures have exclusive subsets B, M, N, K compared with inLN for week 3, and 4 and P subset is shared in the 4th week of culture. B, M, K subsets are exclusively seen in week 5 of ex-vivo cultures.

Ex-vivo cultures have exclusive subsets B, M, K, P compared with LiLN for week 3, B, M, K for week 4 and share N in the 3rd and 4th week of culture. B, M, K subsets are exclusively seen in week 5 of ex-vivo cultures.

Figure 22:
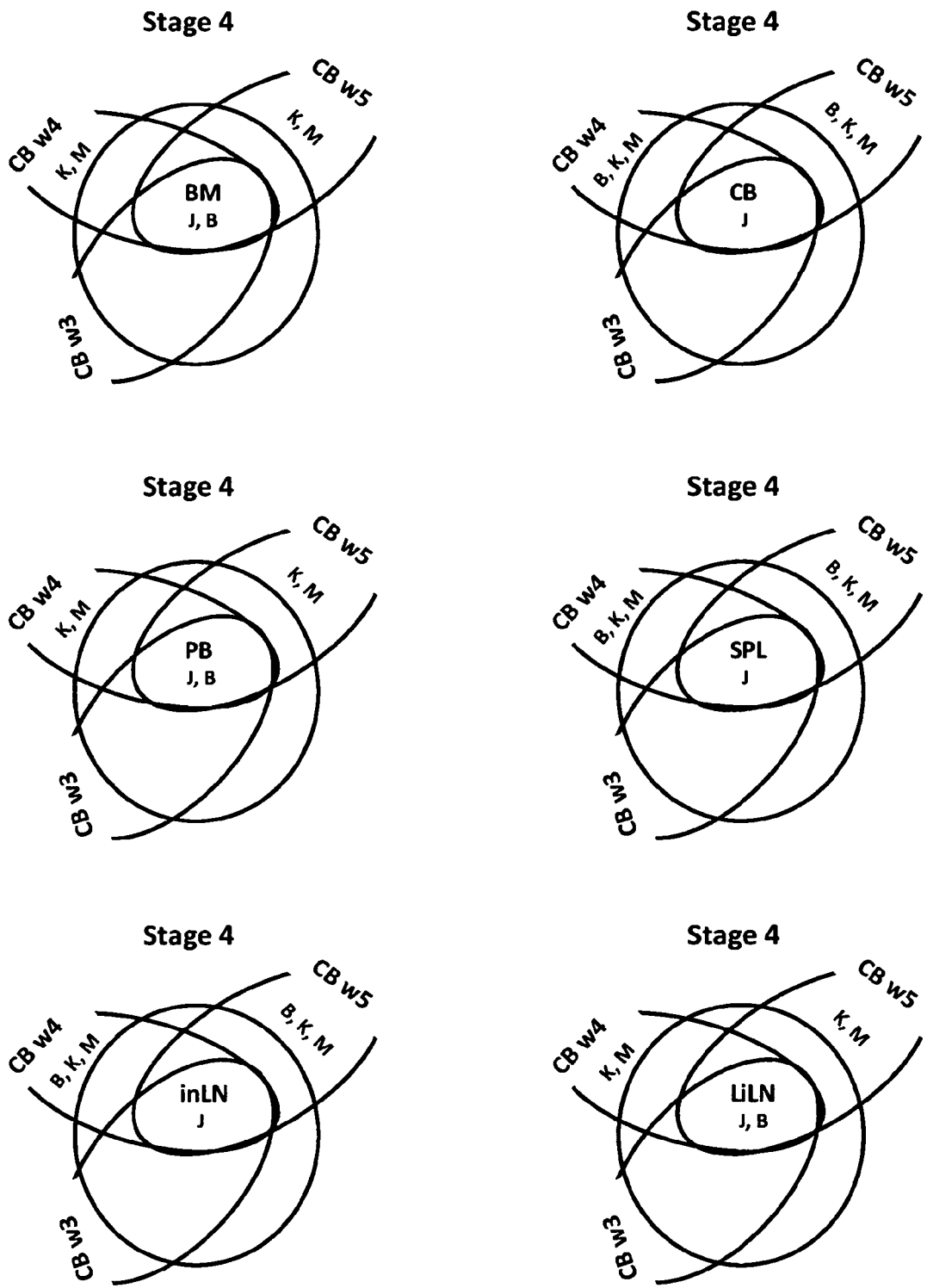

FIG. 22 Stage 4 cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, J, B could be identified. No tissue specific subset was found. BM, PB and LiLN share central subsets J, B, which are present during 3 weeks of NK cell differentiation (week 3-5). CB, SPL and inLN share the central J subset. Ex-vivo cultures have exclusive subsets K, M, compared with BM, PB and LiLN for week 4+5. B, K, M subsets are exclusively seen in week 4+5 of ex-vivo cultures compared to CB, SPL and inLN.

Figure 23:
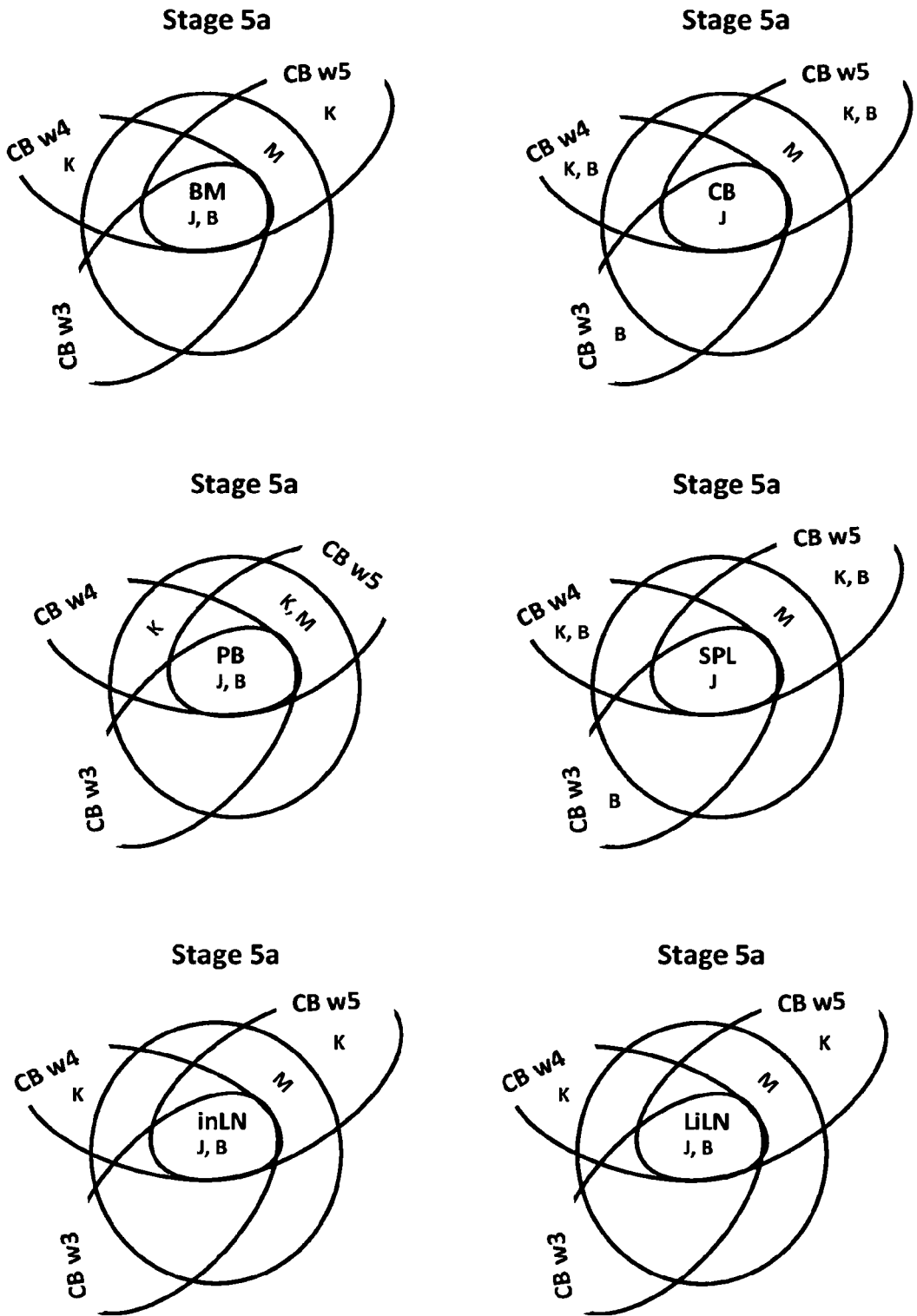

FIG. 23 Stage 5a cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, J, B could be identified. No tissue specific subset was found. BM, PB, inLN and LiLN share central subsets J, B, which are present during 3 weeks of NK cell differentiation (week 3-5). In CB and SPL share the central J subset compared to week 3-5 of culture.

Ex-vivo cultures have exclusive subset K compared with BM, inLN and LiLN during 4th and 5th week of culture. M subset is shared in week 5 of ex-vivo cultures.

Ex-vivo cultures have an exclusive subset B in the 3rd week of culture compared with CB and SPL and further exclusive subsets K, B during 4th and 5th week of culture. M subset is shared in week 5 of ex-vivo cultures.

Ex-vivo cultures subset subsets K compared with PB in the 4th week and share subsets K, M during the 5th week of culture.

Figure 24:
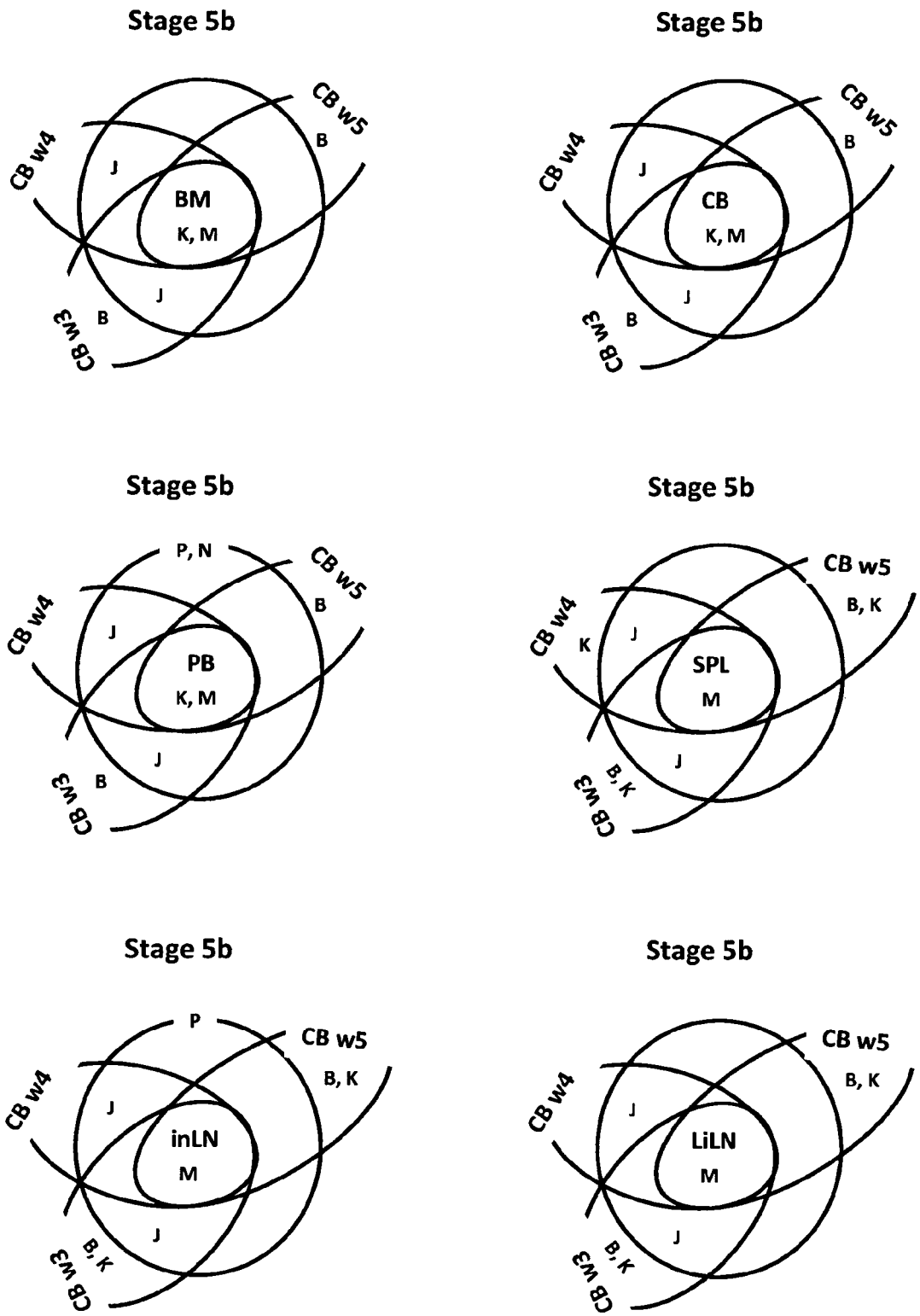

FIG. 24 Stage 5b cells are found in various tissues such as BM, CB, peripheral blood (PB), spleen (SPL), inguinal lymph nodes (inLN), liver lymph nodes (LiLN) and during ex-vivo NK cell generation. Several subsets such as K, M, J, B, P, N could be identified. Tissue specific subsets as P, N in PB and P in inLN were found. BM, CB, PB, SPL, inLN and LiLN share a central main subset M, which is present during 3 weeks of NK cell differentiation (week 3-5). In BM, CB and PB they share additionally the central small subset K compared to week 3-5 of culture.

Ex-vivo cultures have exclusive subset B compared with BM, CB and PB during 3rd and 5th week of culture. J subset is shared in week 4+5 of ex-vivo cultures.

Ex-vivo cultures have exclusive subsets B, K compared with SPL, inLN and LiLN 3rd and 5th week of culture. J subset is shared in week 4+5 of ex-vivo cultures.

Figure 25:
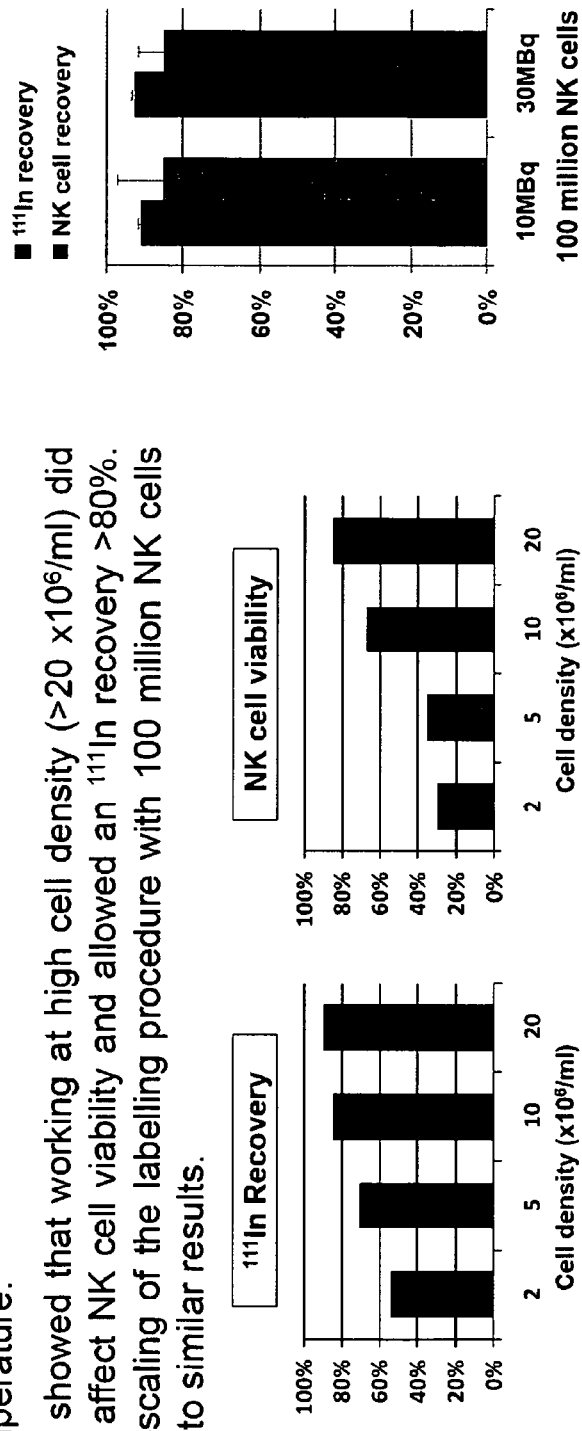

FIG. 25 Labelling of in vitro cultured cells of the invention (harvested at the w5 time point) with indium for in vivo homing study in NOD-SCID mice.

Figure 26:
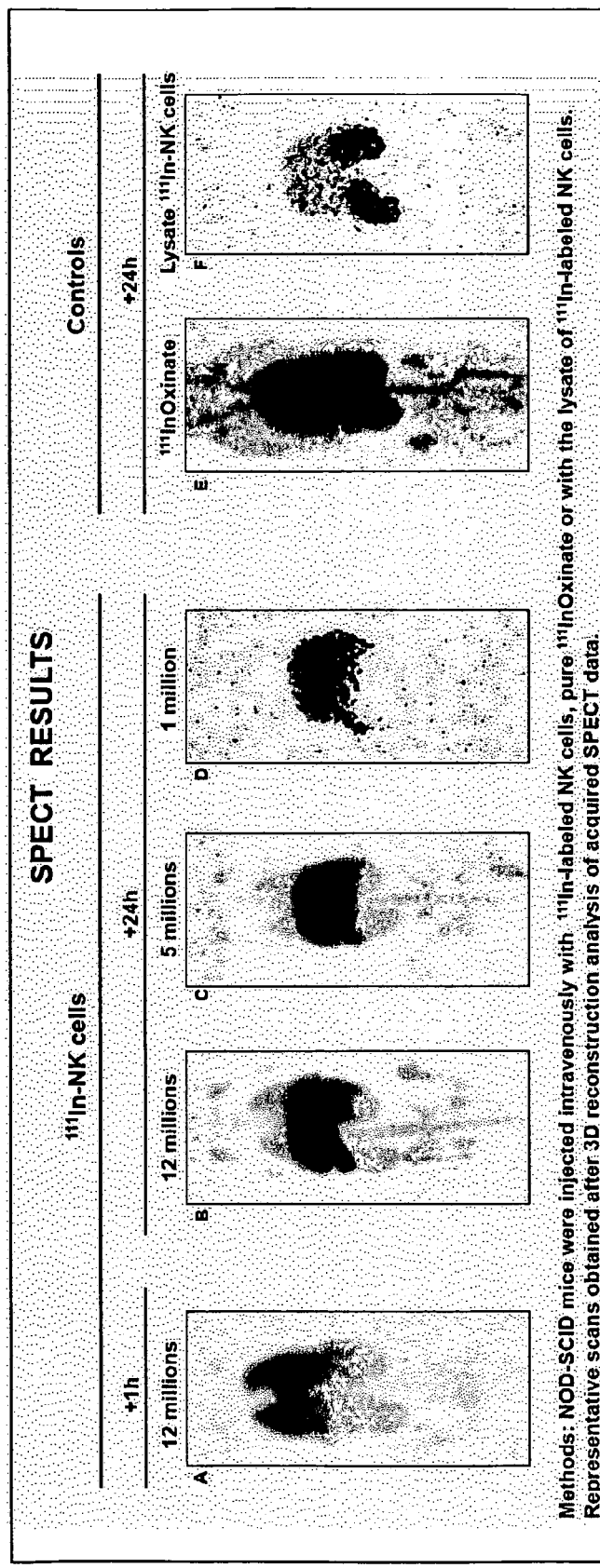

FIG. 26 SPECT results of whole NOD-SCID mice transplanted with labelled cells.

Figure 27:
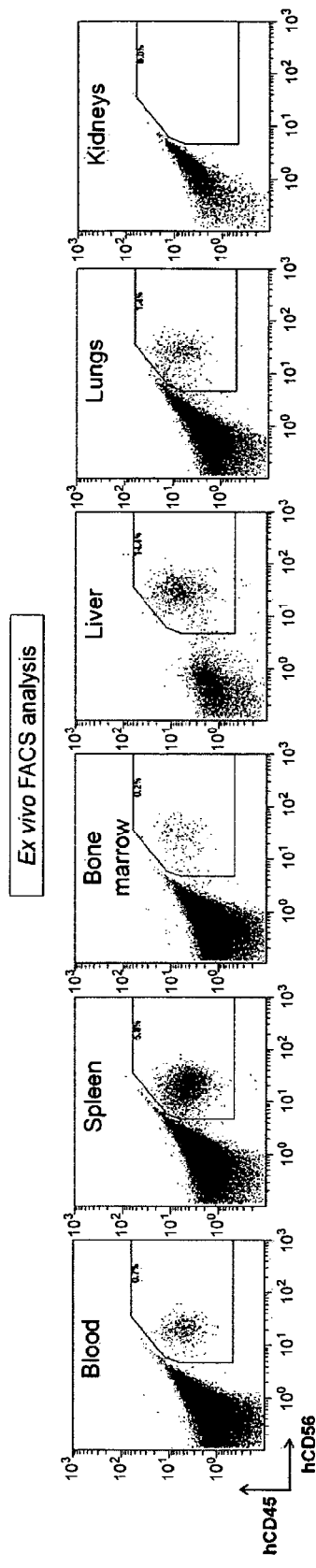

FIG. 27 Biodistribution of in vitro cultured labelled NK cells.

EXAMPLES

Material and Methods

Example 1

Cell Lines

Cell line K562 was cultured in Iscove's modified Dulbecco's medium (IMDM; Invitrogen, Carlsbad Calif., USA) containing 50 U/ml penicillin, 50 μg/ml streptomycin and 10% fetal calf serum (FCS; Integro, Zaandam, the Netherlands).

Isolation of $CD34^+$ Stem and Progenitor Cells

UCB units have been obtained at birth after normal full-term delivery after written informed consent with regard of scientific use from the cord blood bank of the Radboud University Nijmegen Medical Center (RUNMC, Nijmegen, The Netherlands). UCB samples were stored at room temperature and processed within 24 h after collection. Before storage, the red blood cell content has been reduced using standard EloHAES® separation and the mononuclear cells have been washed, cryopreserved and stored in liquid nitrogen [28]. Stored UCB units were thawed at 37° C. and resuspended in thawing buffer consisting of CLINIMACS® PBS/EDTA buffer (Miltenyi Biotech, Bergisch Gladbach, Germany), 5% HSA (Baxter Healthcare Corporation, Deerfield, USA), 3.5 mM $MgCl_2$ (Pharmacy Department, RUNMC, Nijmegen, The Netherlands) and 100 U/ml Pulmozyme (Roche, Almere, The Netherlands). Thawed UCB cells were incubated for 30 minutes at room temperature (RT) and subsequently centrifugated. After two washing steps, thawed UCB cells were resuspended in 8 ml washing buffer consisting of CLINIMACS® PBS/EDTA buffer, 0.5% HSA, 3.5 mM $MgCl_2$ and 100 U/ml Pulmozyme and labeled for 30 minutes at RT with 0.75 ml CLINIMACS® CD34 reagent (Miltenyi Biotech) and 1 ml Nanogam (Sanquin blood bank, Amsterdam, The Netherlands). After incubation, the CD34-labeled UCB sample was washed and resuspended in 100 ml washing buffer. The automated CLINIMACS® cell separator was equipped with a closed disposable CLINIMACS® tubing set type 161-01 (Miltenyi Biotech). The $CD34^+$ cell selection was performed using an automated program and after the enrichment procedure, the $CD34^+$ cell fraction was collected, and the cell number and purity were analyzed by flow cytometry. Finally, the obtained $CD34^+$ UCB cells were used directly for the NK cell generation bioprocess.

Ex Vivo Expansion and Differentiation of CD34-Positive Progenitor Cells $CD34^+$ UCB cells were transferred into Vuelife™ bags 290AC or 750AC (Cellgenix, Freiburg, Germany) and expanded and differentiated according to method III as described previously with some minor modifications [17]. In brief, for day 0-9 Expansion Medium I was used. Glycostem Basal Growth Medium (GBGM®) for cord blood (CB) (Clear Cell Technologies, Beernem, Belgium) was supplemented with 10% human serum (HS; Sanquin Bloodbank, Nijmegen, The Netherlands) a high-dose cytokine cocktail was added consisting of 25 ng/ml SCF, 25 ng/ml Flt3L, 25 ng/ml TPO and 25 ng/ml IL-7 (all CellGenix, Freiburg, Germany) and a low-dose cytokine cocktail consisting of 10 pg/ml GM-CSF (Neupogen) (Amgen, Breda, The Netherlands), 250 pg/ml G-CSF and 50 pg/ml IL-6 (both CellGenix, Freiburg, Germany). From day 10-14 Expansion II medium was used and TPO was replaced by 20 ng/ml IL-15 (CellGenix, Freiburg, Germany). During the first 14 days of culture, low molecular weight heparin (LMWH) (Clivarin®; Abbott, Wiesbaden, Germany) was added to the expansion medium in a final concentration of 25 μg/ml. cell cultures were refreshed with new medium every 2-3 days, and adjusted to a cell density of $1-2\times10^6$/ml. Cultures were maintained in a 37° C., 95% humidity, 5% CO2 incubator. Expanded cultures in Vuelife™ bags were either maintained in Vuelife™ bags or transferred to a bioreactor at around day 14 when sufficient volume of 150 ml was reached. We have used both the single use WAVE Bioreactor™ System 2/10 (GE Health, Uppsala, Sweden) and BIOSTAT® CultiBag RM system (Sartorius Stedim Biotech, Göttingen, Germany). The bioreactor cultures were started with $1\times10^6$ cells/ml in 250 ml. From day 14 onward, expanded CD34+ UCB cells were differentiated and further expanded using NK cell differentiation medium. This medium consisted of Glycostem Basal Growth Medium (GBGM®) for cord blood (CB) as used for the CD34 expansion step supplemented with 10% HS, the low-dose cytokine cocktail (as previously mentioned) and a new high-dose cytokine cocktail consisting of 20 ng/ml IL-7, 20 ng/ml SCF, 1000 U/ml IL-2 (Proleukin®; Chiron, München, Germany) and 20 ng/ml IL-15 (CellGenix). The cell density was checked two times a week and adjusted to 1.5 to $3.0 \times 10^6$ cells/ml by the addition of GBGM® NK cell differentiation medium. The conditions of the bioreactor were as follows: temperature 37° C., $CO_2$ 5%, airflow 0.1-0.21/min, rocking rate 10/min, rocking angle of 7°.

Flow Cytometry

Cell numbers and expression of cell-surface markers were determined by flow cytometry.

For immunophenotypical staining, cells were incubated with the appropriate concentration of antibodies for 30 min at 4° C. After washing, cells were resuspended in Coulter® Isoton® II Diluent (Beckman Coulter) and analyzed using the Coulter FC500 flow cytometer (Beckman Coulter). For determining the content of CD34+ cells in the UCB and the purity of the CD34 selected cells the following monoclonal antibodies were used: CD45-FITC (J33) and CD34-PE (581) (both from Beckman Coulter, Woerden, The Netherlands). The population of living CD34+ cells was determined by exclusion of 7AAD (Sigma, Bornem, Belgium) positive cells. Analysis was performed according to the most actual ISHAGE protocol.

For determining the purity of the end product after washing the following monoclonal antibodies were used: CD3-FITC (UCHT1) (Beckman Coulter, Woerden, The Netherlands); CD56-PE (NCAM16-2) (BD Biosciences Pharmingen, Breda, The Netherlands), anti-CD45-ECD (J33) (Beckman Coulter, Woerden, The Netherlands).

Also a ten colormetric analysis was used to determine the phenotype of the cultured cells. The following monoclonal antibodies were used in the appropriate concentration: CD16-FITC (NKP15), CD336(NKp44)-PE (Z231), CD3-ECD (UCHT1), CD337(NKp30)-PC5.5 (Z25), CD335 (NKp46)-PE-Cy7 (BAB281), CD314(NKG2D)-APC (ON72), CD244(2B4)-APC-alexa700 (C1.7.1), CD56-APC-Alexa750 (N901), CD161-PB (191B8), CD45-PO (J33) (all provided by Beckman Coulter, Marseille, France). The acquisition analysis was performed on the Navios™ flow-cytometer and the data were further analyzed using the Kaluza™ software (all from Beckman Coulter, Miami, Fla., USA).

Flow Cytometry-Based Cytotoxicity and Degranulation Studies

Flow cytometry-based cytotoxicity assays were performed as described previously [17,29]. Briefly, after incubation for 4 h or overnight at 37° C., 50 μl supernatant was collected and stored at −20° C. for later use to measure cytokine production. Cells in the remaining volume were harvested and the number of viable target cells was quantified by flow cytometry. Target cell survival was calculated as follows: % survival={[absolute no. viable CFSE+ target cells co-cultured with NK cells]/[absolute no. viable CFSE+ target cells cultured in medium]}*100%. The percentage specific lysis was calculated as follows: % lysis={100−[% survival]}. Degranulation of NK cells during co-culture was measured by cell surface expression of CD107a [30]. After 18 hrs of incubation at 37° C., the percentage of CD107a+ cells was determined by flow cytometry.

Preparation of the Final NK Cell Product

At the end of culture, NK cells were harvested, and the number and viability of CD56+ cells was determined by flow cytometry and ACT counter (Beckman Coulter). The UCB-NK-cell product was transferred into 600 ml transfer bags (Baxter, Deerfield, USA), centrifugated 200 g for 15 min without break and the supernatant was collected for testing of bacterial, fungal and mycoplasm contamination. NK cells were resuspended and washed twice with 500 ml CLINI-MACS® PBS/EDTA buffer supplemented with 0.5% HSA (Sanquin Blood Bank, Amsterdam, The Netherlands). After washing, NK cells were resuspended in 120-360 ml infusion buffer (NaCl 0.9%+5% HSA). Finally, viable number of $CD56^+CD3^-$ NK cells in the end-product was determined by flow cytometry and the concentration of residual IL-2, IL-7, IL-15 and SCF was measured by ELISA (R&D Systems, Abingdon, Oxon, UK).

Karyotyping of the NK Cell Product

Cytogenetic analysis was performed on the final NK cell products according to standard methods. In total 20 metaphases were G-banded using trypsin and Giemsa (GTG) and were examined per case. Karyotypes were described according to ISCN 2009 [31].

Sterility Testing of the NK Cell Product

Before and after washing in bags samples were taken and processed to check for bacterial and fungal contaminations. These samples were transferred to Bactec flasks (BD). Here we used the Bactec Ped plus for samples between 1-3 ml. Bacterial growth till day 6 should be reported as positive. The testing was done by the Department of Microbiology, RUNMC, Nijmegen, The Netherlands.

Mycoplasma Testing

Mycoplasma detection was performed on final products using the MycoAlert® Mycoplasma detection kit (Lonza, Rockland, USA) following the manufacturer's instructions. The signals were measured with the Fluostar Optima (BMG Labtech, IJsselstein, The Netherlands)

Endotoxin Test

Endotoxin level in the final products was determined using the chromogenic Limulus Amebocyte Lysate (LAL) assay (Charles River Endosafe, Charleston, S.C., USA) following the manufacturer's guidelines by the Pharmacy Department, RUNMC, Nijmegen, The Netherlands. A level of <0.25 EU/ml was set as negative endotoxin limit.

Cytokine Detection

Cytokine levels in the final products were determined using ELISA. Briefly, Maxisorp 96-well plates (NUNC) were coated overnight with 1 μg/ml of monoclonal coating antibody for IL-2, IL-7, IL-15 and SCF (all from R&D systems, Abingdon, Oxon, UK). For sample detection, biotinylated antibodies were added for IL-2 (0.2 μg/ml polyclonal Ab), IL-7 (0.2 μg/ml polyclonal Ab), IL-15 (0.25 μg/ml monoclonal Ab) and SCF (0.05 μg/ml polyclonal Ab), respectively. The extinction was measured by the TiterTek Multiscan MCC/340 plate reader (Titertek, Huntsville, Ala.). Concentrations of triplicate measurements were determined using a standard curve ranging between 1 to 2000 pg/ml of the specific cytokine.

Statistics

Results from different experiments are described as mean±standard deviation of the mean (SD), range and median. Statistical analysis was performed using student's t-test. A p-value of <0.05 was considered statistically significant.

Example 2

Tissue Collection and Mononuclear Cell Isolation

Bone marrow (BM), peripheral blood (PB), spleen (SPL) and cord blood (CB) samples were obtained at the Radboud University Nijmegen Medical Centre (RUNMC; Nijmegen, The Netherlands). BM and PB samples were obtained from healthy stem cell transplantation donors before mobilization treatment with G-CSF. SPL samples were obtained from deceased liver or kidney transplantation donors. CB samples, obtained at birth after normal full-term delivery, were provided by the cord blood bank of RUNMC. At the Erasmus Medical Centre (Rotterdam, The Netherlands), liver draining lymph node (LiLN) samples were obtained from deceased liver transplantation donors and inguinal lymph node (inLN) samples from kidney transplant recipients (not treated with immunosuppressive drugs prior to lymph node excision). After collection, each tissue sample was stored at room temperature and processed within 24 h. Lymph node and spleen samples were first forced through 74 µm netwell filters (Costar, Corning International, NY, and USA) to obtain single cell suspensions. Mononuclear cells (MNC) were isolated by density gradient centrifugation (Lymphoprep; Nycomed Pharma, Roskilde, Denmark) and cryopreserved in liquid nitrogen until further use. At least 5 independent samples of each tissue were collected. This study was performed in accordance with the regulations as set by the Medical Ethical Committees for human research of the RUNMC and the Erasmus MC, and written informed consent with regard of scientific use was obtained from all study participants or their representatives.

Multi-Color Flow Cytometry

For detailed flow cytometric (FCM) analysis of the different developmental stages and phenotype of NK cells, we designed three different 10-color FCM panels using conjugated mAbs kindly provided by Beckman Coulter (Marseille, France) with the exception of CD16-FITC (Dako, Glostrup, Denmark) and CD159c-PE (R&D Systems, Minneapolis, Calif., USA). Detailed description of the panels is shown in Table 5. For 10-color FCM, combinations of mAb-fluorochrome were balanced to avoid antibody interactions, sterical hindrance and to detect also dimly expressing populations. Before multi-color analyses, all conjugates were titrated and individually tested for sensitivity, resolution and compensation of spectral overlap. Isotype controls were used to define marker settings. Thawed MNC fractions of collected human tissues were assessed on a Navios™ 10-color flow cytometer and analyzed using Kaluza Software® 1.0 (Beckman coulter). To define NK cell developmental stages, samples were gated on the $CD45^+CD3^-$ population within $CD45^+$/SS gated cells to exclude T cells and endothelial cells (which may express CD34 but are CD45 negative[15]) from analysis. To analyze the NK cell receptor repertoire (Table 5) of committed NK cells expressing CD56, cells were further gated on $CD56^+$ cells within the $CD45^+CD3^-$ population. Cell populations >0.1% of the $CD45^+CD3^-$ population with a threshold of more than 50 cells were considered reliable. Cell populations were considered to be present in a specific tissue when at least 3 out of 5 samples showed reliable results. Cell populations that did not suffice to these criteria were excluded from further (statistical) analysis. An overview of analyzed sample sizes is shown in Table 8.

Statistical Analysis

To compare percentages of cells positive for single markers between the different tissues, a random effect logistic regression model was used that accounted for the biological diversity between samples of each tissue and for the fact that several samples of each tissue type were taken. Mean fluorescence (MFI) of specific markers between the different tissues were analyzed using ANOVA analysis with Tukey post testing. P-values <0.05 were considered significant.

Results

Example 1

Efficient Enrichment of $CD34^+$ Cells from Cryopreserved Umbilical Cord Blood

The overall aim of this study was to develop a closed ex vivo culture system for the expansion and differentiation of $CD34^+$ UCB cells into NK cells followed by the subsequent log-scale generation of $CD56^+CD3^-$ NK cells. As the initiation of our culture process requires hematopoietic progenitor cells, we optimized the $CD34^+$ enrichment procedure from cryopreserved UCB units using the CLINIMACS® system. Prior to banking in liquid nitrogen the collected UCB units used for this study (n=16) have been reduced for red blood cells and volume using ELOHAES® separation. The mean volume of 111±34 ml (range 72-175 ml) and mean WBC count of $1,503±455×10^6$ cells (range $772-2,380×10^6$) was reduced to 25 ml with a WBC count of $1,085±357×10^6$ cells (range $600-1,721×10^6$) containing $3.78±1.95×10^6$ $CD34^+$ cells (range $1.73-8.72×10^6$) (Table 1). Cryopreserved UCB units were thawed and prepared for $CD34^+$ selection using CLINIMACS® PBS/EDTA buffer containing clinical-grade DNAse. The recovery of $CD34^+$ cells after thawing was 76%±16%, which resulted in a total yield of $2.79±1.59×10^6$ $CD34^+$ cells (range $1.43-8.12×10^6$) for the selected UCB units (Table 1). Next, $CD34^+$ cells were enriched using the CLINIMACS® cell separator resulting in a mean recovery of 71%±11% (range 50-91%) (Table 2). The purity of the enriched $CD34^+$ product was 67%±14% (range 44-92%). Total recovery after thawing and CD34 enrichment was 53%±15% (range 33-82%) with a mean $CD34^+$ cell number of $1.96×10^6±1.27×10^6$ (range $0.89-6.34×10^6$) (Table 2). These results demonstrate that $CD34^+$ cells can be efficiently enriched from volume-reduced and cryopreserved UCB units providing a clinical-grade starting product for the NK cell generation and expansion culture process.

Enriched $CD34^+$ UCB cells can be efficiently expanded using static cell culture bags Previously, research scale experiments in 6-well plates showed that $CD34^+$ cells, enriched from frozen UCB units, can be efficiently expanded and differentiated into the NK cell lineage using our two step ex vivo culture process [17]. To translate this protocol into a closed culture system, we have tested ex vivo expansion of $CD34^+$ UCB cells for two weeks in static VUELIFE® AC culture bags using NK cell expansion medium I (day 0-9) and medium II (day 9-14). The mean total cell expansion for all experiments (n=7) was 39±14 and 160±69 fold after 1 and 2 weeks of culture, respectively (data not shown). These results were similar to the rate of expansion obtained after 2 weeks in 6-well plates 192±82 (n=7), and indicate that selected $CD34^+$ cells from cryopreserved UCB units can be efficiently expanded during 2 weeks of culture in disposable bags.

Superior Expansion of Highly Purified NK Cell Products Using a Bioreactor

Figure 1A:
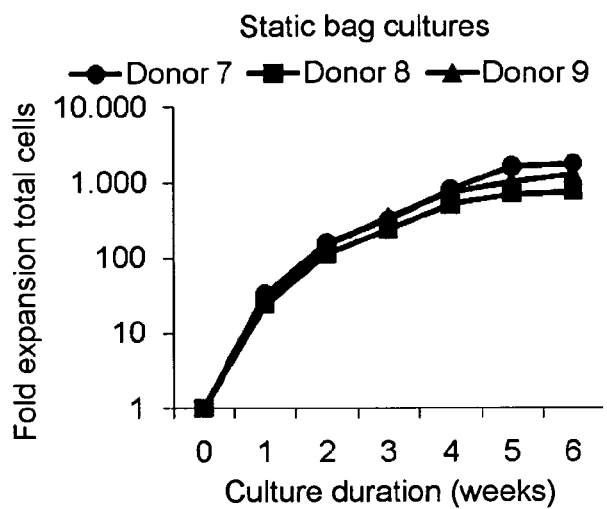
FIG. 1. Ex-vivo generation of CD56+ NK cells from cryopreserved CD34+ UCB cells. CD34-enriched UCB cells were expanded for two weeks and subsequently differentiated into NK cells for four additional weeks. Cell cultures were weekly analyzed for cell numbers and phenotype using flow cytometry. (A) Fold expansion of total cells for each donor after initial seeding of enriched CD34+ UCB cells during 6 weeks of culture using static Vuelife™ cell culture bags. (B) CD56+ cell frequency for each donor during the 6 week culture period for static bag cultures. (C) Fold expansion of total cells for each donor after initial seeding of enriched CD34+ UCB cell population during 6 weeks of culture using single use bioreactors. (D) CD56+ cell frequency for each donor during the 6 week culture period for bioreactor cultures. (E) Mean total CD56+ NK cell expansion during 4 weeks of differentiation using static bag (n=3) or bioreactor cultures (n=4). Data are depicted as mean±SD. The asterisk (*) represents a p-value of <0.05.
Figure 1B:
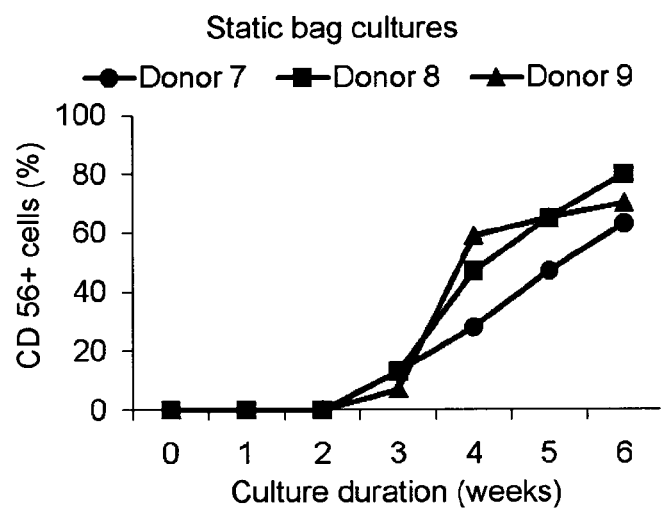
Figure 1C:
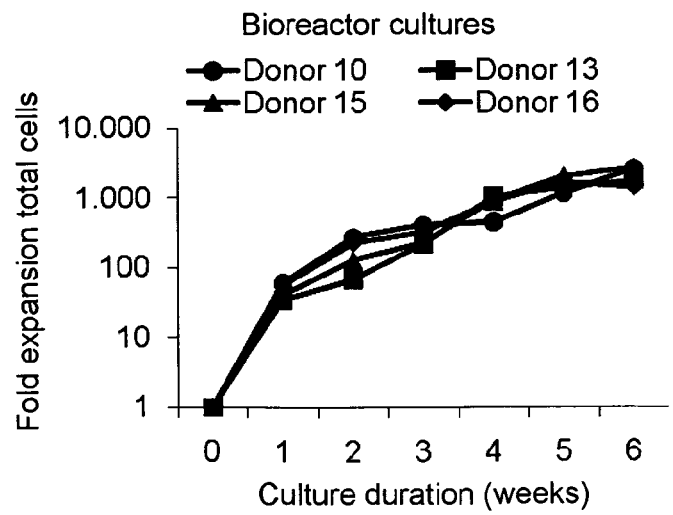
Figure 1D:
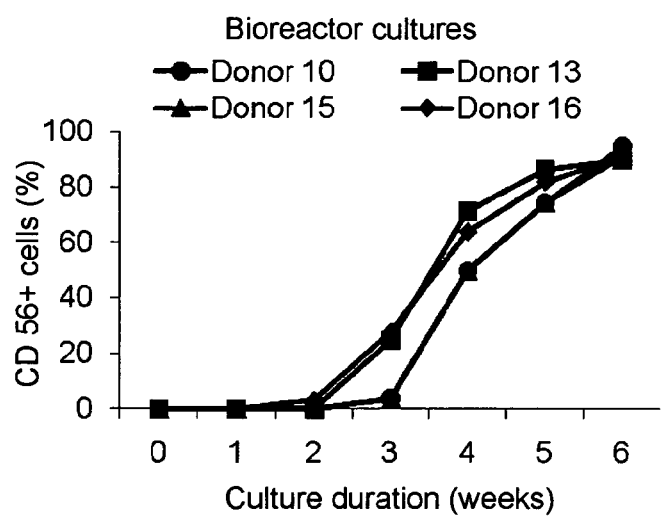
Figure 1E:
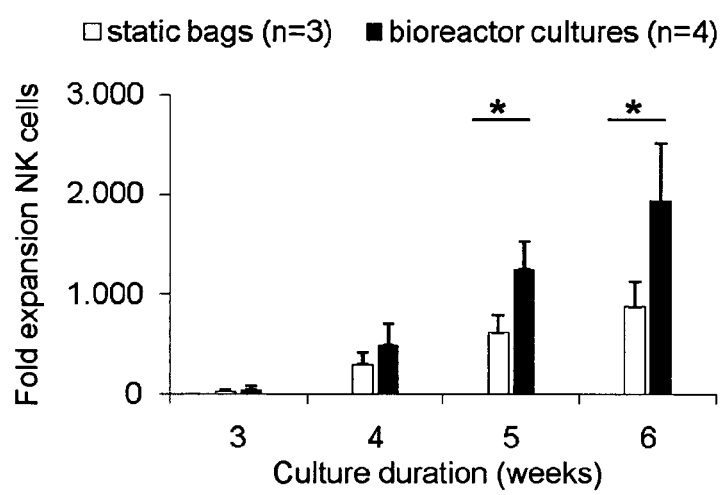

Next, we investigated whether the in the bag expanded $CD34^+$ UCB cells could be differentiated and further expanded into $CD56^+CD3^-$ NK cells. First, we continued the differentiation process in the same static bags as used for $CD34^+$ cell expansion. Therefore, we added NK cell differentiation medium containing SCF, IL-7, IL-15 and IL-2 to the bag cultures from day 14 onward. The mean total cell expansion after 6 weeks of culture in the static bags was ~1,300 fold (range 759-1,770; n=3), generating NK cell products of 0.9-1.9×10$^9$ CD56$^+$CD3$^-$ NK cells (FIG. 1A and Table 3) However, the ex vivo generation of CD56$^+$CD3$^-$ NK cells in bag cultures yielded in a purity of 71%±9% (FIG. 1B and Table 3). Because differentiation of the NK cell products was sub-optimal in the bag cultures, we next tested whether differentiation of the bag-expanded CD34$^+$ cultures into the NK cell lineage could be improved using an automated bioreactor. Therefore, in a next set of experiments expanded CD34$^+$ UCB cells were transferred at day 14 of culture into a bioreactor system with a minimal volume of 250 ml for starting the NK cell differentiation process. Although the mean total cell expansion at 6 weeks of culture in the bioreactor cultures, which was ~2,100 fold (range 1,435-2,657; n=4; FIG. 3C and Table 3), was not significantly higher compared to the bag-expanded NK cells, the differentiation and expansion rate of NK cells was significantly better in the bioreactors (FIGS. 1D and E). At week 5 and 6, the NK cell purity and fold NK cell expansion in the bioreactor cultures was significantly higher compared to the static bag cultures (FIG. 1E and Table 3). Importantly, ex vivo generation of CD56$^+$CD3$^-$ NK cells in bioreactors yielded highly purified (92%±2%; n=4) NK cell products with a total NK cell number of 1.6-3.7×10$^9$ CD56$^+$CD3$^-$ NK cells (Table 3). These data demonstrate that the combination of static bag cultures for progenitor cell expansion followed by efficient NK production in bioreactor systems result in a superior production of pure NK cell products for adoptive immunotherapy trials.

The Effect of Washing on Recovery, Phenotype and Function of Expanded NK Cells

Figure 2A:
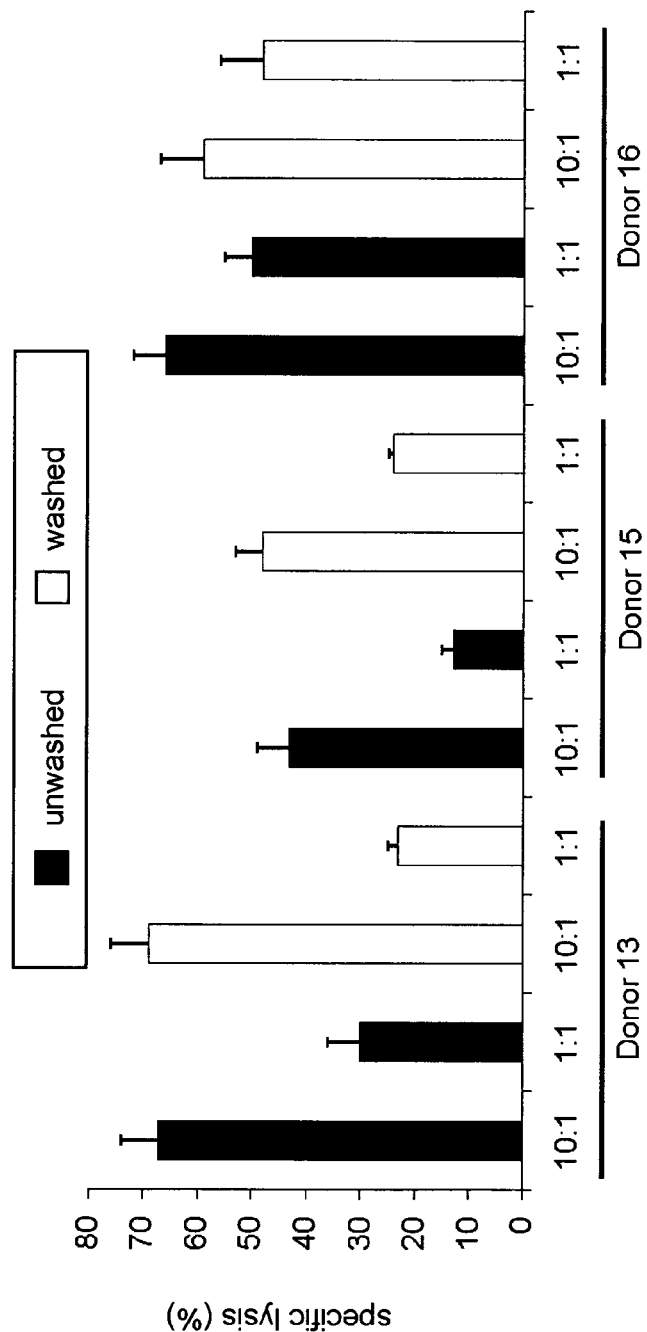
FIG. 2. Functional activity of ex vivo bioreactor-expanded NK cells before and after the washing process. (A) Cytotoxicity of ex vivo-generated NK cells against K562 cells was analyzed after 18 hours of co-culture with unwashed (black bars) and washed (white bars) NK cells from three different donors at an E:T ratio of 1:1 or 10:1. (B)
Figure 2B:
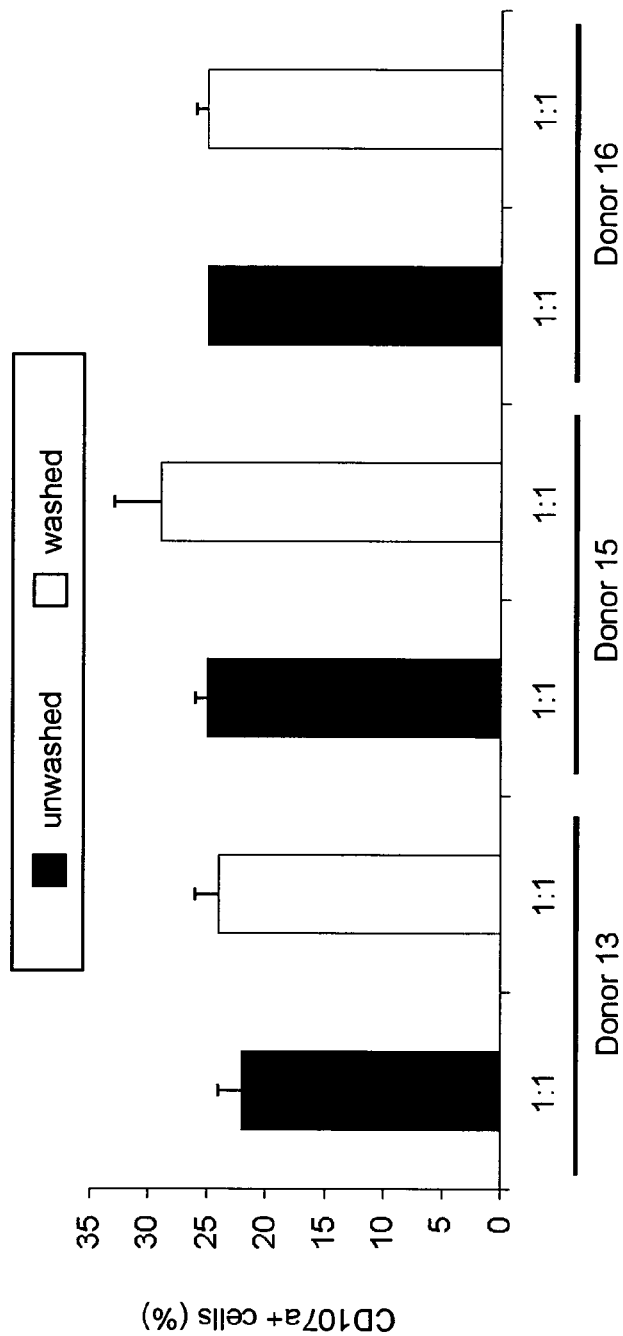

After showing that CD34$^+$ UCB cells could be efficiently enriched from frozen cord blood and successfully cultured into a pure NK cells product using a closed cell culture process, we optimized downstream processing using a closed system washing step. Two washing steps reduced total cell culture volume from 1 liter to 150 ml prior infusion. The calculated dilution factor of the washing procedure using bags was between 629-1008 fold (n=3). Washing of the NK cell product after 6 weeks of culture using a bag centrifugation protocol yielded a recovery of 82%±5% CD56$^+$CD3$^-$7AAD$^-$ NK cells (n=3). Cytotoxicity and CD107a-based degranulation assays using K562 as target cells showed that the cytolytic activity of the NK cell product before and after washing was not affected (FIGS. 2A and B). Moreover, washing of the expanded NK cells did not negatively influence the high expression of the activating receptors NKG2D (CD314), NKR-P1 (CD161), 2B4 (CD244), NKp46 (CD335) and NKp44 (CD336) (FIG. 3). These results indicate that the UCB-CD34+ cell derived –NK cells (UCB-NK) for immunotherapy could be efficiently washed using a closed process without loss of functional and phenotypical characteristics of the bioreactor-expanded NK cells.

UCB-NK Cell Therapy Products Fulfill Specific Release, Biosafety and Stability Tests During the validation runs of our closed culture and washing process, we monitored purity, cell numbers, viability, phenotype, activity and recovery of the UCB-NK cell products. All four validation runs in the bioreactor resulted in a final cell product containing >90% viable CD56$^+$CD3$^-$7AAD$^-$ NK cells. CD3+ T cells could not be detected. In addition, extensive testing was performed to ensure that our process was free of bacterial, fungal mycoplasma and endotoxin contamination (Table 4). These tests were performed at the end of the NK cell production and after the washing procedure and were negative or below specifications in all validation runs. We also tested the presence of residual SCF, IL-7, IL-15 and IL-2, which were present in the NK cell differentiation medium, by ELISA. After washing the NK cell products, the cytokine concentrations appeared to be below the specified range of <25 pg/ml SCF, IL-7 and IL-15 and <1 U/ml IL-2. Cytogenetic analysis showed that the NK cell products displayed a normal karyotype.

Figure 4A:
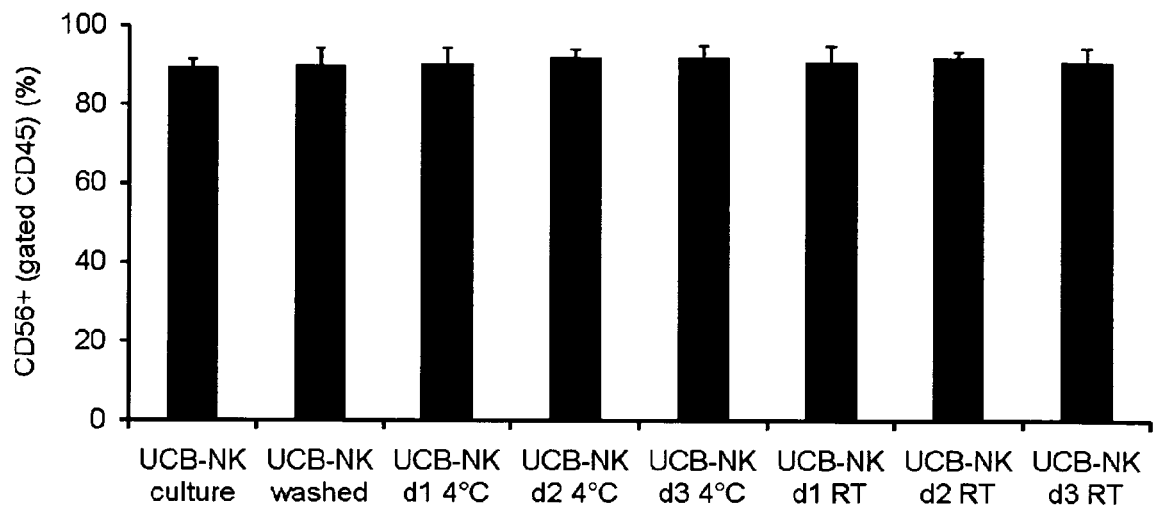
Figure 4B:
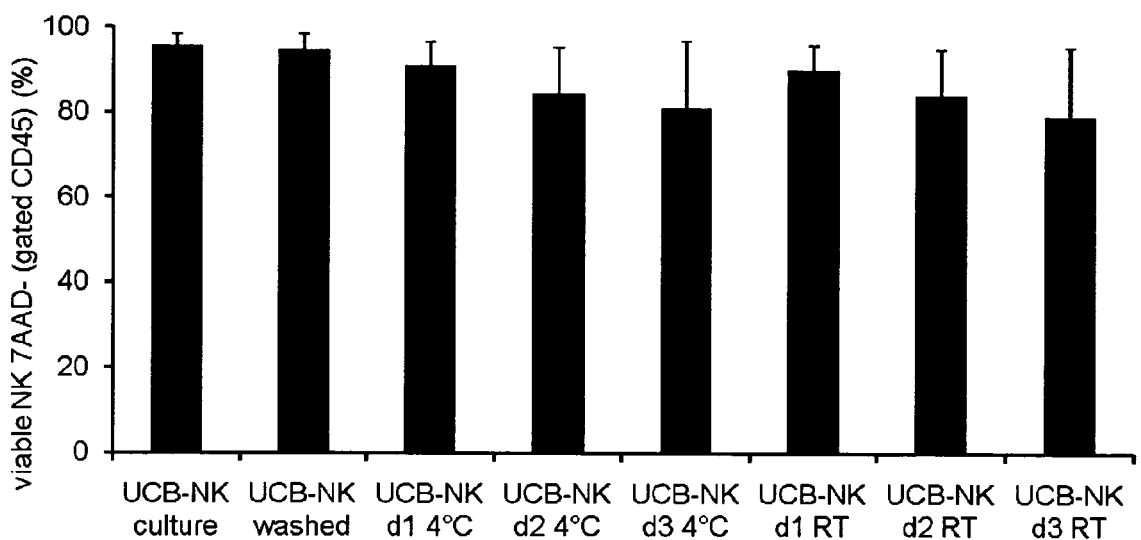

Since we intend in our phase I clinical trial to infuse freshly prepared NK cell products without cryopreservation, we determined the stability of the NK cells in order to establish a time frame for the product release testing to be finished. Therefore, we stored the UCB-NK cell product in infusion buffer (i.e. 0.9% NaCl plus 5% HSA) at 4° C. or RT, and tested purity and viability at 24, 48 and 72 hours. We could not detect a decrease in purity of the NK cell product over time and also detected no differences between storage at 4° C. or RT (FIG. 4A). A small decline in viability of CD56$^+$7AAD$^-$ NK cells was observed at day 2 or 3 after storage at both 4° C. and RT (FIG. 4B). Our specification for NK cell infusion requires a minimum of 70% viability, and we have therefore set our expiration time for UCB-NK cells at 24 hours after final formulation.

Collectively, these results demonstrate the feasibility to generate highly purified, safe and active UCB-NK cell therapy products using a fully closed cell culture and downstream manufacturing process for evaluating in a phase I dose escalation trial in poor-prognosis patients with AML.

Example 2

To identify human NK cell developmental stages within the different tissues and to analyze the distribution of different NK cell subsets and their NK cell receptor repertoire, we designed three 10-color flow cytometry (FCM) panels (Table 5). As BM is considered the origin of NK cell development [44-47], we first analyzed BM for the presence of NK cell developmental stages.

Identification of Seven NK Cell Developmental Stages in BM

Distinct NK cell developmental stages can be characterized through expression analysis of CD34, CD117, CD94 and CD56 antigens [50]. Based on that, we gated our samples on the CD45$^+$CD3$^-$ population within CD45$^+$/SS gated cells to exclude T cells and endothelial cells from analysis. Subsequently, cell subsets were first divided based on the expression of CD34 and CD117. From there, in a second step, each subset was analyzed for CD56 and CD94 expression. Using this gating strategy, we were able to identify seven distinctive developmental stages in BM (FIG. 9).

On this basis and in concert with NK cell developmental stages as identified in secondary lymphoid tissues (SLT) [50], we now propose the following model of NK development, starting from CD34$^+$CD117$^-$CD56$^-$CD94$^-$ cells (stage 1), followed by the gain of CD117 (stage 2; CD34$^+$CD117$^+$CD56$^-$CD94$^-$). Subsequently, CD34 expression is lost in stage 3a (CD34$^-$CD117$^+$CD56$^-$CD94$^-$) followed by NK cell lineage commitment through CD56 acquisition in stage 3b (CD34$^-$CD117$^+$CD56$^+$CD94$^-$). After NK cell lineage commitment, cells gain CD94 expression and develop into immature CD56$^{bright}$ NK cells (stage 4; CD34$^-$CD117$^+$CD56$^+$CD94$^+$). Through loss of CD117 expression, CD56$^{dim}$ cells start to develop (stage 5a; CD34$^-$CD117$^-$CD56$^+$CD94$^+$), followed by loss of CD94 expression in stage 5b (CD34⁻CD117⁻CD56⁺CD94⁻). The acquisition/loss of the different antigens and the presence of CD56$^{bright/dim}$ cells within each stage in BM are summarized in Table 6.

Early and Sustained CD244 Expression During In Vivo NK Cell Development

By using 10-color FCM, we were able to further specify the identified NK cell developmental stages in BM by analyzing additional antigen expression. For this purpose, we analyzed the cell surface expression of CD133, CD33, CD244 and NKG2A within each defined stage (FIG. 10). CD133 is known as a stem cell antigen that may provide an alternative to CD34 for the selection and expansion of hematopoietic cells for transplantation [56]. Together with CD34, this antigen was only expressed within stages 1 and 2. CD33 has been described as an antigen for early NK cell development[17] and was expressed in stages 2 and 3a. The CD244 receptor is suggested to be a co-receptor in activation of mature NK cells [58]. Interestingly, we found that CD244 was already expressed on CD34⁺CD117⁺ stage 2 cells in BM. During stages 3a and 3b, CD244 expression remained present and the amount of CD244⁺ cells was increased to more than 98% in stages 4 to 5b. Until now, CD244 expression was only shown to be present at early stages of NK cell differentiation during in vitro-induced human NK cell maturation [59]. The inhibitory NKG2A receptor, shown to be expressed early during NK cell maturation [53], was detected starting from stage 4 just after NK cell commitment (stage 3b) till stage 5b. In summary, as the different assessed antigens showed different expression profiles during NK cell development, we were able to further define the NK cell developmental stages (Table 7), in which CD133 expression is specific for stages 1 and 2, followed by CD33 expression in stages 2 and 3. From stage 2, CD244 is continuously expressed and NKG2A is found in stages 4 to 5b on part of the cells.

NK Cell Development Starts in BM, Followed by Further Maturation in LN, SPL and PB To assess whether the NK developmental stages can be found in other human tissues besides BM, we further analyzed samples of cord blood (CB), peripheral blood (PB), inguinal LN (inLN), liver LN (liLN) and spleen (SPL) (FIG. 11). Results showed a differential distribution of the NK cell developmental stages within the different tissues. The NK cell developmental stages in BM mainly consisted of stage 5a and 5b cells. In addition, stages 1 and 2 were only detected in BM, confirming BM as the origin of NK cell development. In CB, stage 2 cells were found, but not in PB, showing that blood of fetal origin contains more early NK progenitor cells as compared with adult blood. However, the main NK cell developmental stages in CB were stage 5a followed by stage 5b. In PB, the NK cell developmental stages mainly consisted of stage 5a and 5b cells. In contrast to other tissues, the distribution of NK cell developmental stages in LN primarily contained stage 3a and stage 3b cells, and showed lower, but similar, frequencies of stages 4 to 5b. In contrast, NK cell developmental stages in liLN and SPL consisted primarily of stages 4, 5a and 5b cells. Following the presence of the different NK developmental stages within the different tissues analyzed, these results suggest that early NK progenitor cells migrate from BM to SLT, after which pre-NK cells (stage 3a) may further develop in LN leadings to NK cell commitment (stage 3b), followed by further maturation in splenic tissue and the release of mature NK cells into the blood stream. The presence of different stages within one tissue, for instance stages other than stage 1 and 2 in BM or stage 3 in LN, indicates that in situ differentiation of remaining cells also occurs besides trafficking of developmental stages towards other tissues.

Sustained CD33 Expression in liLN During In Vivo NK Cell Development

To asses potential differences of the NK cell developmental stages within the human tissues, we further analyzed the expression of CD133, CD33, CD244 and NKG2A within the stages present in the human tissues (FIG. 12). Between BM and CB, there were no significant differences in expression of CD133, CD33 and CD244 within stage 2. The subsequent trend of CD244 acquisition was the same for each tissue and all tissues showed more than 98% CD244⁺ cells in stages 4 and 5a/b. Significant differences were seen in the expression profile of the early CD33 antigen within the different human tissues. As we previously characterized CD33 expression to be specific for stage 2 and 3a cells in BM (Table 7), CD33 expression was prolonged in CB, PB, and SPL until stage 3b. Furthermore, in liLN, CD33 expression was even sustained after NK cell commitment until stage 4. The prolonged expression of CD33 in some distinct stages and tissues suggests tissue specific NK cell developmental subsets in situ.

NKG2A Expression Reveals an Impaired NK Cell Maturation Profile in Lymphoid Tissues Having described tissue specific NK cell subsets, by the expression profile of CD33, we further analyzed if there are also tissue specific differences in the NK cell maturation pattern. As the level of NKG2A expression may be representative for the level of NK cell maturation [60,61], we analyzed the NKG2A expression profile on "committed" NK cells. Besides the significant differences in the CD33 expression profile, the expression profile of NKG2A also showed a distinction between the different human tissues. In stage 4, all tissues contained more than 95% NKG2A⁺ cells. Following NK cell developmental stages, BM, CB and PB showed a decrease in the percentage of NKG2A⁺ cells up to approximately 25% NKG2A⁺ cells in stage 5b, whereas in inLN and liLN a median of 75-80% remained NKG2A⁺ and SPL kept a median of 50% NKG2A⁺ cells. The stronger decrease of cells expressing NKG2A in BM, CB and PB as compared with other tissues was also reflected in the mean fluorescence intensity of NKG2A expression following stage 4 to 5b (FIG. 16). Overall, these data suggest that the committed NK cells in LN and SPL have a more immature phenotype as compared with cells present in BM, PB and CB.

In order to better define NK cell maturation, we extended our analyses with regard to "committed" NK cells. Therefore, we subsequently analyzed the expression of additional NK cell receptors to further asses the maturity status of the committed NK cells within the different human tissues.

Differences in the NK Cell Receptor Repertoire Suggests Distinct In Situ NK Cell Development within LN and CB Phenotypically committed NK cells (CD45⁺CD3⁻CD56⁻) can generally be divided into two distinguishable subsets: the CD56$^{bright}$CD16$^{+/-}$ and the CD56$^{dim}$CD16⁺ subset [62]. Our data, confirmed the heterogeneity of the CD56$^{bright}$CD16$^{+/-}$ and CD56$^{dim}$CD16⁺ subsets within BM, CB, PB, and LN, showing balances of CD56$^{bright}$>>CD56$^{dim}$ in LN, and CD56$^{bright}$<<CD56$^{dim}$ in BM, CB and PB (FIG. 17). Additionally, we identified a CD56$^{bright}$≈CD56$^{dim}$ balance in SPL. To further assess the maturity of the committed NK cell subsets, we analyzed the expression of various inhibitory and stimulatory NK cell receptors by using FCM panels 2 and 3 (Table 5). For analysis of the committed NK cell population, we gated on CD56⁺ cells within the CD45⁺CD3⁻ population and subsequently analyzed the expression of killer immunoglobulin-like receptors (KIR), NKG2A/C, NKG2D, CD244 and natural cytotoxicity receptors (NCR; NKp30, NKp44, NKp46). These receptors trigger and modulate mature NK cell effector function through a balance between inhibitory (KIR, NKG2A) and stimulatory signals (NKG2C, NKG2D, CD244, NCR) [42,63].

We first analyzed the NK cell receptor repertoire of the $CD56^{bright}CD16^{+/-}$ subset within the committed NK cell population of each tissue (FIG. 13). Results showed that there was no difference in the amount of $KIR^+$ cells between the tissues. Nevertheless, the mean fluorescence of KIR2DL/S2/3 and KIR3DL1 was lower in both LN and SPL, suggesting a more immature phenotype of $CD56^{bright}$ cells as compared with BM, CB and PB. Surprisingly, the proportion of $NKG2A^+$ cells was significantly lower in liLN as compared to other tissues. This may be explained by a different NK cell development in situ, as suggested by the prolonged expression of CD33 (FIG. 12). Furthermore, the amount of activating receptor positive cells, with the exception of NKp44, was also lower in liLN as compared with other tissues. This was also reflected within the $CD56^{dim}CD16^+$ subset of liLN, showing lower amounts of $NKG2D^+$, $CD244^+$ and $NKp30^+$ cells as compared with other tissues (FIG. 14). Thus, these results show that NK cell development in lymph nodes may differ in situ between LN at different anatomical locations and also other tissues.

Analysis of CB showed that both the $CD56^{bright}CD16^{+/-}$ (FIG. 13) and the $CD56^{dim}CD16^+$ (FIG. 14) subset contained significantly more $NKG2A^+$ cells as compared with other tissues. In addition, the level of NKG2A expression (MFI) in the $CD56^{bright}CD16^{+/-}$ subset was also significantly higher, which confirmed previous results [64]. NKG2C, which is the stimulatory lectin-like counterpart of NKG2A, also showed elevated expression within the $CD56^{bright}CD16^{+/-}$ subset of committed NK cells in CB (FIG. 13). Together, these data suggest that the fetal microenvironment of CB may provide prevalence for the expression of lectin-like antigens as compared with other human tissues.

Overall, the data on the NK cell receptor repertoire within the different subsets of the committed NK cells demonstrates the heterogeneity of the $CD56^{bright}CD16^{+/-}$ and $CD56^{dim}CD16^+$ within the different compartments and suggests that microenvironment may play a role in differential in situ development of the NK cell receptor repertoire of committed NK cells.

Tables

TABLE 1

Characteristics of the UCB units after EloHAES separation and cryopreservation

| | Collected UCB | Volume reduced UCB | | Thawed UCB | | |
|---|---|---|---|---|---|---|
| | Volume ml | NCs ×10⁶ | NCs ×10⁶ | CD34⁺ cells ×10⁶ | NCs ×10⁶ | CD34 cells ×10⁶ | Recovery CD34⁺ cells total % |
| Donor 1 | 88 | 1294 | 790 | 3.90 | 368 | 2.96 | 76 |
| Donor 2 | 151 | 1857 | 1312 | 5.88 | 469 | 3.73 | 63 |
| Donor 3 | 141 | 1734 | 1378 | 4.96 | 653 | 3.23 | 65 |
| Donor 4 | 87 | 1992 | 1588 | 8.72 | 819 | 8.12 | 93 |
| Donor 5 | 119 | 1821 | 1106 | 3.68 | 583 | 2.28 | 62 |
| Donor 6 | 153 | 1775 | 1519 | 3.17 | 829 | 2.15 | 68 |
| Donor 7 | 152 | 1733 | 978 | 2.08 | 440 | 2.06 | 99 |
| Donor 8 | 72 | 1210 | 760 | 2.70 | 403 | 2.07 | 77 |
| Donor 9 | 78 | 772 | 600 | 3.96 | 248 | 1.84 | 46 |
| Donor 10 | 97 | 927 | 616 | 1.73 | 386 | 1.69 | 98 |
| Donor 11 | 81 | 1207 | 974 | 2.82 | 479 | 2.52 | 89 |
| Donor 12 | 175 | 2380 | 1721 | 6.90 | 943 | 3.96 | 57 |
| Donor 13 | 95 | 1430 | 1008 | 3.04 | 558 | 2.66 | 87 |
| Donor 14 | 77 | 857 | 680 | 1.75 | 273 | 1.43 | 82 |
| Donor 15 | 88 | 1223 | 969 | 2.40 | 563 | 2.14 | 89 |
| Donor 16 | 130 | 1829 | 1364 | 2.78 | 821 | 1.82 | 66 |
| mean | 111 | 1503 | 1085 | 3.78 | 552 | 2.79 | 76 |
| SD | 34 | 455 | 357 | 1.95 | 210 | 1.59 | 16 |
| median | 96 | 1581 | 993 | 3.11 | 518 | 2.21 | 76 |
| min | 72 | 772 | 600 | 1.73 | 248 | 1.43 | 46 |
| max | 175 | 2380 | 1721 | 8.72 | 943 | 8.12 | 99 |

The table summarizes the processing of 16 UCB units used for CD34⁺ enrichment after collection, volume reduction and thawing process. Nucleated cells (NCs) were counted with the AcT10 counter (Beckman coulter). CD34⁺ cells were enumerated by single platform flow cytometry analysis. Results are depicted as mean, standard deviation, median and minimum (min) and maximum (max) volume, number of cells or percentages, respectively. (n.a.=not analyzed)

TABLE 2

Characteristics of the CD34 CLINIMACS ®separation on thawed UCB units
CD34+ positive fraction

| | Recovery after CD34 enrichment only (%) | CD34 content (%) | CD34 cells (×10⁶) | Recovery of CD34⁺ after processing (%) |
|---|---|---|---|---|
| Donor 1 | 50 | 52 | 1.47 | 38 |
| Donor 2 | 53 | 77 | 1.99 | 34 |
| Donor 3 | 73 | 70 | 2.36 | 48 |
| Donor 4 | 78 | 92 | 6.34 | 73 |
| Donor 5 | 76 | 54 | 1.74 | 47 |
| Donor 6 | 79 | 65 | 1.70 | 54 |
| Donor 7 | 82 | 64 | 1.70 | 82 |
| Donor 8 | 69 | 73 | 1.42 | 53 |
| Donor 9 | 72 | 88 | 1.32 | 33 |
| Donor 10 | 76 | 69 | 0.89 | 51 |
| Donor 11 | 91 | 65 | 2.29 | 81 |
| Donor 12 | 70 | 59 | 2.79 | 40 |

TABLE 2-continued

Characteristics of the CD34 CLINIMACS ®separation on thawed UCB units
CD34+ positive fraction

|  | Recovery after CD34 enrichment only (%) | CD34 content (%) | CD34 cells (×$10^6$) | Recovery of CD34$^+$ after processing (%) |
|---|---|---|---|---|
| Donor 13 | 55 | 84 | 1.47 | 48 |
| Donor 14 | 76 | 67 | 1.09 | 62 |
| Donor 15 | 71 | 44 | 1.52 | 63 |
| Donor 16 | 65 | 52 | 1.19 | 43 |
| mean | 71 | 67 | 1.96 | 53 |
| SD | 11 | 14 | 1.27 | 15 |
| median | 73 | 66 | 1.61 | 50 |
| min | 50 | 44 | 0.89 | 33 |
| max | 91 | 92 | 6.34 | 82 |

The table summarizes the results of the CD34$^+$ enrichment procedure of 16 UCB units. CD34$^+$ cells were enumerated by single platform flow cytometry analysis. Results are depicted as mean, standard deviation, median and minimal (min) and maximal (max) number of cells or percentages. (n.a. = not analyzed)

The table summarizes the results of the CD34$^+$ enrichment procedure of 16 UCB units. CD34$^+$ cells were enumerated by single platform flow cytometry analysis. Results are depicted as mean, standard deviation, median and minimal (min) and maximal (max) number of cells or percentages. (n.a.=not analyzed)

TABLE 3

Overview of the quantity and quality of final UCB-NK products generated from enriched CD34+ cells using static bags and single use bioreactors

|  | Donor | CD34$^+$ cells (×$10^6$) | fold expansion | CD56$^+$ cells (%) | CD56$^+$ cells (×$10^9$) |
|---|---|---|---|---|---|
| static bag | 7 | 1.7 | 1,770 | 63 | 1.9 |
|  | 8 | 1.4 | 759 | 80 | 0.9 |
|  | 9 | 1.3 | 1,291 | 70 | 1.2 |
| bioreactor | 10 | 0.9 | 2,549 | 95 | 2.2 |
|  | 13 | 1.5 | 1,764 | 90 | 2.4 |
|  | 15 | 1.5 | 2,657 | 92 | 3.7 |
|  | 16 | 1.2 | 1,435 | 92 | 1.6 |

The table summarize the generation of UCB-NK cell therapy products generated in static bags (Donor 7, 8 and 9) or bioreactors cultures (Donor 10, 13, 15 and 16). The number of CD56$^+$ NK cells was calculated by: CD56$^+$ cells = the number of CD34$^+$ cells * fold expansion total cells * % CD 56$^+$ cells.

TABLE 4

Product release testing criteria and results of the final NK cell products

| Test | Method | Specification | Donor 10 | Donor 13 | Donor 15 | Donor 16 |
|---|---|---|---|---|---|---|
| NK cell number | FCM | CD56$^+$CD3$^-$ NK cells | 2.2 × $10^9$ | 2.4 × $10^9$ | 3.7 × $10^9$ | 1.6 × $10^9$ |
| Purity | FCM | >70% CD56$^+$CD3$^-$ NK cells | 95% | 90% | 92% | 92% |
| Viability | FCM | >70% 7-AAD negative | n.a. | 98% | 97% | 93% |
| recovery | FCM | % CD56$^+$CD3$^-$ NK 7-AAD negative cells. | n.a. | 83% | 86% | 76% |
| Content CD3$^+$ T-cell | FCM | <1 × $10^4$ CD3$^+$ T cells/kg body weight of the patient | n.d. | n.d. | n.d. | n.d. |
| Content CD19$^+$ B-cells | FCM | <1 × $10^4$ CD19$^+$ B cells/kg body weight of the patient | n.a. | n.a. | n.a. | n.a. |
| Sterility | Culture | Negative for bacterial and fungal contamination | negative | negative | negative | negative |
| Mycoplasm | Luminescence assay | Negative for mycoplasm contamination | negative | negative | negative | negative |
| Endotoxin | LAL assay | <0.25 EU/ml | 0.08 | 0.02 | 0.01 | 0.01 |
| Karyotyping | Cell culture | Normal karyotype | yes | yes | yes | yes |
| Phenotype | FCM | >30% positivity for CD56, CD94, NKG2A, NCR and NKG2D. | yes | yes | yes | yes |
| Absence of cytokines | ELISA | <25 pg/ml IL-2, IL-7, IL-15 and SCF. | yes | yes | yes | yes |

The table shows an overview of product release tests and product specifications for the ex-vivo generated NK cells using a closed cell culture process. The table summarized the facts needed to provide a certificate of analysis to release an UCB-NK cell therapy product for a patient. n.a.=not analyzed in validation runs but these parameters will be scored for the clinical production and the certificate of analysis. n.d.: not detected; the test do not show any positive events. yes=the results of the test fulfill the specification relevant for the certificate of analysis.

TABLE 5

Panels used for flow cytometry

| | FITC | PE | ECD | PC5.5 | PC7 | APC | APC-A700 | APC-A750 | PB | PO |
|---|---|---|---|---|---|---|---|---|---|---|
| 1 | CD34 | CD133 | CD3 | CD159a | CD117 | CD33 | CD244 | CD56 | CD94 | CD45 |
|   | 581 | AC133 | UCHT1 | Z199.1.10 | 104D2D1 | D3HL60.251 | C1.7.1 | N901 | HP-3B1 | J33 |
| 2 | CD16 | CD159c | CD3 | — | CD158b | CD158e1 | CD158a | CD56 | CD159a | CD45 |
|   | DJ130c | 134522 | UCHT1 | — | GL183 | Z27.3.7 | EB6.B.3.1.1 | N901 | Z199.1.10 | J33 |
| 3 | CD16 | CD336 | CD3 | CD337 | CD335 | CD314 | CD244 | CD56 | — | CD45 |
|   | DJ130c | Z231 | UCHT1 | Z25 | BAB281 | ON72 | C1.7.1 | N901 | — | J33 |

Displayed are the combinations of conjugated monoclonalantibodies (mAb) against specific antigens within each panel. In addition, the clone for each specific mAb is shown. Each panel was used for flow cytometric (FCM) analysis of bone marrow, cord blood, peripheral blood, inguinal LN, liver LN, and spleen samples of human donors (all n=5). Thawed MNC fractions of the human tissue samples were assessed on a Navios™ 10-color flow cytometer and analyzed using Kaluza Software® 1.0 (Beckman coulter). Panel 1 was used to identify different NK cell developmental stages based on CD34, CD117, CD94 and CD56 expression profiles.[10] Additionally, expression of early development markers CD133 and CD33, stimulatory co-receptor 2B4 (CD244), and C-type lectin NKG2A were analyzed to refine the definition of the different NK cell developmental stages. Panel 2 and 3 were used to analyze the NK cell receptor repertoire of $CD45^+CD56^{bright}CD16^{+/-}CD3^-$ and $CD45^+CD56^{dim}CD16^+CD3^-$ NK cells consisting of inhibitory and stimulatory receptors. Inhibitory receptors contain KIR (CD158a, CD158b, CD158e1) and NKG2A (CD159a). Stimulatory receptors contain NCR (CD335/336/337), NKG2C (CD159c), NKG2D (CD314), and 2B4 (CD244).

TABLE 6

Developmental stages of NK cells in BM.

| | CD34 | CD117 | CD56 | CD94 | CD56: bright or dim |
|---|---|---|---|---|---|
| Stage 1 | + | − | − | − | − |
| Stage 2 | + | + | − | − | − |
| Stage 3a | − | + | − | − | − |
| Stage 3b | − | + | + | − | $CD56^{dim}$ |
| Stage 4 | − | + | + | + | $CD56^{bright}$ |
| Stage 5a | − | − | + | + | $CD56^{bright < dim}$ |
| Stage 5b | − | − | + | − | $CD56^{bright << dim}$ |

Main stages of NK cell development in BM based on expression profiles of CD34, CD117, CD56 and CD94.

TABLE 7

Developmental stages of NK cells in BM (continued).

| | CD133 | CD34 | CD33 | CD117 | CD244 | CD56 | CD94 | NKG2A | CD56: bright or dim |
|---|---|---|---|---|---|---|---|---|---|
| Stage 1 | +/− | + | − | − | − | − | − | − | − |
| Stage 2 | + | + | +/− | + | +/− | − | − | − | − |
| Stage 3a | − | − | +/− | + | +/− | − | − | − | − |
| Stage 3b | − | − | − | + | + | + | − | − | $CD56^{dim}$ |
| Stage 4 | − | − | − | + | + | + | + | + | $CD56^{bright}$ |
| Stage 5a | − | − | − | − | + | + | + | +/− | $CD56^{bright<dim}$ |
| Stage 5b | − | − | − | − | + | + | − | +/− | $CD56^{bright<<dim}$ |

Further identification of developmental NK cell stages in BM based on expression of CD133, CD34, CD33, CD177, CD244, NKG2A, CD56 and CD94. Indicated is the presence of each specified marker within each stage (based on the percentage of positive cells present): +=100-80%; +/−<80%; −=below reliable detection limits.

TABLE 8

Cell numbers in analyzed samples.

|  | Total cell number[1] (×$10^4$) | Gated CD45+CD3− cells[2] (×$10^4$) | Progenitor cells[3] (×$10^4$) |
|---|---|---|---|
| BM | 16.9 (8.9-34.9) | 2.8 (1.9-3.3) | 0.98 (0.7-1.2) |
| CB | 39.9 (27.5-99.9) | 12.2 (7.1-31.4) | 1.88 (0.6-5.0) |
| PB | 37.8 (35.7-38.9) | 8.8 (5.4-11.0) | 4.15 (1.1-7.7) |
| inLN | 10.0 (21.3-61.9) | 6.3 (1.2-34.4) | 2.2 (0.4-5.4) |
| liLN | 4.0 (2.5-39.6) | 7.8 (1.5-29.7) | 1.1 (0.1-3.0) |
| SPL | 40.8 (27.4-45.8) | 25.2 (13-29.8) | 3.03 (2.1-4.1) |

To define NK cell developmental stages, samples were gated on the CD45+CD3− population whithin CD45+/SS gated cells to exclude T cells and endothelial cells from analysis. For each tissue, the following items are indicated:
[1]Total cell number within the CD45+/SS gate;
[2]the amount of cells within the CD45+CD3− gate and;
[3]the total amount of cells covering all NK cell development stages. All cell numbers are shown in median (range).

Legend to table 9. The table shows all subsets during ex-vivo NK cell generation characterized with CD133, CD34, CD117, CD244, CD33, CD56, CD94, CD159a, CD45, CD3. First all CD45+/CD3− cells were identified and further analyzed according to their antigen expression. The stages are characterized by the expression of CD34, CD117, CD56 and CD94 as described in FIG. 1. The subsets of defined stages are characterized by the expression of CD133, CD244, CD33 and CD159a. The classification is further set as follows:

Stage 1: CD34+/CD117−/CD56−/CD94− (not committed to NK)
Stage 2: CD34+/CD117+/CD56−/CD94− (not committed to NK)
Stage 3a: CD34−/CD117+/CD56−/CD94− (committed to NK)
Stage 3b: CD34−/CD117+/CD56+/CD94− (committed to NK)
Stage 4: CD34−/CD117+/CD56+/CD94+ (committed to NK)
Stage 5a: CD34−/CD117−/CD56+/CD94+ (committed to NK)
Stage 5b: CD34−/CD117−/CD56+/CD94− (committed to NK)

TABLE 9

Characterization of developmental subsets of discrete stages in human tissues and during ex-vivo NK cell generation

| | | CD133 | CD34 | CD117 | CD244 | CD33 | CD56 | CD94 | CD159a |
|---|---|---|---|---|---|---|---|---|---|
| 1 | L | + | + | − | − | − | − | − | − |
| | F | + | + | − | + | − | − | − | − |
| | G | + | + | − | − | + | − | − | − |
| | E | + | + | − | + | + | − | − | − |
| | M | − | + | − | + | − | − | − | − |
| | K | − | + | − | + | + | − | − | − |
| | N | − | + | + | − | + | − | − | − |
| | P | − | + | − | − | − | − | − | − |
| 2 | L | + | + | + | − | − | − | − | − |
| | F | + | + | + | + | − | − | − | − |
| | G | + | + | + | − | + | − | − | − |
| | E | + | + | + | + | + | − | − | − |
| | K | − | + | + | + | + | − | − | − |
| | N | − | + | + | − | + | − | − | − |
| | P | − | + | + | − | − | − | − | − |
| 3a | E | + | − | + | + | + | − | − | − |
| | K | − | − | + | + | + | − | − | − |
| | M | − | − | + | + | − | − | − | − |
| | N | − | − | + | − | + | − | − | − |
| | J | − | − | + | + | − | − | − | + |
| | O | − | − | + | − | − | − | − | + |
| | P | − | − | + | − | − | − | − | − |
| 3b | K | − | − | + | + | + | + | − | − |
| | M | − | − | + | + | − | + | − | − |
| | N | − | − | + | − | + | + | − | − |
| | J | − | − | + | + | − | + | − | + |
| | B | − | − | + | + | + | + | − | + |
| | P | − | − | + | − | − | + | − | − |
| 4 | K | − | − | + | + | + | + | + | − |
| | M | − | − | + | + | − | + | + | − |
| | J | − | − | + | + | − | + | + | + |
| | B | − | − | + | + | + | + | + | + |
| 5a | K | − | − | − | + | + | + | + | − |
| | M | − | − | − | + | − | + | + | − |
| | J | − | − | − | + | − | + | + | + |
| | B | − | − | − | + | + | + | + | + |
| 5b | K | − | − | − | + | + | + | − | − |
| | M | − | − | − | + | − | + | − | − |
| | N | − | − | − | − | + | + | − | − |
| | J | − | − | − | + | − | + | − | + |
| | B | − | − | − | + | + | + | − | + |
| | P | − | − | − | − | − | + | − | − |

L: CD133+/CD244−/CD33−/CD159a−
F: CD133+/CD244+/CD33−/CD159a−
G: CD133+/CD244+/CD33+/CD159a−
E: CD133+/CD244+/CD33+/CD159a+
M: CD133−/CD244+/CD33−/CD159a−
K: CD133−/CD244+/CD33+/CD159a−
N: CD133−/CD244−/CD33+/CD159a−
J: CD133−/CD244+/CD33−/CD159a+
O: CD133−/CD244−/CD33−/CD159a+
B: CD133−/CD244+/CD33+/CD159a+
P: CD133−/CD244−/CD33−/CD159a−

The NK cell development and immature NK cells are defined as a discrete set of stages (1-5b) or a combination of stages and/or a specific subset (L, F, G, E, M, N, K, J, O, B) or combination of subsets subsets and/or a combination of stages and subsets.

TABLE 10

Appearance of identified developmental subsets of discrete stages in human tissues and during ex-vivo NK cell generation.

| Stage | Subset | BM | CB | PB | SPL | inLN | LiLN | w0 | w1 | w2 | w3 | w4 | w5 |
|---|---|---|---|---|---|---|---|---|---|---|---|---|---|
| 1 | L | 37% | | | | | | 17% | | | | | |
| | F | 5% | | | | | | 18% | | | | | |
| | G | 4% | | | | | | | | | | | |
| | E | | | | | | | 31% | 42% | 38% | | | |
| | M | | | | | | | 4% | | | | | |
| | K | | | | | | | 7% | 48% | 40% | | | |
| | N | 6% | | | | | | | | | | | |
| | P | 46% | | | | | | 23% | | | | | |
| | | 98% | | | | | | 100% | 90% | 78% | | | |
| 2 | L | 14% | | | | | | 1% | | | | | |
| | F | 44% | 63% | | | | | 10% | | | | | |
| | G | 4% | | | | | | 4% | | | | | |
| | E | 29% | 25% | | | | | 79% | 53% | 51% | | | |
| | K | | | | | | | 5% | 33% | 28% | | | |
| | N | | | | | | | 1% | | | | | |
| | P | 6% | | | | | | | | | | | |
| | | 97% | 88% | | | | | 100% | 86% | 79% | | | |
| 3a | E | | | | | | | | 6% | 5% | 3% | | |
| | K | 27% | 33% | 29% | | | | 57% | 55% | 72% | 76% | 57% | |
| | M | | 14% | | | | | 10% | 10% | 2% | | | |
| | N | 7% | 12% | | | | 44% | 18% | 24% | 22% | | | |
| | J | 18% | | | 25% | 30% | 25% | | | | | | |
| | O | 14% | | | 18% | | | | | | | | |
| | P | 29% | 31% | 31% | 40% | 46% | 20% | 9% | 6% | 1% | | | |
| | | 95% | 90% | 60% | 83% | 76% | 89% | 100% | 100% | 100% | 76% | 57% | |
| 3b | K | 25% | 40% | | | | | | | | 63% | 37% | 60% |
| | M | | | | | | | | | | 17% | 31% | 27% |
| | N | | | | | | 33% | | | | 5% | 4% | |
| | J | 48% | | 43% | 40% | 60% | 40% | | | | 8% | 19% | |
| | B | | | | | | | | | | 5% | 9% | 13% |
| | P | | | | | 26% | | | | | 2% | | |
| | | 73% | 40% | 43% | 40% | 86% | 73% | | | | 100% | 100% | 100% |
| 4 | K | | | | | | | | | | | 9% | 1% |
| | M | | | | | | | | | | | 3% | 1% |
| | J | 87% | 81% | 84% | 82% | 89% | 38% | | | | 71% | 73% | 58% |
| | B | 10% | | 11% | | | 45% | | | | 28% | 15% | 40% |
| | | 97% | 81% | 95% | 82% | 89% | 83% | | | | 99% | 100% | 100% |
| 5a | K | | | 1% | | | | | | | | 1% | 2% |
| | M | 24% | 16% | 31% | 25% | 7% | 13% | | | | | | 3% |
| | J | 75% | 82% | 1% | 71% | 88% | 68% | | | | 73% | 78% | 56% |
| | B | 1% | 67% | | 3% | | 13% | | | | 20% | 20% | 32% |
| | | 100% | 98% | 100% | 96% | 98% | 94% | | | | 93% | 99% | 93% |
| 5b | K | 6% | 11% | 12% | | | | | | | 38% | 12% | 30% |
| | M | 73% | 60% | 63% | 40% | 18% | 17% | | | | 19% | 44% | 39% |
| | N | | | 1% | | | | | | | | | |
| | J | 19% | 23% | 23% | 51% | 75% | 76% | | | | 28% | 29% | |
| | B | | | | | | | | | | 14% | | 31% |
| | P | | | 1% | | 5% | | | | | | | |
| | | 98% | 94% | 100% | 91% | 98% | 93% | | | | 99% | 85% | 100% |

Legend to table 10: The percentages of specific subsets of discrete NK cell developmental stages in human tissues and during ex-vivo NK cell generation are described by their mean size in % of Stage 1-5b cells. Here the main reliable subsets are shown within a certain stage or tissue.

TABLE 11

Identified developmental subsets of discrete stages displayed as percentages of lymphocytes present in human tissues and during ex-vivo NK cell generation.

| stage | subset | BM | CB | PB | SPL | inLN | LiLN | Ex-vivo w0 | Ex-vivo w1 | Ex-vivo w2 | Ex-vivo w3 | Ex-vivo w4 | Ex-vivo w5 |
|---|---|---|---|---|---|---|---|---|---|---|---|---|---|
| 1 | L | 0.67% | | | | | | 0.93% | | | | | |
|  | F | 0.09% | | | | | | 0.99% | | | | | |
|  | G | 0.07% | | | | | | | | | | | |
|  | E | | | | | | | 1.70% | 3.21% | 1.38% | | | |
|  | M | | | | | | | 0.22% | | | | | |
|  | K | | | | | | | 0.38% | 3.67% | 1.46% | | | |
|  | N | 0.11% | | | | | | | | | | | |
|  | P | 0.83% | | | | | | 1.26% | | | | | |
| subset total |  | 1.77% | | | | | | 5.49% | 6.88% | 2.84% | | | |
| 2 | L | 0.41% | | | | | | 0.70% | | | | | |
|  | F | 1.29% | 0.95% | | | | | 6.99% | | | | | |
|  | G | 4.00% | | | | | | 2.79% | | | | | |
|  | E | 0.85% | 0.38% | | | | | 55.20% | 8.16% | 2.23% | | | |
|  | K | | | | | | | 3.49% | 5.08% | 1.22% | | | |
|  | N | | | | | | | 0.70% | | | | | |
|  | P | 0.18% | | | | | | | | | | | |
| subset total |  | 6.73% | 1.33% | | | | | 69.87% | 13.24% | 3.45% | | | |
| 3a | E | | | | | | | | 4.62% | 4.56% | 0.67% | | |
|  | K | 0.18% | 0.34% | 0.04% | | | | | 43.86% | 50.13% | 16.06% | 0.70% | 0.65% |
|  | M | | 0.14% | | | | | | 7.69% | 9.12% | 0.45% | | |
|  | N | 0.05% | 0.12% | | | | 0.92% | | 13.85% | 21.88% | 4.91% | | |
|  | J | 0.12% | | | 0.14% | 0.09% | 0.52% | | | | | | |
|  | O | 0.09% | | | 0.10% | | | | | | | | |
|  | P | 0.19% | 0.32% | 0.04% | 0.22% | 0.14% | 0.42% | | 6.92% | 5.47% | 0.22% | | |
| subset total |  | 0.63% | 0.93% | 0.08% | 0.46% | 0.23% | 1.85% | 0.00% | 76.94% | 91.15% | 22.31% | 0.70% | 0.65% |
| 3b | K | 0.06% | 0.12% | | | | | | | | 3.19% | 3.83% | 8.87% |
|  | M | | | | | | | | | | 0.86% | 3.21% | 3.99% |
|  | N | | | | | | 0.34% | | | | 0.25% | 0.41% | |
|  | J | 0.11% | | 0.04% | 0.22% | 0.19% | 0.41% | | | | 0.41% | 1.97% | |
|  | B | | | | | | | | | | 0.25% | 0.93% | 1.92% |
|  | P | | | | | 0.08% | | | | | 0.10% | | |
| subset total |  | 0.16% | 0.12% | 0.04% | 0.22% | 0.28% | 0.75% | | | | 5.07% | 10.36% | 14.78% |
| 4 | K | | | | | | | | | | | 5.03% | 0.60% |
|  | M | | | | | | | | | | | 1.68% | 0.60% |
|  | J | 0.99% | 0.30% | 0.40% | 0.86% | 0.67% | 0.32% | | | | 9.23% | 40.80% | 34.71% |
|  | B | 0.11% | | 0.05% | | | 0.38% | | | | 3.64% | 8.38% | 23.94% |
| subset total |  | 1.11% | 0.30% | 0.46% | 0.86% | 0.67% | 0.70% | | | | 12.87% | 55.89% | 59.85% |
| 5a | K | | | 0.07% | | | | | | | | 0.19% | 0.32% |
|  | M | 1.40% | 1.08% | 2.17% | 2.27% | 0.22% | 0.24% | | | | | | 0.47% |
|  | J | 4.38% | 5.54% | 0.07% | 6.45% | 2.76% | 1.27% | | | | 2.03% | 14.87% | 8.86% |
|  | B | 0.06% | | 4.70% | | 0.09% | 0.24% | | | | 0.56% | 3.81% | 5.07% |
| subset total |  | 5.84% | 6.62% | 7.01% | 8.72% | 3.08% | 1.76% | | | | 2.59% | 18.88% | 14.72% |
| 5b | K | 0.26% | 0.25% | 0.45% | | | | | | | 0.21% | 0.24% | 1.61% |
|  | M | 3.15% | 1.35% | 2.36% | 1.23% | 0.35% | 0.25% | | | | 0.10% | 0.86% | 2.09% |
|  | N | | | 0.04% | | | | | | | | | |
|  | J | 0.82% | 0.52% | 0.86% | 1.57% | 1.46% | 1.13% | | | | 0.15% | 0.57% | |
|  | B | | | | | | | | | | 0.08% | | 1.66% |
|  | P | | | 0.04% | | 0.10% | | | | | | | |
| subset total |  | 4.23% | 2.12% | 3.74% | 2.79% | 1.90% | 1.39% | | | | 0.53% | 1.67% | 5.36% |

REFERENCES

1. Vivier E, Nunes J A, Vely F (2004) Natural killer cell signaling pathways. Science 306: 1517-1519.
2. Ljunggren H G, Malmberg K J (2007) Prospects for the use of NK cells in immunotherapy of human cancer. Nat Rev Immunol 7: 329-339.
3. Ruggeri L, Capanni M, Urbani E, Perruccio K, Shlomchik W D, et al. (2002) Effectiveness of donor natural killer cell alloreactivity in mismatched hematopoietic transplants. Science 295: 2097-2100.
4. Miller J S, Soignier Y, Panoskaltsis-Mortari A, McNearney S A, Yun G H, et al. (2005) Successful adoptive transfer and in vivo expansion of human haploidentical NK cells in patients with cancer. Blood 105: 3051-3057.
5. Rubnitz J E, Inaba H, Ribeiro R C, Pounds S, Rooney B, et al. (2010) NKAML: a pilot study to determine the safety and feasibility of haploidentical natural killer cell transplantation in childhood acute myeloid leukemia. J Clin Oncol 28: 955-959.
6. Klingemann H G, Martinson J (2004) Ex vivo expansion of natural killer cells for clinical applications. Cytotherapy 6: 15-22.
7. Passweg J R, Koehl U, Uharek L, Meyer-Monard S, Tichelli A (2006) Natural-killer-cell-based treatment in haematopoietic stem-cell transplantation. Best Pract Res Clin Haematol 19: 811-824.
8. McKenna D H, Sumstad D, Bostrom N, Kadidlo D M, Fautsch S, et al. (2007) Good manufacturing practices production of natural killer cells for immunotherapy: a six-year single-institution experience. Transfusion 47: 520-528.
9. Koehl U, Esser R, Zimmermann S, Tonn T, Kotchetkov R, et al. (2005) Ex vivo expansion of highly purified NK cells for immunotherapy after haploidentical stem cell transplantation in children. Klin Padiatr 217: 345-350.
10. Iyengar R, Handgretinger R, Babarin-Dorner A, Leimig T, Otto M, et al. (2003) Purification of human natural killer cells using a clinical-scale immunomagnetic method. Cytotherapy 5: 479-484.
11. Meyer-Monard S, Passweg J, Siegler U, Kalberer C, Koehl U, et al. (2009) Clinical-grade purification of natural killer cells in haploidentical hematopoietic stem cell transplantation. Transfusion 49: 362-371.
12. Carlens S, Gilljam M, Chambers B J, Aschan J, Guven H, et al. (2001) A new method for in vitro expansion of cytotoxic human CD3-CD56+ natural killer cells. Hum Immunol 62: 1092-1098.
13. Barkholt L, Alici E, Conrad R, Sutlu T, Gilljam M, et al. (2009) Safety analysis of ex vivo-expanded NK and NK-like T cells administered to cancer patients: a phase I clinical study. Immunotherapy 1: 753-764.
14. Berg M, Lundqvist A, McCoy P, Jr., Samsel L, Fan Y, et al. (2009) Clinical-grade ex vivo-expanded human natural killer cells up-regulate activating receptors and death receptor ligands and have enhanced cytolytic activity against tumor cells. Cytotherapy 11: 341-355.
15. Fujisaki H, Kakuda H, Shimasaki N, Imai C, Ma J, et al. (2009) Expansion of highly cytotoxic human natural killer cells for cancer cell therapy. Cancer Res 69: 4010-4017.
16. Siegler U, Meyer-Monard S, Jorger S, Stern M, Tichelli A, et al. (2010) Good manufacturing practice-compliant cell sorting and large-scale expansion of single KIR-positive alloreactive human natural killer cells for multiple infusions to leukemia patients. Cytotherapy.
17. Spanholtz J, Tordoir M, Eissens D, Preijers F, van der Meer A, et al. (2010) High log-scale expansion of functional human natural killer cells from umbilical cord blood CD34-positive cells for adoptive cancer immunotherapy. PLoS One 5: e9221.
18. Delaney C, Heimfeld S, Brashem-Stein C, Voorhies H, Manger R L, et al. (2010) Notch-mediated expansion of human cord blood progenitor cells capable of rapid myeloid reconstitution. Nat Med 16: 232-236.
19. Aktas M, Buchheiser A, Houben A, Reimann V, Radke T, et al. (2010) Good manufacturing practice-grade production of unrestricted somatic stem cell from fresh cord blood. Cytotherapy 12: 338-348.
20. Eichler H, Beck C, Schroder B, Nguyen X D, Kluter H (2002) Nonobese diabetic-severe combined immunodeficient mice transplantation of volume-reduced and thawed umbilical cord blood transplants following closed-system immunomagnetic cell selection. Transfusion 42: 1285-1292.
21. Querol S, Capmany G, Azqueta C, Gabarro M, Fornas O, et al. (2000) Direct immunomagnetic method for CD34+ cell selection from cryopreserved cord blood grafts for ex vivo expansion protocols. Transfusion 40: 625-631.
22. McNiece I K, Stoney G B, Kern B P, Briddell R A (1998) CD34+ cell selection from frozen cord blood products using the Isolex 300i and CliniMACS CD34 selection devices. J Hematother 7: 457-461.
23. Giordano R, Lazzari L, Montemurro T, Lecchi L, Porretti L, et al. (2003) Clinical-grade cell purification from thawed cord blood: an example of translational research. Bone Marrow Transplant 32: 965-966.
24. Lecchi L, Perego L, Garcea F, Ratti I, Brasca M, et al. (2009) Ten-year quality control of a semiautomated procedure of cord blood unit volume reduction. Transfusion 49: 563-569.
25. Solves P, Mirabet V, Planelles D, Blasco I, Perales A, et al. (2005) Red blood cell depletion with a semiautomated system or hydroxyethyl starch sedimentation for routine cord blood banking: a comparative study. Transfusion 45: 867-873.
26. Solves P, Mirabet V, Carbonell-Uberos F, Soler M A, Roig R (2006) Automated separation of cord blood units in top and bottom bags using the Compomat G4. Clin Lab Haematol 28: 202-207.
27. Lapierre V, Pellegrini N, Bardey I, Malugani C, Saas P, et al. (2007) Cord blood volume reduction using an automated system (Sepax) vs. a semiautomated system (Optipress II) and a manual method (hydroxyethyl starch sedimentation) for routine cord blood banking: a comparative study. Cytotherapy 9: 165-169.
28. Rubinstein P, Dobrila L, Rosenfield R E, Adamson J W, Migliaccio G, et al. (1995) Processing and cryopreservation of placental/umbilical cord blood for unrelated bone marrow reconstitution. Proc Natl Acad Sci USA 92: 10119-10122.
29. Overes I M, de Rijke B, van Horssen-Zoetbrood A, Fredrix H, de Graaf A O, et al. (2008) Expression of P2x5 in lymphoid malignancies results in LRH-1-specific cytotoxic T-cell-mediated lysis. Br J Haematol 141: 799-807.
30. Alter G, Malenfant J M, Altfeld M (2004) CD107a as a functional marker for the identification of natural killer cell activity. J Immunol Methods 294: 15-22.
31. L. G. Shaffer M L S, L. J. Campbell, editor (2009) An International System for Human Cytogenetic Nomenclature. Basel.

41. Robertson M J, Ritz J. Biology and clinical relevance of human natural killer cells. Blood. 1990; 76(12):2421-2438.
42. Papamichail M, Perez S A, Gritzapis A D, Baxevanis C N. Natural killer lymphocytes: biology, development, and function. Cancer Immunol Immunother. 2004; 53(3):176-186.
43. Ljunggren H G, Malmberg K J. Prospects for the use of NK cells in immunotherapy of human cancer. Nat Rev Immunol. 2007; 7(5):329-339.
44. Spits H, Lanier L L, Phillips J H. Development of human T and natural killer cells. Blood. 1995; 85(10):2654-2670.
45. Raulet D H. Development and tolerance of natural killer cells. Curr Opin Immunol. 1999; 11(2):129-134.
46. Colucci F, Caligiuri M A, Di Santo J P. What does it take to make a natural killer? Nat Rev Immunol. 2003; 3(5): 413-425.
47. Yokoyama W M, Kim S, French A R. The dynamic life of natural killer cells. Annu Rev Immunol. 2004; 22:405-429.
48. Di Santo J P. Natural killer cell developmental pathways: a question of balance. Annu Rev Immunol. 2006; 24:257-286.
49. Freud A G, Becknell B, Roychowdhury S et al. A human CD34(+) subset resides in lymph nodes and differentiates into CD56bright natural killer cells. Immunity. 2005; 22(3):295-304.
50. Freud A G, Yokohama A, Becknell B et al. Evidence for discrete stages of human natural killer cell differentiation in vivo. J Exp Med. 2006; 203(4):1033-1043.
51. Fehniger T A, Cooper M A, Nuovo G J et al. CD56bright natural killer cells are present in human lymph nodes and are activated by T cell-derived IL-2: a potential new link between adaptive and innate immunity. Blood. 2003; 101(8):3052-3057.
52. Ferlazzo G, Thomas D, Lin S L et al. The abundant NK cells in human secondary lymphoid tissues require activation to express killer cell Ig-like receptors and become cytolytic. J Immunol. 2004; 172(3):1455-1462.
53. Eissens D N, Schaap N P, Preijers F W et al. CD3(+)/CD19(+)-depleted grafts in HLA-matched allogeneic peripheral blood stem cell transplantation lead to early NK cell cytolytic responses and reduced inhibitory activity of NKG2A. Leukemia. 2010; 24(3):583-591.
54. Shilling H G, McQueen K L, Cheng N W et al. Reconstitution of NK cell receptor repertoire following HLA-matched hematopoietic cell transplantation. Blood. 2003; 101(9):3730-3740.
55. Male V, Hughes T, McClory S et al. Immature NK cells, capable of producing IL-22, are present in human uterine mucosa. J Immunol. 2010; 185(7):3913-3918.
56. Kobari L, Giarratana M C, Pflumio F et al. CD133+ cell selection is an alternative to CD34+ cell selection for ex vivo expansion of hematopoietic stem cells. J Hematother Stem Cell Res. 2001; 10(2):273-281.
57. Freud A G, Caligiuri M A. Human natural killer cell development. Immunol Rev. 2006; 214:56-72.
58. Sivori S, Parolini S, Falco M et al. 2B4 functions as a co-receptor in human NK cell activation. Eur J Immunol. 2000; 30(3):787-793.
59. Sivori S, Falco M, Marcenaro E et al. Early expression of triggering receptors and regulatory role of 2B4 in human natural killer cell precursors undergoing in vitro differentiation. Proc Natl Acad Sci USA. 2002; 99(7): 4526-4531.
60. Nguyen S, Dhedin N, Vernant J P et al. NK cell reconstitution after haploidentical hematopoietic stem cell transplants: immaturity of NK cells and inhibitory effect of NKG2A override GvL effect. Blood. 2005; 105(10): 4135-4142.
61. Cooley S, Xiao F, Pitt M et al. A subpopulation of human peripheral blood NK cells that lacks inhibitory receptors for self MHC is developmentally immature. Blood. 2007
62. Cooper M A, Fehniger T A, Caligiuri M A. The biology of human natural killer-cell subsets. Trends Immunol. 2001; 22(11):633-640.
63. Farag S S, Caligiuri M A. Human natural killer cell development and biology. Blood Rev. 2006; 20(3):123-137.
64. Wang Y, Xu H, Zheng X et al. High expression of NKG2A/CD94 and low expression of granzyme B are associated with reduced cord blood NK cell activity. Cell Mol Immunol. 2007; 4(5):377-382.
65. Yu J, Mao H C, Wei M et al. CD94 surface density identifies a functional intermediary between the CD56bright and CD56dim human NK cell subsets. Blood. 2009:blood-2009.
66. Braud V M, Allan D S, O'Callaghan C A et al. HLA-E binds to natural killer cell receptors CD94/NKG2A, B and C. Nature. 1998; 391(6669):795-799.
67. Kaiser B K, Pizarro J C, Kerns J, Strong R K. Structural basis for NKG2A/CD94 recognition of HLA-E. Proc Natl Acad Sci USA. 2008; 105(18):6696-6701.
68. Peruzzi G, Masilamani M, Borrego F, Coligan J E. Endocytosis as a mechanism of regulating natural killer cell function: unique endocytic and trafficking pathway for CD94/NKG2A. Immunol Res. 2009; 43(1-3):210-222.
69. Moroso V, Metselaar H J, Mancham S et al. Liver grafts contain a unique subset of natural killer cells that are transferred into the recipient after liver transplantation. Liver Transpl. 2010; 16(7):895-908.
70. Chisari F V. Cytotoxic T cells and viral hepatitis. J Clin Invest. 1997; 99(7):1472-1477.
71. Yu S, Nakafusa Y, Flye M W. Portal vein administration of donor cells promotes peripheral allospecific hyporesponsiveness and graft tolerance. Surgery. 1994; 116(2): 229-234.
72. Dalle J H, Menezes J, Wagner E et al. Characterization of cord blood natural killer cells: implications for transplantation and neonatal infections. Pediatr Res. 2005; 57(5 Pt 1):649-655.
73. Tanaka H, Kai S, Yamaguchi M et al. Analysis of natural killer (NK) cell activity and adhesion molecules on NK cells from umbilical cord blood. Eur J Haematol. 2003; 71(1):29-38.
74. Spanholtz J, Tordoir M, Eissens D et al. High Log-Scale Expansion of Functional Human Natural Killer Cells from Umbilical Cord Blood CD34-Positive Cells for Adoptive Cancer Immunotherapy. PLoS ONE. 2010; 5(2):e9221.
75. Zhao X Y, Huang X J, Liu K Y, Xu L P, Liu D H. Reconstitution of Natural Killer Cell Receptor Repertoires after Unmanipulated HLA-Mismatched/Haploidentical Blood and Marrow Transplantation: Analyses of CD94:NKG2A and Killer Immunoglobulin-Like Receptor Expression and Their Associations with Clinical Outcome. Biol Blood Marrow Transplant. 2007; 13(6):734-744.

The invention claimed is:
1. A method for producing a collection of natural killer (NK) cells wherein the method is adapted into a closed-system bioprocess for the production of allogeneic NK cell batches under GMP conditions, said method comprising:

i—providing a sample comprising CD34⁺ hematopoietic stem cells, or stem cells and progenitor cells, from human postembryonic tissue, ii—culturing, under static conditions, cells of the sample in a culture medium in a disposable bag for culturing mammalian cells at a cell density of at least $0.5\times10^6$ cells/ml for at least 7 days, wherein the culture medium comprises human serum, a collection of cytokines, and low molecular weight heparin, wherein said collection of cytokines comprises three or more of stem cell factor (SCF), flt-3Ligand (FLT-3L), thrombopoietin (TPO), and interleukin-7 (IL-7) and three or more of granulocyte-macrophage-colony-stimulating factor (GM-CSF), granulocyte-colony-stimulating factor (G-CSF), interleukin-6 (IL-6), leukaemia-inhibitory factor (LIF), and Macrophage-inflammatory protein-1alpha (MIP-I alpha), thereby obtaining a collection of cultured stem cells, and progenitor cells, from human postembryonic tissue, wherein said tissue contains a plurality of progenitor cells committed to the NK cell lineage, and iii—culturing cells obtained in step (ii) for at least 7 days at a cell density of between 1.5 and $3.0\times10^6$ cells/ml, wherein the culture medium is continuously mixed during culture, wherein the culture medium comprises human serum and a collection of cytokines, wherein said collection of cytokines comprises three or more of stem cell factor (SCF), interleukin-7 (IL-7), interleukin-15, and interleukin-2 and three or more of granulocyte-macrophage-colony-stimulating factor (GM-CSF), granulocyte-colony-stimulating factor (G-CSF), interleukin-6 (IL-6), leukaemia-inhibitory factor (LIF), and Macrophage-inflammatory protein-1 alpha (MIP-I alpha), thereby obtaining a collection of cultured cells containing a plurality of NK cells or NK progenitor cells or both, wherein at least 90% of the cultured cells in the collection are CD56⁺CD3⁻ NK cells.

2. A method according to claim 1, wherein the cells obtained in step (iii), are harvested.

3. A method according to claim 2, wherein said harvested cells are washed in a closed system such that culture medium components are diluted at least 500 fold and are replaced by a serum free solution that is compatible with human administration wherein said solution comprises human serum albumin.

4. A method according to claim 2, wherein said harvested cells are stored for at least one day at a temperature of between room temperature and 0° C.

5. A method according to claim 2, wherein said harvested cells are divided into at least 5 portions and stored at a temperature below −70° C.

6. A method for producing a collection of natural killer (NK) cells wherein the method is adapted into a closed-system bioprocess for the production of allogeneic NK cell batches under GMP conditions, said method comprising:

i—providing a sample comprising CD34+ hematopoietic stem cells, or stem cells and progenitor cells, from human postembryonic tissue, ii—culturing, under static conditions, cells of the sample in a culture medium in a disposable bag for culturing mammalian cells at a cell density of at least $0.5\times10^6$ cells/ml for at least 7 days, wherein the culture medium comprises human serum, a collection of cytokines, and low molecular weight heparin, wherein said collection of cytokines comprises three or more of stem cell factor (SCF), flt-3Ligand (FLT-3L), thrombopoietin (TPO), and interleukin-7 (IL-7) and three or more of granulocyte-macrophage-colony-stimulating factor (GM-CSF), granulocyte-colony-stimulating factor (G-CSF), interleukin-6 (IL-6), leukaemia-inhibitory factor (LIF), and Macrophage-inflammatory protein-1alpha (MIP-I alpha), thereby obtaining a collection of cultured stem cells and progenitor cells from human postembryonic tissue, wherein said tissue contains a plurality of progenitor cells committed to the NK cell lineage, and iia—culturing cells collected from step (ii) wherein the culture medium is continuously mixed during culture at a cell density of at least $0.5\times10^6$ for at least 4 days in a culture medium comprising human serum, a collection of cytokines and low molecular weight heparin, wherein said collection of cytokines comprises three or more of stem cell factor (SCF), flt-3Ligand (FLT-3L), interleukin-15, and interleukin-7 (IL-7), and three or more of granulocyte-macrophage-colony-stimulating factor (GM-CSF), granulocyte-colony-stimulating factor (G-CSF), interleukin-6 (IL-6), leukaemia-inhibitory factor (LIF), and Macrophage-inflammatory protein-1alpha (MIP-I alpha), thereby obtaining a collection of cultured stem cells, progenitor cells, or both, containing a plurality of progenitor cells committed to the NK cell lineage.

7. The method according to claim 6, further comprising step iii which follows steps (ii) and (iia)

iii—culturing cells obtained in step (iia) for at least 7 days at a cell density of between 1.5 and $3.0\times10^6$ cells/ml, wherein the culture medium is continuously mixed during culturing, wherein the culture medium comprises human serum and a collection of cytokines, wherein said collection of cytokines comprises three or more of stem cell factor (SCF), interleukin-7 (IL-7), interleukin-15, and interleukin-2 and three or more of granulocyte-macrophage-colony-stimulating factor (GM-CSF), granulocyte-colony-stimulating factor (G-CSF), interleukin-6 (IL-6), leukaemia-inhibitory factor (LIF), and Macrophage-inflammatory protein-1alpha (MIP-I alpha), thereby obtaining a collection of cultured cells containing a plurality of NK cells, NK progenitor cells, or both.

8. A method for producing a collection of natural killer (NK) cells wherein the method is adapted into a closed-system bioprocess for the production of allogeneic NK cell batches under GMP conditions, said method comprising:

i—providing a sample comprising CD34⁺ hematopoietic stem cells, or stem cells and progenitor cells, from human postembryonic tissue, ii—culturing, under static conditions, cells of the sample in a culture medium in a disposable bag for culturing mammalian cells at a cell density of at least $0.5\times10^6$ cells/ml for at least 7 days, wherein the culture medium comprises human serum, a collection of cytokines, and low molecular weight heparin, wherein said collection of cytokines comprises three or more of stem cell factor (SCF), flt-3Ligand (FLT-3L), thrombopoietin (TPO), and interleukin-7 (IL-7), and three or more of granulocyte-macrophage-colony-stimulating factor (GM-CSF), granulocyte-colony-stimulating factor (G-CSF), interleukin-6 (IL-6), leukaemia-inhibitory factor (LIF), and Macrophage-inflammatory protein-1alpha (MIP-I alpha), thereby obtaining a collection of cultured stem cells, and progenitor cells, from human postembryonic tissue, wherein said tissue contains a plurality of progenitor cells committed to the NK cell lineage, and iii—culturing cells obtained in step (ii) for at least 7 days at a cell density of between 1.5 and $3.0\times10^6$ cells/ml, wherein the culture medium is continuously mixed during culture, wherein the culture medium comprises human serum and a collection of cytokines, wherein said collection of cytokines comprises three or more of stem cell factor (SCF), interleukin-7 (IL-7), interleukin-15, and interleukin-2, and three or more of granulocyte-macrophage-colony-stimulating factor (GM-CSF), granulocyte-colony-stimulating factor (G-CSF), interleukin-6 (IL-6), leukaemia-inhibitory factor (LIF), and Macrophage-inflammatory protein-1 alpha (MIP-I alpha), thereby obtaining a collection of cultured cells containing a plurality of NK cells or NK progenitor cells or both, wherein at least 90% of the cultured cells in the collection are $CD56^+CD3^-$ NK cells, and wherein the collection of cultured cells is essentially free of $CD3^+$ T cells.

* * * * *